US012788775B2

(12) United States Patent
Yang

(10) Patent No.: US 12,788,775 B2
(45) Date of Patent: Nov. 10, 2026

(54) METHOD OF TREATMENT USING META-ARSENITE

(71) Applicants: KOMIPHARM INTERNATIONAL AUSTRALIA PTY LTD, Burwood (AU); PANAPHIX, INC., George Town Grand Cayman (KY)

(72) Inventor: Yong-jin Yang, Seongnam-si (KR)

(73) Assignees: KOMIPHARM INTERNATIONAL AUSTRALIA PTY LTD, Burwood (AU); PANAPHIX, INC., George Town Grand Cayman (KY)

( * ) Notice: Subject to any disclaimer, the term of this patent is extended or adjusted under 35 U.S.C. 154(b) by 861 days.

(21) Appl. No.: 17/904,207

(22) PCT Filed: Feb. 15, 2021

(86) PCT No.: PCT/AU2021/050128

§ 371 (c)(1),
(2) Date: Aug. 12, 2022

(87) PCT Pub. No.: WO2021/159187

PCT Pub. Date: Aug. 19, 2021

(65) Prior Publication Data

US 2023/0123135 A1 Apr. 20, 2023

(30) Foreign Application Priority Data

Feb. 16, 2020 (AU) ................................ 2020900433
Jan. 29, 2021 (AU) ................................ 2021900204

(51) Int. Cl.

*A61K 33/36* (2006.01)
*A61K 9/00* (2006.01)
*A61K 9/20* (2006.01)
*A61K 9/28* (2006.01)
*A61P 29/00* (2006.01)

(52) U.S. Cl.

CPC ............ *A61K 33/36* (2013.01); *A61K 9/0053* (2013.01); *A61K 9/2009* (2013.01); *A61K 9/2054* (2013.01); *A61K 9/2059* (2013.01); *A61K 9/2846* (2013.01); *A61P 29/00* (2018.01)

(58) Field of Classification Search

None
See application file for complete search history.

(56) References Cited

U.S. PATENT DOCUMENTS 6,063,363 A 5/2000 Goodwin et al.
2003/0176337 A1* 9/2003 Hancock ................ A61K 38/16 530/324
2003/0195350 A1* 10/2003 Leyland-Jones ....... B82Y 30/00 530/324
2008/0193560 A1* 8/2008 Hwang ................... A61P 11/06 424/623

FOREIGN PATENT DOCUMENTS

EP 1369120 A1 12/2003
EP 2114419 4/2014
JP 2010518022 A 5/2010
WO 2006104292 10/2006
WO 2009072779 6/2009
WO WO-2009072779 A1 * 6/2009 ............. A61P 31/12
WO 2019178643 9/2019

OTHER PUBLICATIONS

Wong et al. Future Medicinal Chemistry 2017 9(2):169-178 (Year: 2017).*

Simonis et al. EMBO Molecular Medicine 2021 13 (e13105):1-15 (Year: 2021).*

Kumar et al. Antimicrobial Agents and Chemotherapy 2022 66(1)(e01543-21):1-12 (Year: 2022).*

Kawai et al. (Nature Immunology 2006 7(2):131-137 (Year: 2006).*

Zhu et al. New England Journal of Medicine 2020 382(8):727-733; published in updated form Jan. 29, 2020 (Year: 2020).*

Song et al. Clinica Chimica Acta 2020 509:280-287 (Year: 2020).*

Tanaka et al. Immunotherapy 2016 8(8):959-970 (Year: 2016).*

JP Application No. 2022-549149 , "Office Action", Jan. 21, 2025, 8 pages.

EP21754353.7, "Extended European Search Report", Mailed on Jul. 13, 2023, 13 pages.

Guo-Xiang et al., "Arsenious Acid and Sodium Chloride Injection for the Novel Coronavirus Pneumonia and Severe Malignant Diseases Caused by Corona Viruses and Other Viruses Based on Empirical Use of Traditional Chinese Medicine", Central South Pharmacy, vol. 18, No. 3, XP009526571, Mar. 1, 2020, pp. 337-340.

SG11202251876E, "Written Opinion", Sep. 8, 2025, 8 pages.

Machitani M, Yasukawa M, Nakashima J, Furuichi Y, Masutomi K. RNA-dependent RNA polymerase, RdRP, a promising therapeutic target for cancer and potentially COVID-19. Cancer Sci. Aug. 17, 2020;111(11):3976-84. doi: 10.1111/cas.14618.

Phatak P, Dai F, Butler M, et al. (2008) KML001 Cytotoxic Activity Is Associated with Its Binding to Telomeric Sequences and Telomere Erosion in Prostate Cancer Cells. Cancer Therapy: Preclinical 14(14): 4593-4603.

Buensalido et al., Rhinovirus (RV) Infection (Common Cold), Practice Essentials, Background, Pathophysiology, Medscape, Available Online at: https://emedicine.medscape.com/article/227820-overview, Jul. 30, 2019, 6 pages.

Carrasco-Hernandez et al., Are RNA Viruses Candidate Agents for the Next Global Pandemic? A Review, ILAR Journal, vol. 58, No. 3, Dec. 15, 2017, pp. 343-358.

(Continued)

*Primary Examiner* — Melissa S Mercier
*Assistant Examiner* — Caralynne E Helm
(74) *Attorney, Agent, or Firm* — Kilpatrick Townsend & Stockton LLP

(57) ABSTRACT

The present invention relates to the use of sodium meta-arsenite or potassium meta-arsenite in methods of a) reducing an inflammatory response due to a viral infection, b) treating or preventing an inflammatory condition due to a viral infection, or c) treating or preventing hypercytokinemia due to a viral infection. The invention also relates to a method of treating or preventing a viral infection in a subject.

3 Claims, 13 Drawing Sheets

(56) References Cited

OTHER PUBLICATIONS

Chaudhry et al., Role of Cytokines as a Double-Edged Sword in Sepsis, In Vivo, vol. 27, No. 6, Nov.-Dec. 2013, pp. 669-684.
International Application No. PCT/AU2021/050128, International Search Report and Written Opinion mailed on Apr. 19, 2021, 12 pages.

* cited by examiner

METHOD OF TREATMENT USING META-ARSENITE

The present application claims priority from Australian provisional patent application no. 2020900433 filed 16 Feb. 2020 and from Australian provisional patent application no. 2021900204 filed 29 Jan. 2021. The entire contents of Australian provisional patent application nos. 2020900433 and 2021900204 are incorporated herein by reference.

FIELD OF THE INVENTION

The present invention relates to a method of reducing an inflammatory response due to a viral infection in a subject, and to a method of treating or preventing an inflammatory condition due to a viral infection in a subject.

BACKGROUND

An inflammatory response is produced by the body in response to injury, infection and other insults. The inflammatory response involves a cascade of both proinflammatory and anti-inflammatory cytokines. The balance between these cytokines often determines the outcome after infection or injury.

For a successful outcome after an infection or injury, production of proinflammatory cytokines results in recruitment of blood leukocytes, activation of tissue macrophages, and production of immune mediators.

However, in some circumstances, such as sepsis, or following infections with infectious agents such as viruses, such as avian influenza or certain strains of coronavirus (e.g., SARS-CoV, and SARS-CoV-2), inflammatory response to the infection can lead to acute inflammatory conditions in which there is unregulated production of proinflammatory cytokines such as tumour necrosis factor alpha (TNF-α), interleukin 1 beta (IL-1β) and interleukin 6 (IL-6). Such unregulated production of proinflammatory cytokines can lead to pneumonia, and/or multiple organ failure, and in susceptible individuals, can be fatal.

Excessive, and in some cases unregulated, secretion and/or production of proinflammatory cytokines is often a factor in some viral infections which can lead to a rapid escalation in disease symptoms. For example, coronaviruses (CoV) are a large family of viruses that cause illness ranging from the common cold to more severe diseases, and have been known to cause increased and in some cases unregulated secretion of proinflammatory cytokines. Examples of coronavirus include MERS-CoV, SARS-CoV, and SARS-CoV-2. Common signs of infection by coronavirus include respiratory symptoms, fever, cough, shortness of breath and breathing difficulties. In more severe cases, infection can cause pneumonia, severe acute respiratory syndrome, kidney failure and death.

Thus, there is a need for improved pharmaceutical compositions for use in the treatment or prevention of inflammatory conditions in which there is unregulated production of proinflammatory cytokines due to viral infection.

SUMMARY OF THE INVENTION

The present inventor has found that sodium meta-arsenite ($O{=}As{-}O^{-}Na^{+}$) (SMA) or potassium meta-arsenite ($O{=}As{-}O^{-}K^{+}$) (KMA) is capable of reducing or inhibiting production of the proinflammatory cytokines TNF-α, IL-1β and IL-6 from macrophages.

Accordingly, a first aspect provides a method of reducing an inflammatory response due to a viral infection in a subject, comprising administering to the subject an effective amount of sodium meta-arsenite ($O{=}As{-}O^{-}Na^{+}$) or potassium meta-arsenite ($O{=}As{-}O^{-}K^{+}$).

A further first aspect provides sodium meta-arsenite ($O{=}As{-}O^{-}Na^{+}$) or potassium meta-arsenite ($O{=}As{-}O^{-}K^{+}$) for use in reducing an inflammatory response due to a viral infection in a subject; or use of sodium meta-arsenite ($O{=}As{-}O^{-}Na^{+}$) or potassium meta-arsenite ($O{=}As{-}O^{-}K^{+}$) in the manufacture of a medicament for reducing an inflammatory response due to a viral infection in a subject.

The inventor envisages that SMA and KMA may be used for the treatment or prevention of conditions resulting from an inflammatory response to a viral infection (inflammatory condition due to a viral infection).

Accordingly, a second aspect provides a method of treating or preventing an inflammatory condition due to a viral infection in a subject, comprising administering to the subject an effective amount of sodium meta-arsenite ($O{=}As{-}O^{-}Na^{+}$) or potassium meta-arsenite ($O{=}As{-}O^{-}K^{+}$).

A further second aspect provides sodium meta-arsenite ($O{=}As{-}O^{-}Na^{+}$) or potassium meta-arsenite ($O{=}As{-}O^{-}K^{+}$) for use in treating or preventing an inflammatory condition due to a viral infection in a subject; or use of sodium meta-arsenite ($O{=}As{-}O^{-}Na^{+}$) or potassium meta-arsenite ($O{=}As{-}O^{-}K^{+}$) in the manufacture of a medicament for treating or preventing an inflammatory condition due to a viral infection in a subject.

A third aspect provides a method of treating or preventing hypercytokinemia due to a viral infection in a subject, comprising administering to the subject an effective amount of sodium meta-arsenite ($O{=}As{-}O^{-}Na^{+}$) or potassium meta-arsenite ($O{=}As{-}O^{-}K^{+}$).

A further third aspect provides sodium meta-arsenite ($O{=}As{-}O^{-}Na^{+}$) or potassium meta-arsenite ($O{=}As{-}O^{-}K^{+}$) for use in treating or preventing hypercytokinemia due to a viral infection in a subject; or use of sodium meta-arsenite ($O{=}As{-}O^{-}Na^{+}$) or potassium meta-arsenite ($O{=}As{-}O^{-}K^{+}$) in the manufacture of a medicament for treating or preventing hypercytokinemia due to a viral infection in a subject.

A fourth aspect provides a method of treating a viral infection in a subject, comprising administering to the subject an effective amount of sodium meta-arsenite ($O{=}As{-}O^{-}Na^{+}$) or potassium meta-arsenite ($O{=}As{-}O^{-}K^{+}$).

A further fourth aspect provides sodium meta-arsenite ($O{=}As{-}O^{-}Na^{+}$) or potassium meta-arsenite ($O{=}As{-}O^{-}K^{+}$) for use in treating a viral infection in a subject; or use of sodium meta-arsenite ($O{=}As{-}O^{-}Na^{+}$) or potassium meta-arsenite ($O{=}As{-}O^{-}K^{+}$) in the manufacture of a medicament for treating a viral infection in a subject.

A fifth aspect provides a method of treating a coronavirus infection in a subject, comprising administering to the subject an effective amount of sodium meta-arsenite ($O{=}As{-}O^{-}Na^{+}$) or potassium meta-arsenite ($O{=}As{-}O^{-}K^{+}$).

A further fifth aspect provides sodium meta-arsenite ($O{=}As{-}O^{-}Na^{+}$) or potassium meta-arsenite ($O{=}As{-}O^{-}K^{+}$) for use in treating a coronavirus infection in a subject; or use of sodium meta-arsenite ($O{=}As{-}O^{-}Na^{+}$) or potassium meta-arsenite ($O{=}As{-}O^{-}K^{+}$) in the manufacture of a medicament for treating a coronavirus infection in a subject.

A sixth aspect provides a method of reducing TNF-α, IL-1β and/or IL-6 levels in a subject suffering from an inflammatory condition due to a viral infection, comprising administering to the subject an effective amount of sodium meta-arsenite (O═As—$O^-Na^+$) or potassium meta-arsenite (O═As—$O^-K^+$).

A further sixth aspect provides sodium meta-arsenite (O═As—$O^-Na^+$) or potassium meta-arsenite (O═As—$O^-K^+$) for use in reducing TNF-α, IL-1β and/or IL-6 production in a subject suffering from an inflammatory condition due to a viral infection; or use of sodium meta-arsenite (O═As—$O^-Na^+$) or potassium meta-arsenite (O═As—$O^-K^+$) in the manufacture of a medicament for reducing TNF-α, IL-1β and/or IL-6 production in a subject suffering from an inflammatory condition due to a viral infection.

A seventh aspect provides a method of treating a coronavirus SARS-CoV-2 infection in a subject, comprising administering to the subject an effective amount of sodium meta-arsenite (O═As—$O^-Na^+$) or potassium meta-arsenite (O═As—$O^-K^+$).

A further seventh aspect provides sodium meta-arsenite (O═As—$O^-Na^+$) or potassium meta-arsenite (O═As—$O^-K^+$) for use in treating a coronavirus SARS-CoV-2 infection in a subject; or use of sodium meta-arsenite (O═As—$O^-Na^+$) or potassium meta-arsenite (O═As—$O^-K^+$) in the manufacture of a medicament for treating a coronavirus SARS-CoV-2 infection in a subject.

An eighth aspect provides a method of treating or preventing a disease or condition mediated by elevated TNF-α, IL-1β and/or IL-6 levels due to a viral infection in a subject, comprising administering to the subject an effective amount of sodium meta-arsenite (O═As—$O^-Na^+$) or potassium meta-arsenite (O═As—$O^-K^+$).

A further eighth aspect provides sodium meta-arsenite (O═As—$O^-Na^+$) or potassium meta-arsenite (O═As—$O^-K^+$) for use in treating or preventing a disease or condition mediated by elevated TNF-α, IL-1β and/or IL-6 due to a viral infection in a subject; or use of sodium meta-arsenite (O═As—$O^-Na^+$) or potassium meta-arsenite (O═As—$O^-K^+$) in the manufacture of a medicament for treating or preventing a disease or condition mediated by elevated TNF-α, IL-1β and/or IL-6 due to a viral infection in a subject.

A ninth aspect provides a pharmaceutical composition when used for reducing an inflammatory response due to a viral infection, and/or treating or preventing an inflammatory condition due to a viral infection, the composition comprising sodium meta-arsenite (O═As—$O^-Na^+$) or potassium meta-arsenite (O═As—$O^-K^+$).

A tenth aspect provides a pharmaceutical composition when used for reducing an inflammatory response due to a viral infection, and/or treating or preventing an inflammatory condition due to a viral infection, by oral administration, the composition comprising:

(a) a solid core comprising sodium meta-arsenite or potassium meta-arsenite, and one or more pharmaceutically acceptable excipients, wherein the one or more pharmaceutically acceptable excipients are selected such that oxidation of meta-arsenite to meta-arsenate is minimised;

and (b) an enteric coating comprising an enteric polymer;

wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

An eleventh aspect provides a pharmaceutical composition when used for reducing an inflammatory response due to a viral infection, and/or treating or preventing an inflammatory condition due to a viral infection, by oral administration, the composition comprising:

(a) a solid core comprising sodium meta-arsenite or potassium meta-arsenite, and the following pharmaceutically acceptable excipients:
   (i) a filler or diluent in a range of from about 5 to 95% w/w,
   (ii) a disintegrant in a range of from about 10 to 90% w/w,
   (iii) a glidant in a range of from about 0.1 to 5% w/w,
   (iv) a lubricant in a range of from about 0.1 to 5% w/w, and
   (v) optionally a binder in a range of from 0 to about 30% w/w;

and (b) an enteric coating comprising an enteric polymer;

wherein the pharmaceutically acceptable excipients are selected such that oxidation of meta-arsenite to meta-arsenate is minimised, wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

A twelfth aspect provides a method of treating a disease or a symptom caused by a viral infection in a subject, comprising administering to the subject an effective amount of sodium meta-arsenite (O═As—$O^-Na^+$) or potassium meta-arsenite (O═As—$O^-K^+$).

A further twelfth aspect provides sodium meta-arsenite (O═As—$O^-Na^+$) or potassium meta-arsenite (O═As—$O^-K^+$) for use in treating a disease or a symptom caused by a viral infection in a subject; or use of sodium meta-arsenite (O═As—$O^-Na^+$) or potassium meta-arsenite (O═As—$O^-K^+$) in the manufacture of a medicament for treating a disease or a symptom caused by a viral infection in a subject.

The present invention provides the following:

1. A method of reducing an inflammatory response due to a viral infection in a subject, comprising administering to the subject an effective amount of sodium meta-arsenite (O═As—$O^-Na^+$) or potassium meta-arsenite (O═As—$O^-K^+$).

2. The method of item 1, wherein the viral infection is a coronavirus infection.

3. The method of item 2, wherein the coronavirus is SARS-CoV-2.

4. The method of item 1, wherein the sodium meta-arsenite (O═As—$O^-Na^+$) or potassium meta-arsenite (O═As—$O^-K^+$) is administered orally.

5. The method of item 1, wherein the sodium meta-arsenite (O═As—$O^-Na^+$) or potassium meta-arsenite (O═As—$O^-K^+$) is administered at a dose in the range of from 2 mg per day to 20 mg per day.

6. A method of treating or preventing an inflammatory condition due to a viral infection in a subject, comprising administering to the subject an effective amount of sodium meta-arsenite (O═As—$O^-Na^+$) or potassium meta-arsenite (O═As—$O^-K^+$).

7. The method of item 6, wherein the viral infection is a coronavirus infection.

8. The method of item 7, wherein the coronavirus infection is caused by SARS-CoV-2.

9. The method of item 6, wherein the sodium meta-arsenite ($O{=}As{-}O^-Na^+$) or potassium meta-arsenite ($O{=}As{-}O^-K^+$) is administered orally.

10. The method of item 6, wherein the sodium meta-arsenite ($O{=}As{-}O^-Na^+$) or potassium meta-arsenite ($O{=}As{-}O^-K^+$) is administered at a dose in the range of from 2 mg per day to 20 mg per day.

11. A method of treating or preventing hypercytokinemia due to a viral infection in a subject, comprising administering to the subject an effective amount of sodium meta-arsenite ($O{=}As{-}O^-Na^+$) or potassium meta-arsenite ($O{=}As{-}O^-K^+$).

12. The method of item 11, wherein the viral infection is infection by a coronavirus.

13. The method of item 12, wherein the coronavirus is SARS-CoV-2.

14. A method of treating a viral infection in a subject, comprising administering to the subject an effective amount of sodium meta-arsenite ($O{=}As{-}O^-Na^+$) or potassium meta-arsenite ($O{=}As{-}O^-K^+$).

15. The method of item 14, wherein the viral infection is due to an infection by a coronavirus.

16. The method of item 15, wherein the coronavirus is SARS-CoV-2.

17. The method of item 14, wherein the sodium meta-arsenite ($O{=}As{-}O^-Na^+$) or potassium meta-arsenite ($O{=}As{-}O^-K^+$) is administered orally.

18. The method of item 14, wherein the sodium meta-arsenite ($O{=}As{-}O^-Na^+$) or potassium meta-arsenite ($O{=}As{-}O^-K^+$) is administered at a dose in the range of from 2 mg per day to 20 mg per day.

19. A method of treating a coronavirus infection in a subject, comprising administering to the subject an effective amount of sodium meta-arsenite ($O{=}As{-}O^-Na^+$) or potassium meta-arsenite ($O{=}As{-}O^-K^+$).

20. The method of item 19, wherein the coronavirus infection is caused by SARS-CoV-2.

21. The method of item 19, wherein the sodium meta-arsenite ($O{=}As{-}O^-Na^+$) or potassium meta-arsenite ($O{=}As{-}O^-K^+$) is administered orally.

22. The method of item 19, wherein the sodium meta-arsenite ($O{=}As{-}O^-Na^+$) or potassium meta-arsenite ($O{=}As{-}O^-K^+$) is administered at a dose in the range of from 2 mg per day to 20 mg per day.

23. A method of reducing TNF-α, IL-1β, and/or IL-6 levels in a subject suffering from an inflammatory condition due to a viral infection, comprising administering to the subject an effective amount of sodium meta-arsenite ($O{=}As{-}O^-Na^+$) or potassium meta-arsenite ($O{=}As{-}O^-K^+$).

24. The method of item 23, wherein the sodium meta-arsenite ($O{=}As{-}O^-Na^+$) or potassium meta-arsenite ($O{=}As{-}O^-K^+$) is administered orally.

25. The method of item 23, wherein the sodium meta-arsenite ($O{=}As{-}O^-Na^+$) or potassium meta-arsenite ($O{=}As{-}O^-K^+$) is administered at a dose in the range of from 2 mg per day to 20 mg per day.

26. The method of any one of items 1 to 25, wherein the sodium meta-arsenite ($O{=}As{-}O^-Na^+$) or potassium meta-arsenite ($O{=}As{-}O^-K^+$) is administered in a composition comprising:

(a) a solid core comprising sodium meta-arsenite or potassium meta-arsenite, and one or more pharmaceutically acceptable excipients, wherein the one or more pharmaceutically acceptable excipients are selected such that oxidation of meta-arsenite to meta-arsenate is minimised;

and (b) an enteric coating comprising an enteric polymer;

wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

27. The method of any one of items 1 to 25, wherein the sodium meta-arsenite ($O{=}As{-}O^-Na^+$) or potassium meta-arsenite ($O{=}As{-}O^-K^+$) is administered in a composition comprising:

(a) a solid core comprising sodium meta-arsenite or potassium meta-arsenite, and the following pharmaceutically acceptable excipients:

(i) a filler or diluent in a range of from about 5 to 95% w/w, (ii) a disintegrant in a range of from about 10 to 90% w/w, (iii) a glidant in a range of from about 0.1 to 5% w/w, (iv) a lubricant in a range of from about 0.1 to 5% w/w, and (v) optionally a binder in a range of from 0 to about 30% w/w;

and (b) an enteric coating comprising an enteric polymer;

wherein the pharmaceutically acceptable excipients are selected such that oxidation of meta-arsenite to meta-arsenate is minimised, wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

28. A pharmaceutical composition when used for reducing an inflammatory response due to a viral infection, and/or treating or preventing an inflammatory condition due to a viral infection, by oral administration, the composition comprising:

(a) a solid core comprising sodium meta-arsenite or potassium meta-arsenite, and one or more pharmaceutically acceptable excipients, wherein the one or more pharmaceutically acceptable excipients are selected such that oxidation of meta-arsenite to meta-arsenate is minimised;

and (b) an enteric coating comprising an enteric polymer;

wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

29. A pharmaceutical composition when used for reducing an inflammatory response due to a viral infection, and/or treating or preventing an inflammatory condition due to a viral infection, by oral administration, the composition comprising:

(a) a solid core comprising sodium meta-arsenite or potassium meta-arsenite, and the following pharmaceutically acceptable excipients:

(i) a filler or diluent in a range of from about 5 to 95% w/w, (ii) a disintegrant in a range of from about 10 to 90% w/w, (iii) a glidant in a range of from about 0.1 to 5% w/w, (iv) a lubricant in a range of from about 0.1 to 5% w/w, and (v) optionally a binder in a range of from 0 to about 30% w/w; and (b) an enteric coating comprising an enteric polymer;

wherein the pharmaceutically acceptable excipients are selected such that oxidation of meta-arsenite to meta-arsenate is minimised, wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

30. Use of sodium meta-arsenite ($O{=}As{-}O^-Na^+$) or potassium meta-arsenite ($O{=}As{-}O^-K^+$) in the manufacture of a medicament for reducing an inflammatory response due to a viral infection in a subject.

31. Use of sodium meta-arsenite ($O{=}As{-}O^-Na^+$) or potassium meta-arsenite ($O{=}As{-}O^-K^+$) in the manufacture of a medicament for treating or preventing an inflammatory condition due to a viral infection in a subject.

32. Use of sodium meta-arsenite ($O{=}As{-}O^-Na^+$) or potassium meta-arsenite ($O{=}As{-}O^-K^+$) in the manufacture of a medicament for treating or preventing hypercytokinemia due to a viral infection in a subject.

33. Use of sodium meta-arsenite ($O{=}As{-}O^-Na^+$) or potassium meta-arsenite ($O{=}As{-}O^-K^+$) in the manufacture of a medicament for treating a viral infection in a subject.

34. Use of sodium meta-arsenite ($O{=}As{-}O^-Na^+$) or potassium meta-arsenite ($O{=}As{-}O^-K^+$) in the manufacture of a medicament for reducing TNF-α, IL-1β, and/or IL-6 levels in a subject suffering from an inflammatory condition due to a viral infection.

35. The use of any one of items 30 to 34, wherein the viral infection is a coronavirus infection.

36. Use of sodium meta-arsenite ($O{=}As{-}O^-Na^+$) or potassium meta-arsenite ($O{=}As{-}O^-K^+$) in the manufacture of a medicament for treating a coronavirus infection in a subject.

37. The use of item 35 or 36, wherein the coronavirus infection is caused by SARS-CoV-2.

38. The use of any one of items 30 to 37, wherein the medicament is formulated for oral administration.

39. The use of any one of items 30 to 38, wherein the medicament comprises a pharmaceutical composition comprising:

(a) a solid core comprising sodium meta-arsenite ($O{=}As{-}O^-Na^+$) or potassium meta-arsenite ($O{=}As{-}O^-K^+$), and one or more pharmaceutically acceptable excipients, wherein the one or more pharmaceutically acceptable excipients are selected such that oxidation of meta-arsenite to meta-arsenate is minimised;

and (b) an enteric coating comprising an enteric polymer;

wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

40. The use of any one of items 30 to 38, wherein the medicament comprises a pharmaceutical composition comprising:

(a) a solid core comprising sodium meta-arsenite ($O{=}As{-}O^-Na^+$) or potassium meta-arsenite ($O{=}As{-}O^-K^+$), and the following pharmaceutically acceptable excipients:

(i) a filler or diluent in a range of from about 5 to 95% w/w, (ii) a disintegrant in a range of from about 10 to 90% w/w, (iii) a glidant in a range of from about 0.1 to 5% w/w, (iv) a lubricant in a range of from about 0.1 to 5% w/w, and (v) optionally a binder in a range of from 0 to about 30% w/w;

and (b) an enteric coating comprising an enteric polymer;

wherein the pharmaceutically acceptable excipients are selected such that oxidation of meta-arsenite to meta-arsenate is minimised, wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

41. A pharmaceutical composition for oral administration comprising:

(a) a solid core comprising sodium meta-arsenite or potassium meta-arsenite, and one or more pharmaceutically acceptable excipients, wherein the one or more pharmaceutically acceptable excipients are selected such that oxidation of meta-arsenite to meta-arsenate is minimised;

and (b) an enteric coating comprising an enteric polymer;

wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition;

for use in reducing an inflammatory response due to a viral infection in a subject;

for use in treating or preventing an inflammatory condition due to a viral infection in a subject;

for use in treating or preventing hypercytokinemia due to a viral infection in a subject;

for use in treating a viral infection in a subject;

for use in reducing TNF-α, IL-1β, and/or IL-6 levels in a subject suffering from an inflammatory condition due to a viral infection; or for use in treating a coronavirus infection in a subject.

42. A pharmaceutical composition for oral administration comprising:

(a) a solid core comprising sodium meta-arsenite or potassium meta-arsenite, and the following pharmaceutically acceptable excipients:

(i) a filler or diluent in a range of from about 5 to 95% w/w, (ii) a disintegrant in a range of from about 10 to 90% w/w, (iii) a glidant in a range of from about 0.1 to 5% w/w, (iv) a lubricant in a range of from about 0.1 to 5% w/w, and (v) optionally a binder in a range of from 0 to about 30% w/w;

and (b) an enteric coating comprising an enteric polymer;

wherein the pharmaceutically acceptable excipients are selected such that oxidation of meta-arsenite to meta-arsenate is minimised, wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition;

for use in reducing an inflammatory response due to a viral infection in a subject;

for use in treating or preventing an inflammatory condition due to a viral infection in a subject;

for use in treating or preventing hypercytokinemia due to a viral infection in a subject;

for use in treating a viral infection in a subject;

for use in reducing TNF-α, IL-1β, and/or IL-6 levels in a subject suffering from an inflammatory condition due to a viral infection; or for use in treating a coronavirus infection in a subject.

DETAILED DESCRIPTION OF EMBODIMENTS OF THE INVENTION

Figure 1:
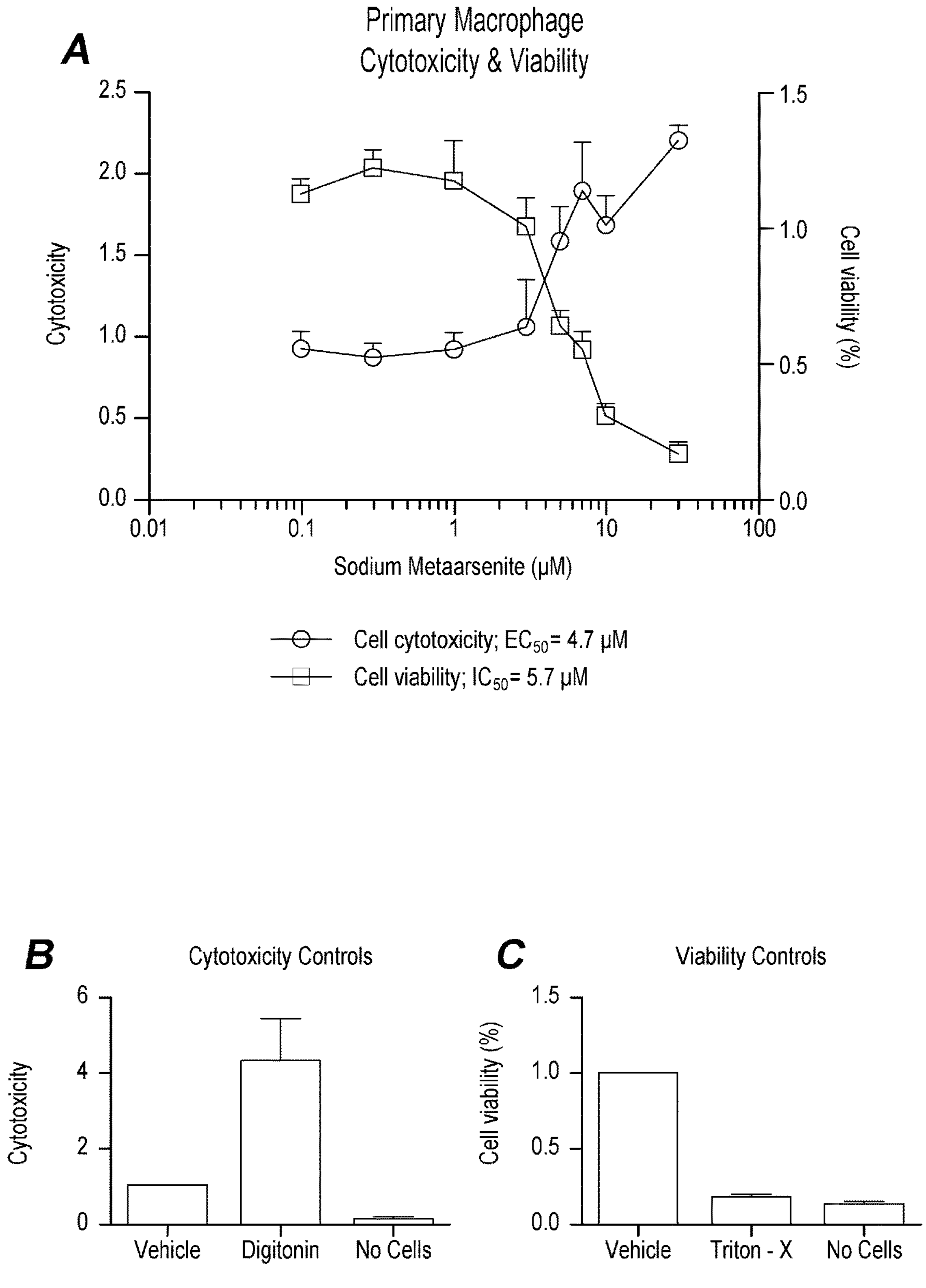
FIG. 1A to C are graphs showing the mean (±SEM) cytotoxicity and viability of cultured rat primary macrophages incubated for 24 h in culture medium containing lipopolysaccharide (LPS) at 100 ng/mL and sodium meta-arsenite (A; 30, 10, 7, 5, 3, 1, 0.3 and 0.1 μM) or controls (B and C); n=3.

Preferred embodiments of the present invention are described below by way of example only.

DEFINITIONS

Unless otherwise herein defined, the following terms will be understood to have the general meanings which follow. The terms referred to below have the general meanings which follow when the term is used alone and when the term is used in combination with other terms, unless otherwise indicated.

As used herein, "treating" means affecting a subject, tissue or cell to obtain a desired pharmacological and/or physiological effect and includes inhibiting the condition, i.e. arresting its development; or relieving or ameliorating the effects of the condition i.e., cause reversal or regression of the effects of the condition.

As used herein, "preventing" means preventing a condition from occurring in a cell, tissue or subject that may be at risk of having the condition, but does not necessarily mean that condition will not eventually develop, or that a subject will not eventually develop a condition. Preventing includes delaying the onset of a condition in a cell, tissue or subject.

As used herein, "reducing an inflammatory response due to a viral infection" means reducing the severity of an inflammatory response to a viral infection relative to the severity of the untreated inflammatory response. Reducing the severity may involve, for example, reducing the severity or number of symptoms presenting relative to the severity or number of symptoms presenting during the untreated response, or reducing the serum levels of one or more proinflammatory cytokines relative to the serum level of the one or more proinflammatory cytokines in the untreated response.

As used herein, "an inflammatory condition due to a viral infection" refers to a condition resulting from an inflammatory response to a viral infection. Typically, the inflammatory condition is caused, at least in part, by increased, and in some cases unregulated, levels of one or more proinflammatory cytokines during a viral infection. During infection by a virus, proinflammatory immune cells migrate to the site of infection and respond by secreting large amounts of proinflammatory cytokines such as TNF-α, IL-1β and IL-6, and in particular IL-1β and IL-6, in the affected area. Secretion of such proinflammatory cytokines promotes further immune cell migration to the site of infection. As a consequence of the rapid influx of immune cells, and further secretion of proinflammatory cytokines, and destruction of infected cells, fluid builds up in the affected area and tissue damage occurs. For example, coronavirus is a respiratory virus which infects the lungs of the subject. An inflammatory response to the coronavirus results in respiratory inflammation causing fluid to accumulate in the alveoli, leading to shortness of breath and pneumonia in severe cases. Over time, liquid from the inflammation hardens, and can lead to pulmonary fibrosis and in some cases death. Even in cases where the subject survives, the inflammation can result in reduced lung function.

As used herein, "reducing TNF-α, IL-1β and/or IL-6 levels" refers to reducing the amount of TNF-α, IL-1β and/or IL-6 secreted from immune cells, typically macrophage. The amount of TNF-α, IL-1β and/or IL-6 secreted from immune cells may be determine by, for example, determining serum levels of TNF-α, IL-1β and/or IL-6 in a subject.

As used herein, the term "subject" refers to a mammal. The mammal may be a human or a non-human. Examples of non-humans include primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Typically, the mammal is a human or primate. More typically, the mammal is a human.

The term "composition" encompasses compositions and formulations comprising the active pharmaceutical ingredient ("API") with excipients or carriers, and also compositions and formulations with encapsulating materials as a carrier to provide a capsule in which the active pharmaceutical ingredient (with or without other carriers) is surrounded by the encapsulation carrier. In pharmaceutical compositions, the excipient or carrier is "pharmaceutically acceptable" meaning that it is not biologically or otherwise undesirable, i.e., the material may be incorporated into a pharmaceutical composition administered to a patient without causing any undesirable biological effects or interacting in a deleterious manner with any of the other components of the composition in which it is contained. Supplementary active ingredients can also be incorporated into the compositions.

By "pharmaceutically acceptable" such as in the recitation of a "pharmaceutically acceptable salt" or a "pharmaceutically acceptable excipient or carrier" is meant herein a material that is not biologically or otherwise undesirable, i.e., the material may be incorporated into a pharmaceutical composition administered to a patient without causing any undesirable biological effects or interacting in a deleterious manner with any of the other components of the composition in which it is contained.

The term "effective amount" or "therapeutically effective amount" refers to the quantity of an active pharmaceutical ingredient that is sufficient to yield a desired therapeutic response without undue adverse side effects (such as toxicity, irritation, or allergic response) commensurate with a reasonable benefit/risk ratio when used in the manner of this invention. This amount for example could be effective in reducing TNF-α, IL-1β and/or IL-6 production by immune cells, more typically macrophage, of the subject. The specific effective amount or therapeutically effective amount will vary with such factors as the particular condition being treated, the age, body weight, general health, physical condition, gender and diet of the subject, the duration of the treatment, the nature of concurrent therapy (if any), and the severity of the particular condition.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

As used herein, "administration" or "administer" or "administering" refers to dispensing, applying, or tendering two or more agents (for example sodium meta-arsenite and/or arsenic trioxide and cisplatin, adriamycin and/or taxane, e.g., paclitaxel or docetaxel) to a subject. Administration can be performed using any of a number of methods known in the art. For example, "administering" as used herein is meant via infusion (intravenous administration (i.v.)), parenteral and/or oral administration. By "parenteral" is meant intravenous, subcutaneous and intramuscular administration. It will be appreciated that the actual preferred method and order of administration will vary according to, inter alia, the particular formulation of SMA or KMA being utilized. The method and order of administration of SMA or KMA for a given set of conditions can be ascertained by those skilled in the art using conventional techniques and in view of the information set out herein.

As used herein, the term "about" means a slight variation of the value specified, preferably within 10 percent of the value specified. Nevertheless, the term "about" can mean a higher tolerance of variation depending on for instance the experimental technique used. Said variations of a specified value are understood by the skilled person and are within the context of the present invention. Further, to provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

Unless otherwise stated, all amounts are expressed herein as percentage by weight (% w/w).

Of course, any material used in preparing the pharmaceutical compositions described herein should be pharmaceutically pure and substantially non-toxic in the amounts employed.

Inflammatory Response

One aspect provides a method of reducing an inflammatory response due to a viral infection in a subject, comprising administering to the subject an effective amount of sodium meta-arsenite ($O{=}As{-}O^{-}Na^{+}$) or potassium meta-arsenite ($O{=}As{-}O^{-}K^{+}$).

An inflammatory response due to a viral infection is an immune response to a viral infection in which proinflammatory cytokines are secreted by immune cells, typically macrophage, in response to the viral infection. In one embodiment, the proinflammatory cytokines comprise TNF-α, IL-1β, and/or IL-6. In some embodiments, the inflammatory response includes hypercytokinemia (also known as "cytokine storm").

The inflammatory response due to a viral infection may be either acute or chronic. Acute inflammation typically lasts only a few days. In contrast, chronic inflammation typically lasts weeks, months or even indefinitely, and may cause tissue damage.

One aspect provides a method of treating or preventing an inflammatory condition due to a viral infection in a subject, comprising administering to the subject an effective amount of sodium meta-arsenite ($O{=}As{-}O^{-}Na^{+}$) or potassium meta-arsenite ($O{=}As{-}O^{-}K^{+}$). An inflammatory condition due to a viral infection is a condition resulting from an inflammatory response due to a viral infection.

In one embodiment, the inflammatory condition is systemic inflammatory response syndrome (SIRS) due to a viral infection. In one embodiment, the viral infection is due to an RNA virus.

In one embodiment, the inflammatory condition is due to an influenza infection. In one embodiment, the influenza is avian influenza. In one embodiment, the inflammatory condition due to an influenza infection is pneumonia.

In one embodiment, the inflammatory condition is due to a coronavirus infection. In one embodiment, the coronavirus is selected from the group consisting of 229E, NL63, OC43, HKU1, MERS-CoV, SARS-CoV, and SARS-CoV-2. In one embodiment, the coronavirus is MERS-CoV. In one embodiment, the coronavirus is SARS-CoV. In one embodiment, the coronavirus is SARS-CoV-2 (also known as "2019 novel coronavirus").

In various embodiments, the inflammatory condition is selected from Middle East Respiratory Syndrome (MERS—caused by MERS-CoV), and severe acute respiratory syndrome (SARS caused by SARS-CoV) or a condition (e.g. COVID-19) caused by 2019 novel coronavirus (SARS-CoV-2).

In one embodiment, the inflammatory condition is pneumonia caused by COVID-19.

The methods described herein involve the administration of an effective amount of sodium meta-arsenite ($O{=}As{-}O^{-}Na^{+}$) or potassium meta-arsenite ($O{=}As{-}O^{-}K^{+}$).

As described in the Examples, the inventor has found that sodium meta-arsenite is capable of reducing or inhibiting production and/or secretion of the proinflammatory cytokines TNF-α, IL-1, and/or IL-6 from macrophage.

One aspect provides a method of reducing TNF-α, IL-1β and/or IL-6 levels, typically serum levels, in a subject suffering from an inflammatory condition due to a viral infection, comprising administering to the subject an effective amount of sodium meta-arsenite ($O{=}As{-}O^{-}Na^{+}$) or potassium meta-arsenite ($O{=}As{-}O^{-}K^{+}$).

In one embodiment, the method reduces TNF-α levels in the subject. Typically, the method reduces TNF-α serum levels in the subject.

In one embodiment, the method reduces IL-1β levels in the subject. Typically, the method reduces IL-1β serum levels in the subject.

In one embodiment, the method reduces TNF-α and IL-1β levels in the subject. Typically, the method reduces TNF-α and IL-1β serum levels in the subject.

In one embodiment, the method reduces IL-6 levels in the subject. Typically, the method reduces IL-6 serum levels in the subject.

In one embodiment, the method reduces IL-1β and IL-6 levels in the subject. Typically, the method reduces IL-1β and IL-6 serum levels in the subject.

In one embodiment, the method reduces TNF-α, IL-1β and IL-6 levels in the subject. Typically, the method reduces TNF-α, IL-1β and IL-6 serum levels in the subject.

One aspect provides a method of treating or preventing a disease or condition mediated by elevated TNF-α, IL-1β and/or IL-6 levels due to a viral infection in a subject, comprising administering to the subject an effective amount of sodium meta-arsenite ($O{=}As{-}O^{-}Na^{+}$) or potassium meta-arsenite ($O{=}As{-}O^{-}K^{+}$).

In one embodiment, the disease or condition is pneumonia. In one embodiment, the viral infection is a coronavirus infection. In one embodiment, the coronavirus is SARS-CoV-2.

In one embodiment, the disease or condition is MERS or SARS.

In one embodiment, the disease or condition is hypercytokinemia. In one embodiment, the viral infection is a coronavirus infection. In one embodiment, the coronavirus is SARS-CoV-2.

One aspect provides a method of treating a disease or a symptom caused by a viral infection in a subject, comprising administering to the subject an effective amount of sodium meta-arsenite ($O{=}As{-}O^{-}Na^{+}$) or potassium meta-arsenite ($O{=}As{-}O^{-}K^{+}$).

In one embodiment, the disease or symptom is an illness such as fever, chills, flu-like symptoms, inflammation or brain fog, or a combination thereof. Thus, in one embodiment, the disease or symptom is fever. In another embodiment, the disease or symptom is chills. In another embodiment, the disease or symptom is flu-like symptoms. In another embodiment, the disease or symptom is inflammation. In another embodiment, the disease or symptom is brain fog.

Flu-like symptoms include headache, fever, cough, shortness of breath (dyspnea), breathing difficulty, sputum development, chest tightness, fatigue, sore throat, runny nose, loss of appetite, and pain (including muscle pain and body aches).

In one embodiment, the viral infection is a coronavirus infection. In one embodiment, the coronavirus is SARS-CoV-2.

In one embodiment, the disease or symptom is treated by sodium meta-arsenite (O═As—$O^-Na^+$) or potassium meta-arsenite (O═As—$O^-K^+$) through an anti-inflammatory mechanism and/or through suppression of viral replication. In one embodiment, the disease or symptom is treated by sodium meta-arsenite (O═As—$O^-Na^+$) or potassium meta-arsenite (O═As—$O^-K^+$) through an anti-inflammatory mechanism. In one embodiment, the disease or symptom is treated by sodium meta-arsenite (O═As—$O^-Na^+$) or potassium meta-arsenite (O═As—$O^-K^+$) through suppression of viral replication. In one embodiment, the disease or symptom is treated by sodium meta-arsenite (O═As—$O^-Na^+$) or potassium meta-arsenite (O═As—$O^-K^+$) through an anti-inflammatory mechanism and suppression of viral replication.

Typically, the sodium meta-arsenite (O═As—$O^-Na^+$) or potassium meta-arsenite (O═As—$O^-K^+$) is administered in the form of a pharmaceutical composition comprising sodium meta-arsenite (O═As—$O^-Na^+$) or potassium meta-arsenite (O═As—$O^-K^+$), and a pharmaceutically acceptable carrier.

In some embodiments, the carrier is a non-naturally occurring carrier.

Pharmaceutical Compositions

As described above, typically, the sodium meta-arsenite (O═As—$O^-Na^+$) or potassium meta-arsenite (O═As—$O^-K^+$) used in the methods and uses described herein is administered in the form of a pharmaceutical composition comprising sodium meta-arsenite (O═As—$O^-Na^+$) or potassium meta-arsenite (O═As—$O^-K^+$), and a pharmaceutically acceptable carrier.

The pharmaceutical compositions may contain other agents or further active agents as described above, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: The Science and Practice of Pharmacy, 21st Ed., 2005, Lippincott Williams & Wilkins).

The pharmaceutical composition may be suitable for intravenous, oral, nasal, topical (including dermal, buccal and sub-lingual), or parenteral (including intramuscular, subcutaneous and intravenous) administration or in a form suitable for administration by inhalation or insufflation.

The compounds described herein, together with a pharmaceutically acceptable carrier, may thus be placed into the form of pharmaceutical compositions and unit dosages thereof. The pharmaceutical composition may be a solid, such as a tablet or filled capsule, or a liquid such as solution, suspension, emulsion, elixir, or capsule filled with the same, for oral administration. The pharmaceutical composition may be a liquid such as solution, suspension, or emulsion, for intravitreal administration.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the compounds described herein, pharmaceutically acceptable carriers can be either solid or liquid. Solid form preparations include powders, tablets, pills, capsules, cachets, lozenges (solid or chewable), suppositories, and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Tablets, powders, capsules, pills, cachets, and lozenges can be used as solid forms suitable for oral administration.

Liquid form preparations include solutions, suspensions, and emulsions, for example, water or water-propylene glycol solutions. For example, parenteral injection liquid preparations can be formulated as solutions in saline, water or aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

In one embodiment, the sodium meta-arsenite and potassium meta-arsenite are formulated for oral administration. The composition for oral administration may be a solid or liquid preparation.

In one embodiment, the composition for oral administration is a solid preparation.

Sodium meta-arsenite and potassium meta-arsenite can be synthesised from arsenic trioxide ($As_2O_3$). For example, sodium meta-arsenite can be synthesised by reacting arsenic trioxide ($As_2O_3$) with aqueous sodium hydroxide to form trivalent sodium meta-arsenite (top left of Scheme 1 below). The solution is cooled, the sodium meta-arsenite filtered, and the water evaporated. The sodium meta-arsenite formed is then washed with methanol to remove water, filtered under vacuum, and then dried. Potassium meta-arsenite may be prepared in a similar manner to sodium meta-arsenite using aqueous potassium hydroxide instead of aqueous sodium hydroxide.

However, a major complication of the meta-arsenite salt (salt of O═As—$O^-$) is its speciation chemistry and its ability to convert to a number of different forms in solution, such as when an oral dosage form comprising sodium meta-arsenite (O═As—$O^-Na^+$) or potassium meta-arsenite (O═As—$O^-K^+$) dissolves in the stomach. For example, sodium meta-arsenite (O═As—$O^-Na^+$) is readily soluble in strong acid, in strong base, and in neutral conditions. The forms present are dependent on the pH of the solution and sodium meta-arsenite's propensity to oxidise (Scheme 1 below). Potassium meta-arsenite behaves in a similar manner to sodium meta-arsenite. In general, neutral to alkaline conditions tend to favour the formation (or retention) of As(III) (arsenite) while acidic conditions (especially in the presence of chloride ions, such as in the stomach) tend to favour the formation of As(V) (arsenate).

Scheme 1

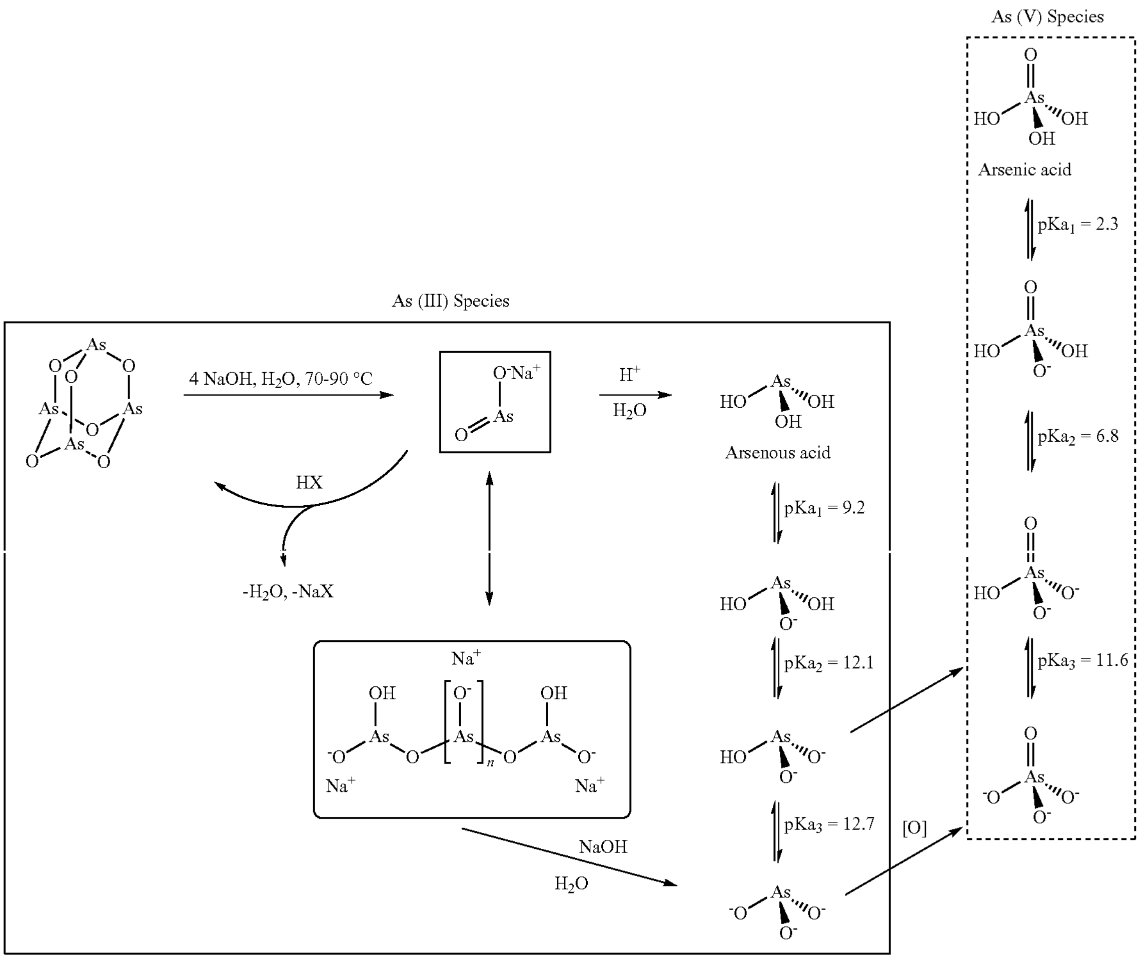

In addition, meta-arsenite (O═As—O⁻) can oxidise to meta-arsenate during storage when chloride, metal ions or moisture (e.g. within dissolution media or within excipients; excipients may catalyse oxidation, e.g. excipients with metal ions, in particular, iron), or atmospheric oxygen, is present. Oxidation of meta-arsenite can occur quite rapidly at low pH. Sodium meta-arsenite ($O{=}As{-}O^-Na^+$) and potassium meta-arsenite ($O{=}As{-}O^-K^+$) are both hygroscopic.

In solution, the main degradant of sodium meta-arsenite is the pentavalent sodium meta-arsenate ($AsO_4^{3-}$ or As(V)) species formed by an oxidation reaction. It is hypothesised that this may proceed as shown below in Box 1, however in theory, oxidation (a change in valency) could occur without absorption of oxygen occurring (e.g. by interaction with an excipient or a reaction with metal ions present within the sodium meta-arsenite or compositions).

Box 1

| Reduced form | Oxidised form | | |
|---|---|---|---|
| $As^{3+}$ | $As^{5+} + 2e^-$ | change in As valency | (Equation 1) |
| $AsO_2^- + O_2$ | $AsO_4^{3-}$ | absorption of oxygen | (Equation 2) |

A further complication arising from the dissolution of sodium meta-arsenite ($O{=}As{-}O^-Na^+$) or potassium meta-arsenite ($O{=}As{-}O^-K^+$) in the stomach is the formation of arsenic(III) chloride ($AsCl_3$) from the chloride ions in the stomach. Oxidation of meta-arsenite may occur more rapidly when chloride is present. Arsenic(III) chloride is toxic to humans and causes serious adverse effects.

In some embodiment in which the composition is for oral administration, there is provided an enteric coated solid pharmaceutical composition comprising sodium meta-arsenite or potassium meta-arsenite, which is suitable for oral administration, and which passes through the stomach and commences dissolution in the small intestines (where acidity is between pH 6.5-7.5). The risk of oxidation of the meta-arsenite form to the meta-arsenate form (in the stomach or during storage), and the risk of formation of toxic arsenic (III) chloride from the chloride ions in the stomach, are minimised by employing suitable excipients and carriers, and a suitable enteric coating of a suitable thickness. The dissolution of the enteric-coated solid pharmaceutical composition in the small intestines can occur rapidly or occur over an extended period of time (e.g. 0.5, 0.75, 1, 2, 3, 4, 5 or 6 hours, preferably within 2 hours).

Preferred embodiments of the pharmaceutical composition for oral administration are described below. The pharmaceutical composition for oral administration may be manufactured through effective methods as described below.

Pharmaceutical Composition for Oral Administration

In one embodiment, the pharmaceutical composition suitable for oral administration comprises:

(a) a solid core comprising sodium meta-arsenite or potassium meta-arsenite, and one or more pharmaceutically acceptable excipients, wherein the one or more pharmaceutically acceptable excipients are selected such that oxidation of meta-arsenite to meta-arsenate is minimised;

and (b) an enteric coating comprising an enteric polymer;

wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

For example, in the above embodiment, the one or more pharmaceutically acceptable excipients may be selected from a filler or diluent, a disintegrant, a glidant, a lubricant, and a binder. In some embodiments, the solid core may comprise two or more of these excipients, three or more of these excipients, four or more of these excipients, or all of these excipients.

Thus, in some embodiments, the solid core comprises a filler or diluent, a disintegrant, a glidant, a lubricant, and a binder.

In one embodiment, the pharmaceutical composition suitable for oral administration comprises:

(a) a solid core comprising sodium meta-arsenite or potassium meta-arsenite, and the following pharmaceutically acceptable excipients:
   (i) a filler or diluent in a range of from about 5 to 95% w/w,
   (ii) a disintegrant in a range of from about 10 to 90% w/w,
   (iii) a glidant in a range of from about 0.1 to 5% w/w,
   (iv) a lubricant in a range of from about 0.1 to 5% w/w, and
   (v) optionally a binder in a range of from 0 to about 30% w/w;

and (b) an enteric coating comprising an enteric polymer;

wherein the pharmaceutically acceptable excipients are selected such that oxidation of meta-arsenite to meta-arsenate is minimised, wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

The pharmaceutical composition may be in the form of an enteric coated tablet or an enteric coated capsule. In some embodiments, the pharmaceutical composition is an enteric coated tablet. In some embodiments, the pharmaceutical composition is an enteric coated capsule.

In the pharmaceutical composition, the active pharmaceutical ingredient (API) is sodium meta-arsenite or potassium meta-arsenite.

Sodium meta-arsenite and potassium meta-arsenite can be obtained commercially in high purity (>98% As(III) and minimal levels of As(V)). Sodium meta-arsenite and potassium meta-arsenite are hygroscopic.

Being inorganic compounds, each of sodium meta-arsenite and potassium meta-arsenite has a higher particle (true) density (e.g. approximately 2.1 to 2.3 g/cm$^3$ for sodium meta-arsenite, and about 8.76 g/cm$^3$ for potassium meta-arsenite) compared with typical tablet excipients (typical tablet excipients are usually organic substances which would have a density of approximately 1.2 to 1.6 g/cm$^3$).

The potential for segregation of the API in compositions is high when there are differences in the particle size of the API and the particle size of the excipients. It will be appreciated by a person skilled in the art that using the preferred particle size of the API advantageously leads to improved powder mixing and blend uniformity, minimises or eliminates segregation in powders on compression, and achieves satisfactory content uniformity in the compositions.

In some embodiments of the composition for oral administration, the particle size of the API is about 50 to 150 microns. In some embodiments, the particle size of the API is about 70 to 120 microns. In some embodiments, the particle size of the API is about 90 to 100 microns.

In some embodiments, the API is sodium meta-arsenite.

In some embodiments, the API is potassium meta-arsenite.

In some embodiments, the amount of API in the solid core of the pharmaceutical composition for oral administration is about 0.1 to 5.0% w/w of the solid core, preferably about 0.5 to 3.0% w/w of the solid core, more preferably about 1.0 to 2.5% w/w of the solid core, even more preferably about 1.5 to 2.0% w/w of the solid core, and most preferably about 1.6 to 1.8% w/w of the solid core, e.g. about 1.65% w/w, about 1.66% w/w, about 1.67% w/w, about 1.68% w/w, about 1.69% w/w, about 1.70% w/w, about 1.71% w/w, about 1.72% w/w, about 1.73% w/w, about 1.74% w/w, or about 1.75% w/w of the solid core.

In some embodiments, the particle size of the API and the particle sizes of the pharmaceutically acceptable excipients are similar. Advantageously, the use of an API and excipients with similar particle sizes can lead to improved powder mixing and blend uniformity, can minimise or eliminate segregation in powders on compression, and can achieve satisfactory content uniformity in the compositions.

In some embodiments, the API is micronised. It will be appreciated by a person skilled in the art that reducing the API particle size by micronisation may improve blend uniformity and content uniformity in dosage forms (such as tablets) when the API is present at low levels.

In some embodiments, the API is not micronised. It will be appreciated by a person skilled in the art that micronising a hygroscopic API (such as sodium meta-arsenite and potassium meta-arsenite) may lead to an increased risk of decomposition due to higher surface area and reactivity.

In one embodiment, in addition to sodium meta-arsenite or potassium meta-arsenite, the pharmaceutical composition for oral administration comprises one or more pharmaceutically acceptable excipients which are selected such that oxidation of meta-arsenite to meta-arsenate is minimised.

In some embodiments, the pharmaceutically acceptable excipients are selected such that less than about 10% w/w, preferably less than about 5% w/w, more preferably less than about 2% w/w, even more preferably less than about 1% w/w, and most preferably less than about 0.5% w/w of sodium meta-arsenite or potassium meta-arsenite is oxidised to sodium meta-arsenate or potassium meta-arsenate after storage at room temperature for at least about 1 month, preferably at least about 2 months, more preferably at least about 3 months, even more preferably at least about 4 months, and most preferably at least about 6 months.

In another embodiment, in addition to sodium meta-arsenite or potassium meta-arsenite, the pharmaceutical composition for oral administration comprises the following pharmaceutically acceptable excipients:

(i) a filler or diluent,
(ii) a disintegrant,
(iii) a glidant,
(iv) a lubricant, and
(v) optionally a binder.

It will be appreciated by persons skilled in the art that some excipients have multiple functions. Where an excipient included in the pharmaceutical composition has multiple functions, it is considered that the pharmaceutical composition includes excipients with those functions, e.g. if an excipient acts as both a binder and a disintegrant, it is understood that the pharmaceutical composition comprises a binder and a disintegrant.

Generally, the one or more pharmaceutically acceptable excipients are compatible with the sodium or potassium meta-arsenite. Preferably, the pharmaceutically acceptable excipients have low moisture levels or low water activity in order to minimise the possibility of oxidation of the meta-arsenite to meta-arsenate. Thus, preferably, the pharmaceutical composition for oral administration does not contain excipients with high moisture levels or high water activity (such excipients may catalyse oxidation, e.g. excipients with metal ions, in particular, iron). However, it will be appreciated by persons skilled in the art that there is a limit to the practicability of this for the pharmaceutical composition for oral administration since some available moisture is necessary for satisfactory compression.

In some embodiments, the particle size of the API and the particle sizes of the pharmaceutically acceptable excipients are similar. Advantageously, the use of an API and excipients with similar particle sizes can lead to improved powder mixing and blend uniformity, can minimise or eliminate segregation in powders on compression, and can achieve satisfactory content uniformity in the solid core.

In some embodiments, where possible, higher density versions of major excipients are selected in an effort to match the density of sodium or potassium meta-arsenite (sodium meta-arsenite has an estimated true density of approximately 2.1 to 2.3 g/cm$^3$, and potassium meta-arsenite has an estimated true density of approximately 8.76 g/cm$^3$); typical tablet excipients being organic substances have a density of approximately 1.2 to 1.6 g/cm$^3$.

The filler or diluent may, for example, be selected from dibasic calcium phosphate anhydrous, partially pregelatinised starch, silicified microcrystalline cellulose, microcrystalline cellulose, calcium sulphate dihydrate, lactose, calcium hydrogen phosphate, calcium carbonate, sodium carbonate, calcium phosphate, sodium phosphate, or a mixture thereof. In some embodiments, the filler or diluent is dibasic calcium phosphate anhydrous, partially pregelatinised starch, or a mixture thereof. In some embodiments, the filler or diluent is dibasic calcium phosphate anhydrous. In some embodiments, the filler or diluent is partially pregelatinised starch. In some embodiments, the diluent may be a compressible diluent, e.g. silicified microcrystalline cellulose, microcrystalline cellulose, or partially pregelatinised starch.

The filler or diluent may be present in the solid core of the pharmaceutical composition for oral administration in an amount of from about 5 to 95% w/w of the solid core. In some embodiments, the filler or diluent is present in the solid core of the pharmaceutical composition in an amount of from about 10 to 90% w/w of the solid core, e.g. about 10% w/w of the solid core, about 15% w/w of the solid core, about 20% w/w of the solid core, about 25% w/w of the solid core, about 30% w/w of the solid core, about 35% w/w of the solid core, about 40% w/w of the solid core, about 45% w/w of the solid core, about 50% w/w of the solid core, about 55% w/w of the solid core, about 60% w/w of the solid core, about 65% w/w of the solid core, about 70% w/w of the solid core, about 75% w/w of the solid core, about 80% w/w of the solid core, about 85% w/w of the solid core, or about 90% w/w of the solid core.

The disintegrant may, for example, be selected from L-hydroxypropyl cellulose, partially pregelatinised starch, crospovidone, potato starch, corn starch, sodium starch glycolate, and alginic acid. Sodium starch glycolate and crospovidone are super disintegrants. In some embodiments, the disintegrant is L-hydroxypropyl cellulose, partially pregelatinised starch, sodium starch glycolate, or a mixture of two or more thereof. In some embodiments, the disintegrant is L-hydroxypropyl cellulose. In some embodiments, the disintegrant is partially pregelatinised starch. In some embodiments, the disintegrant is sodium starch glycolate.

The disintegrant may be present in the solid core of the pharmaceutical composition for oral administration in an amount of from about 10 to 90% w/w of the solid core, e.g. about 10 to 50% w/w of the solid core. In some embodiments, the disintegrant is present in the solid core of the pharmaceutical composition for oral administration in an amount of from about 15 to 85% w/w of the solid core, e.g. about 15% w/w of the solid core, about 20% w/w of the solid core, about 25% w/w of the solid core, about 30% w/w of the solid core, about 35% w/w of the solid core, about 40% w/w of the solid core, about 45% w/w of the solid core, about 50% w/w of the solid core, about 55% w/w of the solid core, about 60% w/w of the solid core, about 65% w/w of the solid core, about 70% w/w of the solid core, about 75% w/w of the solid core, about 80% w/w of the solid core, or about 85% w/w of the solid core.

The glidant may, for example, be selected from colloidal silicon dioxide and talc. In some embodiments, the glidant is colloidal silicon dioxide. In some embodiments, the glidant is talc.

The glidant may be present in the solid core of the pharmaceutical composition for oral administration in an amount of from about 0.1 to 5% w/w of the solid core. In some embodiments, the glidant is present in the solid core of the pharmaceutical composition for oral administration in an amount of from about 0.3 to 4% w/w of the solid core, e.g. about 0.3% w/w of the solid core, about 0.4% w/w of the solid core, about 0.5% w/w of the solid core, about 0.6% w/w of the solid core, about 0.7% w/w of the solid core, about 0.8% w/w of the solid core, about 0.9% w/w of the solid core, about 1.0% w/w of the solid core, about 1.1% w/w of the solid core, about 1.2% w/w of the solid core, about 1.3% w/w of the solid core, about 1.4% w/w of the solid core, about 1.5% w/w of the solid core, about 1.6% w/w of the solid core, about 1.7% w/w of the solid core, about 1.8% w/w of the solid core, about 1.9% w/w of the solid core, about 2.0% w/w of the solid core, about 2.1% w/w of the solid core, about 2.2% w/w of the solid core, about 2.3% w/w of the solid core, about 2.4% w/w of the solid core, about 2.5% w/w of the solid core, about 2.6% w/w of the solid core, about 2.7% w/w of the solid core, about 2.8% w/w of the solid core, about 2.9% w/w of the solid core, about 3.0% w/w of the solid core, about 3.1% w/w of the solid core, about 3.2% w/w of the solid core, about 3.3% w/w of the solid core, about 3.4% w/w of the solid core, about 3.5% w/w of the solid core, about 3.6% w/w of the solid core, about 3.7% w/w of the solid core, about 3.8% w/w of the solid core, about 3.9% w/w of the solid core, or about 4.0% w/w of the solid core.

The lubricant may, for example, be selected from sodium stearyl fumarate, magnesium stearate, stearic acid, talc, and silica. In some embodiments, the lubricant is sodium stearyl fumarate. In some embodiments, the lubricant is magnesium stearate. In some embodiments, the lubricant is stearic acid. In some embodiments, the lubricant is talc. In some embodiments, the lubricant is silica.

The lubricant may be present in the solid core of the pharmaceutical composition for oral administration in an amount of from about 0.1 to 5% w/w of the solid core. In some embodiments, the lubricant is present in the solid core of the pharmaceutical composition for oral administration in an amount of from about 0.3 to 4% w/w of the solid core, e.g. about 0.3% w/w of the solid core, about 0.4% w/w of the solid core, about 0.5% w/w of the solid core, about 0.6% w/w of the solid core, about 0.7% w/w of the solid core, about 0.8% w/w of the solid core, about 0.9% w/w of the solid core, about 1.0% w/w of the solid core, about 1.1% w/w of the solid core, about 1.2% w/w of the solid core, about 1.3% w/w of the solid core, about 1.4% w/w of the solid core, about 1.5% w/w of the solid core, about 1.6% w/w of the solid core, about 1.7% w/w of the solid core, about 1.8% w/w of the solid core, about 1.9% w/w of the solid core, about 2.0% w/w of the solid core, about 2.1% w/w of the solid core, about 2.2% w/w of the solid core, about 2.3% w/w of the solid core, about 2.4% w/w of the solid core, about 2.5% w/w of the solid core, about 2.6% w/w of the solid core, about 2.7% w/w of the solid core, about 2.8% w/w of the solid core, about 2.9% w/w of the solid core, about 3.0% w/w of the solid core, about 3.1% w/w of the solid core, about 3.2% w/w of the solid core, about 3.3% w/w of the solid core, about 3.4% w/w of the solid core, about 3.5% w/w of the solid core, about 3.6% w/w of the solid core, about 3.7% w/w of the solid core, about 3.8% w/w of the solid core, about 3.9% w/w of the solid core, or about 4.0% w/w of the solid core.

If present, the binder may, for example, be selected from silicified microcrystalline cellulose, microcrystalline cellulose, partially pregelatinised starch, L-hydroxypropyl cellulose (low substituted hydroxypropylcellulose), hydroxypropyl cellulose, copovidone (polyvinylpyrrolidone), pregelatinised maize starch, hydroxypropylmethylcellulose, starch, acacia, corn starch, and gelatin. In some embodiments, the binder is L-hydroxypropyl cellulose (low substituted hydroxypropylcellulose). In some embodiments, the binder is a mixture of L-hydroxypropyl cellulose (low substituted hydroxypropylcellulose) and hydroxypropyl cellulose. In some embodiments, the binder is partially pregelatinised starch.

The binder may be present in the solid core of the pharmaceutical composition for oral administration in an amount of from about 0 to 30% w/w of the solid core. In some embodiments, the binder is present in the solid core of the pharmaceutical composition for oral administration in an amount of from about 1 to 30% w/w of the solid core, e.g. about 5 to 25% w/w of the solid core. For example, the binder may be present in the solid core of the pharmaceutical composition in an amount of about 5% w/w of the solid core, about 10% w/w of the solid core, about 15% w/w of the solid core, about 20% w/w of the solid core, about 25% w/w of the solid core, about 30% w/w of the solid core.

The pharmaceutical composition for oral administration may optionally comprise an antioxidant in the solid core. Antioxidants function as reducing agents by: (a) lowering redox potential, (b) scavenging oxygen, or (c) by terminating free radical reactions (acting as free radical inhibitors). Mechanisms (a) and (b) are most relevant to the degradation of sodium or potassium meta-arsenite to sodium or potassium meta-arsenate. Advantageously, the antioxidant acts to reduce or prevent the oxidation of As(III) to As(V) in the composition.

Examples of antioxidants that may be used in the solid core include: sodium sulphite, sodium bisulphite, sodium metabisulphite, sodium sulphate, sodium thiosulphate, cysteine hydrochloride, ascorbic acid, propyl gallate, butylated hydroxytoluene (BHT), and butylated hydroxyanisole (BHA).

The antioxidant may be present in the solid core in an amount of from about 0.01 to 0.2% w/w, e.g. 0.01% w/w, 0.02% w/w, 0.03% w/w, 0.04% w/w, 0.05% w/w, 0.06% w/w, 0.07% w/w, 0.08% w/w, 0.09% w/w, 0.10% w/w, 0.11% w/w, 0.12% w/w, 0.13% w/w, 0.14% w/w, 0.15% w/w, 0.16% w/w, 0.17% w/w, 0.18% w/w, 0.19% w/w, or 0.20% w/w of the solid core.

It will be appreciated that a person skilled in the art would understand that the amounts of the API (sodium meta-arsenite or potassium meta-arsenite), excipients and other ingredients in the solid core are adjusted to make up 100% of the solid core.

Advantageously, the solid core of the pharmaceutical composition for oral administration has good blend uniformity and content uniformity due to the use of suitable excipients as described above.

In some embodiments, the solid core of the pharmaceutical composition for oral administration does not comprise any one or more of the following: silicified microcrystalline cellulose, microcrystalline cellulose, calcium sulphate dihydrate, copovidone (polyvinylpyrrolidone), crospovidone, stearic acid, talc, and sodium metabisulphite.

The pharmaceutical composition for oral administration may include an enteric coating comprising an enteric polymer. The enteric coating may be applied by using suitable coating techniques known in the art. The enteric coating material may be dispersed or dissolved in either water or in suitable organic solvents.

As enteric coating polymers, one or more, separately or in combination, of the following may, for example, be used: solutions or dispersions of copolymers of acrylic acids and their esters or methacrylic acids or their esters, polysorbates, cellulose acetate phthalate polymers, hydroxypropyl methylcellulose phthalate polymers, hydroxypropyl methylcellulose acetate succinate, polyvinyl acetate phthalate, cellulose acetate trimellitate, carboxymethylethylcellulose, shellac, or other suitable enteric coating polymer(s).

In some embodiments, the enteric coating is a methacrylate-based coating, for example, comprising a copolymer of methacrylic acid and ethyl acrylate. Several useful products are commercially available.

Enteric coating polymer products are available from Rohm GmbH & Co., Darmstadt, Germany under the trade mark EUDRAGIT® including L100, L100-55 and S100. Examples of useful EUDRAGIT® products include EUDRAGIT L100-55, EUDRAGIT S100, and EUDRAGIT L30D-55. EUDRAGIT L100-55 is poly(methacrylic acid-co-ethyl acrylate) (1:1). EUDRAGIT S100 is methacrylic acid-methyl methacrylate copolymer (1:2). EUDRAGIT L30D-55 is an aqueous dispersion of a pH dependent polymer soluble at or above pH 5.5 for targeted delivery in the duodenum. The methacrylic acid copolymer EUDRAGIT L30D-55 is a copolymer of methacrylic acid and ethyl acrylate in a 1:1 ratio and has the formula $(C_5H_2O_2 \cdot C_4H_6O_2)_x$.

Acryl-EZE® from Colorcon is an aqueous acrylic enteric system, is dispersible in water, for the application of an enteric film coating to solid dosage forms such as tablets, granules and beads. Examples of useful Acryl-EZE® products include Acryl-EZE II white (493Z180022) and Acryl-EZE Green (93011863).

The enteric coating may further contain pharmaceutically acceptable plasticizers to obtain the desired mechanical properties, such as flexibility and hardness of the enteric coating. Such plasticizers are, for example, but not restricted to, triacetin, citric acid esters, phthalic acid esters, dibutyl sebacate, cetyl alcohol, polyethylene glycols, polysorbates or other plasticizers. Anti-tacking agents such as, for example, magnesium stearate, titanium dioxide, talc, and other additives may also be included in the enteric coating.

In some embodiments, the enteric coating provides a weight gain of about 7 to 17% w/w of the solid core, e.g. a weight gain of about 8 to 14% w/w of the solid core. In some embodiments, the enteric coating provides a weight gain of about 8% w/w, a weight gain of about 8.5% w/w, a weight gain of about 9% w/w, a weight gain of about 9.5% w/w, a weight gain of about 10% w/w, a weight gain of about 10.5% w/w, a weight gain of about 11% w/w, a weight gain of about 11.5% w/w, a weight gain of about 12% w/w, a weight gain of about 12.5% w/w, a weight gain of about 13% w/w, a weight gain of about 13.5% w/w, or a weight gain of about 14% w/w. In some embodiments, the enteric coating provides a weight gain of about 12% w/w of the solid core.

In some embodiments, the solid core may be sub-coated prior to coating with an enteric coating, using polymers known in the art for being suitable for sub-coating.

The pharmaceutical composition for oral administration is in one embodiment, solid, enteric coated, and suitable for oral administration, e.g. enteric coated tablets or enteric coated capsules.

In some embodiments, the pharmaceutical composition for oral administration is an enteric coated tablet which has a solid core having a diameter of from about 5 to 8 mm. The diameter is the diameter of the widest dimension of the solid core. In some embodiments, the solid core diameter is about 5.5 to 7.5 mm. In some embodiments, the solid core diameter is about 6.0 to 7 mm, e.g. about 6 mm, about 6.5 mm or about 7 mm. Preferably, the pharmaceutical composition for oral administration is an enteric coated tablet which has a solid core having a diameter of 6.5 mm. More preferably, the pharmaceutical composition of the present invention is an enteric coated tablet which has a solid core having a diameter of 6.5 mm, and which comprises sodium meta-arsenite.

In some embodiments, the thickness of the solid core of the enteric coated tablet may be from about 2 mm to 6 mm, e.g. from about 2 mm to 5 mm. The thickness of the solid core of the enteric coated tablet is the depth of the solid core, i.e. the height of the solid core as measured when the solid core is resting on a flat surface. In some embodiments, the thickness of the solid core of the enteric coated tablet is about 3 to 4.5 mm. In some embodiments, the thickness of the solid core of the enteric coated tablet is about 3.1 to 4.2 mm, e.g. about 3.1 mm, about 3.2 mm, about 3.3 mm, about 3.4 mm, about 3.5 mm, about 3.6 mm, about 3.7 mm, about 3.8 mm, about 3.9 mm, about 4.0 mm, about 4.1 mm, or about 4.2 mm. Preferably, the thickness of the solid core of the enteric coated tablet is about 3.4 mm, about 3.5 mm, about 3.6 mm, about 3.7 mm, about 3.8 mm, or about 3.9 mm.

In some embodiments, the pharmaceutical composition for oral administration is an enteric coated capsule which has a solid core having a length of from about 8.0 to 16 mm. In some embodiments, the solid core length is about 8.5 to 15 mm. In some embodiments, the solid core length is about 8.5 to 14.5 mm, e.g. about 8.5 mm, about 9.0 mm, about 9.5 mm, about 10.0 mm, about 10.5 mm, about 11.0 mm, about 11.5 mm, about 12.0 mm, about 12.5 mm, about 13.0 mm, about 13.5 mm, about 14 mm, or about 14.5 mm. Preferably, the pharmaceutical composition for oral administration is an enteric coated capsule which has a solid core having a length of about 14.3 mm. More preferably, the pharmaceutical composition of the present invention is an enteric coated capsule which has a solid core having a length of about 14.3 mm, and which comprises sodium meta-arsenite.

In some embodiments, the thickness of the solid core of the enteric coated capsule may be from about 3 mm to 8 mm, e.g. from about 4.0 mm to 7.0 mm. The thickness of the solid core of the enteric coated capsule is the depth of the solid core, i.e. the height of the solid core as measured when the solid core is resting on a flat surface. In some embodiments, the thickness of the solid core is about 4.5 to 6.5 mm, e.g. about 4.5 mm, about 4.6 mm, about 4.7 mm, about 4.8 mm, about 4.9 mm, about 5.0 mm, about 5.1 mm, about 5.2 mm, about 5.3 mm, about 5.4 mm, about 5.5 mm, about 5.6 mm, about 5.7 mm, about 5.8 mm, about 5.9 mm, about 6.0 mm, about 6.1 mm, about 6.2 mm, about 6.3 mm, about 6.4 mm, or about 6.5 mm. Preferably, the thickness of the solid core of the enteric coated capsule is about 5.31 mm.

In some embodiments, the hardness of the solid core is from about 50 N to about 200 N, e.g. from about 50 to about 150 N or from about 70 to about 120 N. In some embodiments, the hardness of the solid core is from about 80 N to about 115 N, e.g. about 85 N, about 90 N, about 95 N, about 100 N, about 105 N, or about 110 N. In some embodiments, the hardness of the solid core is at least about 50 N, at least about 55 N, at least about 60 N, at least about 65 N, at least about 70 N, at least about 75 N, at least about 80 N, at least about 85 N, at least about 90 N, at least about 95 N, at least about 100 N, at least about 105 N, at least about 110 N, at least about 115 N, at least about 120 N, at least about 125 N, at least about 130 N, at least about 135 N, at least about 140 N, at least about 145 N, at least about 150 N, at least about 155 N, at least about 160 N, at least about 165 N, at least about 170 N, at least about 175 N, at least about 180 N, at least about 185 N, at least about 190 N, at least about 195 N, or about 200 N. Preferably, the hardness of the solid core is at least about 85 N, more preferably at least about 90 N, even more preferably at least about 100 N, and most preferably at least about 110 N. Typically, the hardness of the solid core does not exceed about 210 N.

In some embodiments, the friability of the solid core is less than about 0.5%, preferably less than about 0.45%, more preferably less than about 0.4%, even more preferably less than about 0.35%, and most preferably less than about 0.3%. In some embodiments, the friability of the solid core is less than about 0.25%. In some embodiments, the friability of the solid core is less than about 0.2%. In some embodiments, the friability of the solid core is less than about 0.15%. In some embodiments, the friability of the solid core is less than about 0.1%, e.g. about 0.08%.

In some embodiments, the mass of the solid core is from about 50 mg to 250 mg. In some embodiments, the mass of the solid core is from about 80 mg to 220 mg. In some embodiments, the mass of the solid core is from about 100 mg to 200 mg. In some embodiments, the mass of the solid core is from about 120 mg to 180 mg. In some embodiments, the mass of the solid core is from about 140 mg to 160 mg, e.g. about 140 mg, about 145 mg, about 150 mg, about 155 mg or about 160 mg. Preferably, the mass of the solid core is 150 mg.

In some embodiments, the pharmaceutical composition for oral administration comprises a solid core selected from the following:

- a solid core comprising sodium meta-arsenite, dibasic calcium phosphate anhydrous, L-hydroxypropyl cellulose, hydroxypropyl cellulose, colloidal silicon dioxide, and sodium stearyl fumarate;
- a solid core comprising sodium meta-arsenite, dibasic calcium phosphate anhydrous powder, partially pregelatinised starch, dibasic calcium phosphate anhydrous, sodium starch glycolate, colloidal silicon dioxide, and sodium stearyl fumarate;
- a solid core comprising sodium meta-arsenite, dibasic calcium phosphate anhydrous powder, dibasic calcium phosphate anhydrous, L-hydroxypropyl cellulose, sodium starch glycolate, colloidal silicon dioxide, and sodium stearyl fumarate;
- a solid core comprising sodium meta-arsenite, dibasic calcium phosphate anhydrous, partially pregelatinised starch, sodium starch glycolate, colloidal silicon dioxide, and sodium stearyl fumarate; and
- a solid core comprising sodium meta-arsenite, dibasic calcium phosphate anhydrous, silicified microcrystalline cellulose, sodium starch glycolate, colloidal silicon dioxide, and sodium stearyl fumarate.

In some embodiments, the pharmaceutical composition for oral administration is an enteric coated tablet comprising 1.67% w/w sodium meta-arsenite of the solid core, and having a solid core diameter of about 6.5 mm, a solid core mass of 150 mg, and an enteric coating which has added about 12% w/w of the solid core.

In some embodiments, the pharmaceutical composition for oral administration is an enteric coated tablet comprising 1.67% w/w sodium meta-arsenite of the solid core, and having a solid core diameter of about 6.5 mm, a solid core mass of 150 mg, and an enteric coating having a coating thickness of about 0.2 mm.

In some embodiments, after administration of the pharmaceutical composition for oral administration, the pharmaceutical composition has the following dissolution properties: not less than 75% in 45 minutes, preferably not less than 75% in 30 minutes.

In some embodiments, the dissolution of the pharmaceutical composition of the present invention and release of the API in the small intestines occurs rapidly or occurs over an extended period of time (e.g. 0.5, 0.75, 1, 2, 3, 4, 5 or 6 hours, preferably within 2 hours).

In some embodiments, upon dissolution of the enteric coating, the solid core disintegrates in less than about 10 minutes, preferably less than about 8 minutes, more preferably less than about 6 minutes, even more preferably less than about 5 minutes, and most preferably less than about 4 minutes.

The pharmaceutical composition for oral administration is preferably presented in unit dosage forms. The unit dosage form may be a packaged preparation, the package containing discrete quantities of the pharmaceutical composition, such as packeted tablets or capsules.

Also, the unit dosage form may be a tablet or capsule itself, or it may be the appropriate number of any of these in packaged form. The packaged form may, for example, comprise metal or plastic foil, such as a blister pack, such as Alu-Alu blisters which are impermeable or less permeable to oxygen. The packaged form may be accompanied by instructions for administration.

In some embodiments, the pharmaceutical composition for oral administration may be stored at ambient or room temperature for at least three months, preferably at least six months, more preferably at least one year, and most preferably for 18-24 months. In some embodiments, the pharmaceutical composition for oral administration may be refrigerated (e.g. at about 2-8 °C).

The pharmaceutical composition may be manufactured by the methods disclosed in WO 2019/178643 A1.

Compositions for Non-Oral Administration

In certain circumstances it will be desirable to deliver the pharmaceutical compositions disclosed herein parenterally, intravenously, intramuscularly, or even intraperitoneally. Solutions of the active compounds as freebase or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by national or regional offices of biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The formulations are easily administered in a variety of dosage forms such as injectable solutions, drug-release capsules, and the like.

The therapeutic agents can be formulated for parenteral administration by injection, e.g., by bolus injection or continuous infusion. Such formulations are sterile. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as emulsion in acceptable oils) or ion exchange resins, or as sparingly soluble derivatives, for example, as a sparingly soluble salt. Liposomes and emulsions are well known examples of delivery vehicles or carriers for hydrophilic drugs.

The appropriate pharmaceutically acceptable carriers and diluents to be utilized in the pharmaceutical preparations of the invention are well known to those skilled in the art of formulating compounds into pharmaceutical compositions. The pharmaceutical preparations of the invention that are in a form suitable for parenteral administration can be formulated for intravenous infusion or injection in numerous ways well known to those skilled in the art with pharmaceutically acceptable carriers. In certain embodiments, such pharmaceutical preparations are in the form of a freeze-dried mixture of the active ingredients in a unit dosage form, prepared by conventional techniques, which can be reconstituted with water or other suitable infusion liquid at the time of administration.

Dosages

Suitable dosages of the sodium or potassium meta-arsenite can be readily determined by a person skilled in the art.

An appropriate dosage level of the sodium or potassium meta-arsenite administered to a subject will generally be about 0.01-0.8 mg/kg subject body weight per day, e.g. about 0.05-0.7 mg/kg subject body weight per day, about 0.1-0.6 mg/kg subject body weight per day, or about 0.2-0.5 mg/kg of subject body weight per day, which can be administered in single or multiple doses per day.

For example, an appropriate dosage level of the sodium or potassium meta-arsenite administered to a patient (e.g. a patient suffering from Coronavirus infection, such as SARS-CoV-2 infection) may be about 2.0 to 30 mg/day/person, e.g. about 2.5 to 20.0 mg/day/person or about 2.5 to 17.5 mg/day/person. Preferably, the dosage level of the sodium or potassium meta-arsenite administered is about 5.0 to 12.5 mg/day/person, more preferably about 10.0 to 12.5 mg/day/person, e.g. 5.0 mg/day/person, 5.5 mg/day/person, 6.0 mg/day/person, 6.5 mg/day/person, 7.0 mg/day/person, 7.5 mg/day/person, 8.0 mg/day/person, 8.5 mg/day/person, 9.0 mg/day/person, 9.5 mg/day/person, 10.0 mg/day/person, 10.5 mg/day/person, 11.0 mg/day/person, 11.5 mg/day/person, 12.0 mg/day/person, or 12.5 mg/day/person. In some embodiments, the dosage level of the sodium or potassium meta-arsenite administered to a patient is 7.5 mg per day.

It will be understood that the specific dose level and frequency of dosage for any particular subject may be varied and will depend upon a variety of factors including the age, body weight, general health, sex and diet of the subject, the mode and time of administration, rate of excretion, drug combinations, and the severity of the particular condition.

The pharmaceutical composition of the present invention may be taken before (e.g. 30 minutes before) a meal, during a meal, or after (e.g. 30 minutes after) a meal. Preferably, the pharmaceutical composition of the present invention is taken immediately after a meal.

An example dosing regimen for a tablet of the present invention having 2.5 mg of sodium meta-arsenite (SMA) is set out below:

5.0 mg SMA intake: 1× tablet right after breakfast, 1× tablet right after dinner;

7.5 mg SMA intake: 2× tablets right after breakfast, 1× tablet right after dinner;

10.0 mg SMA intake: 2× tablets right after breakfast, 2× tablets right after dinner.

Administration with Other Agents

In some embodiments, the pharmaceutical composition may be used in combination with one or more other agents.

For example, the pharmaceutical composition described herein may be administered with other therapeutic agents, such as analgesics, anaesthetics, antifungals, antibiotics, antihistamines, antihypertensives, antimalarials, antimicrobials, antiseptics, antiarthritics, antithrombin agents, antituberculotics, antitussives, antivirals, cardioactive drugs, expectorants, immunosuppression agents, sedatives, sympathomimetics, toxins (e.g., cholera toxin), tranquillisers and urinary anti-infectives.

Sequential or substantially simultaneous administration of each therapeutic agent can be effected by any appropriate route including, but not limited to, oral routes, intravenous routes, intramuscular routes, direct absorption through mucous membrane tissues, and combinations thereof. The therapeutic agents can be administered by the same route or by different routes. For example, a first therapeutic agent of the combination selected can be administered by intravenous injection, e.g., cisplatin or arsenic trioxide, while the other therapeutic agent, e.g., sodium meta-arsenite can be administered orally. Alternatively, for example, both or all therapeutic agents can be administered by intravenous injection or infusion. The sequence in which the therapeutic agents are administered is not critical.

Kits

The invention also provides kits for carrying out the therapeutic regimens of the invention. Such kits comprise in one or more containers of therapeutically effective amounts of the SMA or KMA in pharmaceutically acceptable form. The SMA or KMA in a vial of a kit of the invention may be in the form of a pharmaceutically acceptable solution, e.g., in combination with sterile saline, dextrose solution, or buffered solution, or other pharmaceutically acceptable sterile fluid. Alternatively, the SMA or KMA may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes. The kit may also include another therapeutic agent(s) for the treatment of pain and/or inflammation in an appropriate amount. Such other therapeutic agent may be formulated as a combination drug with the SMA or KMA contained in the kit, or may be formulated separately.

The present invention is further described below by reference to the following non-limiting Examples.

EXAMPLES

Example 1—Inhibition of Proinflammatory Cytokine Secretion

Materials and Methods

All materials used to manufacture the pharmaceutical compositions exemplified below were purchased from commercial sources.

Macrophage Growth Media

Macrophages used were primary rat peritoneal macrophages. Macrophages were grown in DMEM, high glucose, pyruvate (Invitrogen Cat #11995) supplemented with heat-inactivated Fetal Bovine Serum (Invitrogen Cat. no. 10099-141) to a final concentration of 10%, penicillin/streptomycin (Invitrogen Cat. no. 15140-122) to a final concentration of 100 U/mL/100 μg/mL, glutamax (Invitrogen Cat. no. 35050-061) to a final concentration of 2 mM, and MEM NEAA (Invitrogen Cat. no. 11140-050) to a final concentration matching MEM media (Invitrogen Cat. no. 11095).

THP-1 cells and THP-1 macrophages were grown in RPMI, ATCC modification (Invitrogen Cat. no. A10491-01) supplemented with heat-inactivated Fetal Bovine Serum (Invitrogen Cat. no. 10099-141) to a final concentration of 10% and 2-mercaptoethanol to a final concentration of 0.05 mM.

All cells were incubated in a humidified atmosphere at 37 °C, 5% $CO_2$.

Cell Cytotoxicity and Viability (MTT-Based) Assays

The cytotoxicity and viability of cultured primary macrophages incubated with a range of $NaAsO_2$ concentrations relative to a vehicle control were determined at 24 hours post-treatment using the CytoTox-GLO kit (cytotoxicity) and MTT assay (viability).

On day 1, macrophage cells were seeded into 96-well plates by adding 125 μL of $1\times10^6$ cells/mL in growth medium to each well of a 96-well plate coated with 10% poly-L-lysine. Non-adhered cells were removed after 3 hours.

On day 2, growth medium was gently replaced with 100 μL/well fresh serum-free DMEM media for 3 hours. Serum-free medium was replaced with 63 μL medium containing a range of $NaAsO_2$ concentrations (30, 10, 7, 5, 3, 1, 0.3, 0.1, and 0 μM) and 100 ng/mL LPS or controls, and incubated for 24 hours.

On day 3:

1. Cytotoxicity was determined using CytoTox-GLO kit according to the manufacturer's instructions.
2. MTT reconstituted with DMEM to a final concentration of 5 mg/mL.
3. At 24 hours post-treatment, 6.3 μL of the reconstituted MTT solution was added to each well and incubated in a $CO_2$ incubator for 4 hours.
4. The resulting formazan crystals were dissolved by adding 70 μL of MTT Solubilisation Solution to each well and re-pipetting 10×.
5. The absorbance of each well was measured at a wavelength of 570 nm using a spectrophotometer with the background absorbance at 690 nm subtracted out.

Cytokine Secretion

To investigate the effects of $NaAsO_2$ on the secretion of cytokines from a primary culture of rat macrophages, supernatant from macrophage wells incubated with various concentrations of $NaAsO_2$ and LPS for 24 hours was analysed for proinflammatory cytokine concentrations using MesoScale Discovery V-PLEX kits.

Day 1

Macrophage cells were seeded into 24-well plates by adding 323 μL of $1\times10^6$ cells/mL in growth medium to each well of a 24-well plate coated with 10% poly-L-lysine. Non-adhered cells were removed after 3 hours and medium was replaced with 500 μL/well fresh DMEM medium.

Day 2

1. Growth medium was gently replaced with 500 μL/well fresh serum-free DMEM medium for 3 hours.
2. Serum-free medium was replaced with 250 μL growth medium containing a range of $NaAsO_2$ concentrations (30, 10, 7, 5, 3, 1, 0.3, 0.1, and 0 μM) and 100 ng/mL LPS (to induce an inflammatory state) or controls, and incubated for 24 hours.

Day 3

1. At 24 hours post-treatment, cell supernatant was collected and stored at −80 °C.
2. Proinflammatory cytokines were measured using MesoScale Discovery V-PLEX kits, per the manufacturer's instructions.

THP-1 Cell Differentiation

Day 1

THP-1 cells were seeded into 96-well plates by adding 250 μL of $2\times10^5$ cells/mL in THP-1 growth medium containing 1 μL/mL phorbol 12-myristate 13-acetate (PMA) to each well of a 96-well plate coated with 10% poly-L-lysine.

Day 2

Growth medium was gently replaced with 100 μL/well fresh serum-free growth medium for 2 hours. Serum-free medium was replaced with 63 μL growth medium containing a range of $NaAsO_2$ concentrations (30, 10, 7, 5, 3, 1, 0.3, 0.1, and 0 μM) and 100 ng/mL LPS (to induce an inflammatory state) or controls, and incubated for 24 hours.

Day 3

At 24 hours post-treatment, the MTT assay was performed as detailed above.

Data Analysis

Data are presented as mean (±SEM) and differences in primary macrophage cytokine secretion controls were determined using ANOVA with a post-hoc Tukey's Multiple Comparison test. Prism version 6.05 was used for all data figures, statistical analyses and $IC_{50}$ calculations.

The statistical significance criterion was p s 0.05.

Results

Primary peritoneal macrophages were harvested from rats, cultured for 24 hours in LPS (100 ng/mL) and sodium meta-arsenite in a range of concentrations (0.1-30 μM), followed by assessment of cytotoxicity and cell viability using the CytoTox-GLO and MTT assay kits (FIG. 1A). Digitonin, a detergent that is cytotoxic to cells, caused high toxicity compared with vehicle in the CytoTox-GLO kit (FIG. 1B). Additionally, Triton-X, another detergent, caused low cell viability compared with vehicle in the MTT assay (FIG. 1C). When incubated with sodium meta-arsenite, there was a concentration-dependent increase in cytotoxicity and a corresponding concentration-dependent decrease in viability. The cytotoxicity and cell viability plots used to derive the $EC_{50}$ and $IC_{50}$ values show a similar, but inverse relationship, indicating that the decrease in viability during sodium meta-arsenite incubation is likely due to cellular death, rather than just a failure of intracellular machinery.

Figure 2:
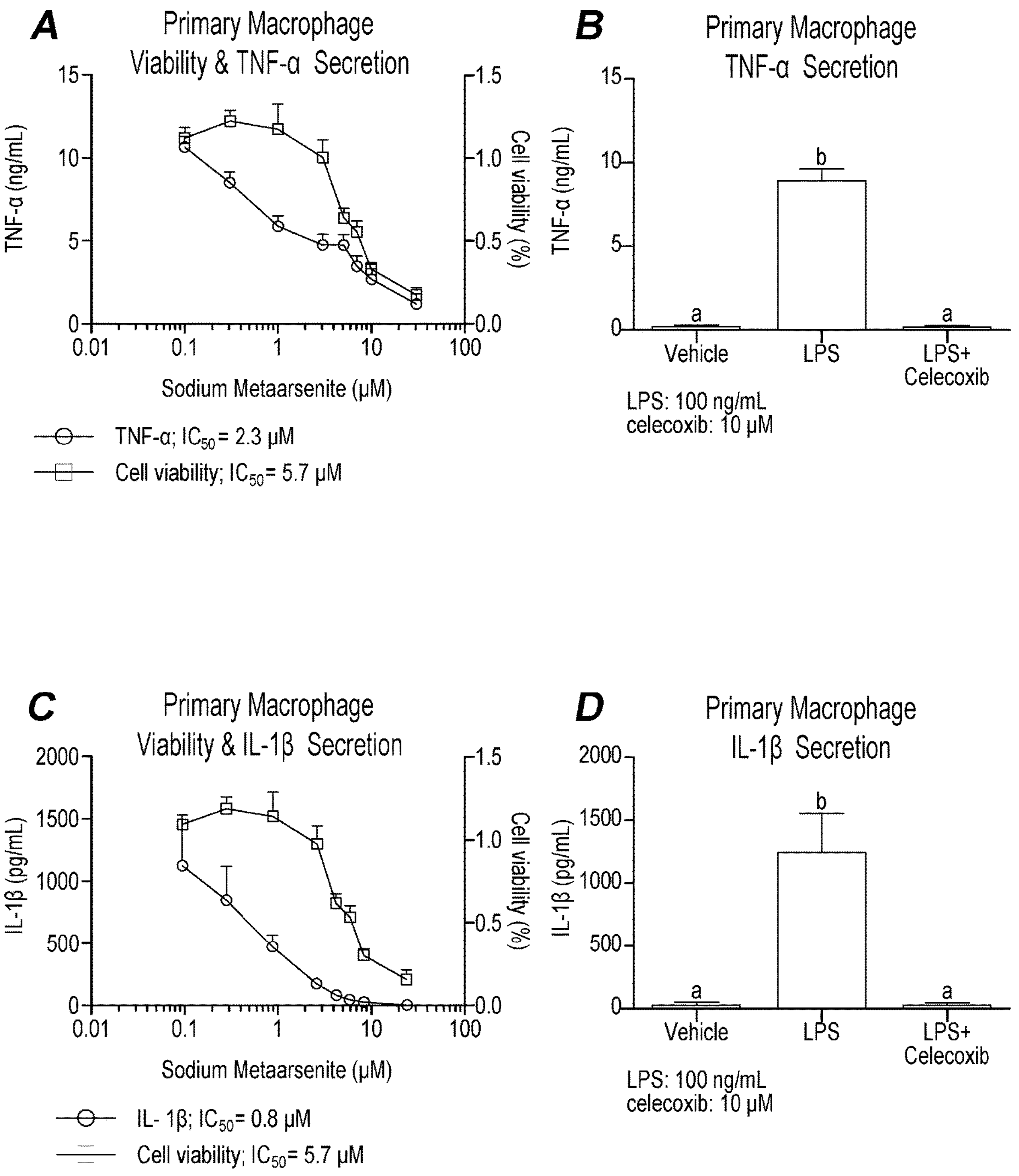
FIG. 2A to F are graphs showing the mean (±SEM) TNF-α (A), IL-1β (C) or IL-6 (E) secretion and viability of cultured primary rat macrophages incubated for 24 h in medium containing LPS at 100 ng/mL and various concentrations of sodium meta-arsenite (30, 10, 7, 5, 3, 1, 0.3 and 0.1 μM) relative to positive (celecoxib) and negative (vehicle) controls (B, D and F); n=3; values not sharing a common letter are significantly different (p≤0.05).
Figure 2:
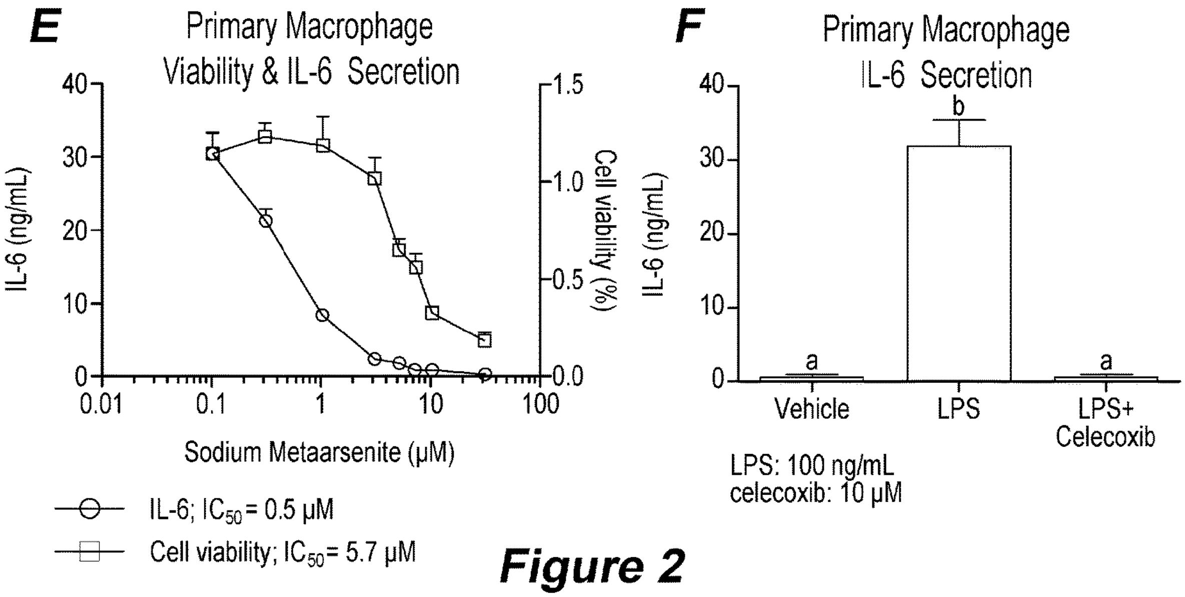

There was a concentration-dependent decrease in the secretion of TNF-α, IL-1β and IL-6 such that the $IC_{50}$ values were 2.3, 0.8 and 0.5 μM, respectively (FIGS. 2A, C and E). Importantly, the $IC_{50}$ for cell viability was higher at 5.7 μM, showing that sodium meta-arsenite inhibits release of the cytokines of interest from cultured primary macrophages at concentrations lower than the $IC_{50}$ for cell viability. These results suggest that sodium meta-arsenite may inhibit the secretion of cytokines TNF-α, IL-1β and IL-6 from cultured rat macrophages at a concentration that does not kill cells. Importantly, celecoxib (10 μM) successfully inhibited the secretion of all three proinflammatory cytokines (FIGS. 2B, D and E).

Summary

There was a concentration-dependent decrease in the secretion of proinflammatory cytokines, such that incubation of cells with sodium meta-arsenite at 3 μM, evoked complete inhibition of the secretion of IL-1β and IL-6 release from these cells in the absence of significant cell death.

There was significant inhibition of secretion of TNF-α, IL-1β and IL-6 from macrophage at concentrations of sodium meta-arsenite which did not significantly reduce cell viability.

In conclusion, the in vitro data herein show that incubation of cultured rat primary macrophages with sodium meta-arsenite for 24 h produces concentration-dependent inhibition of the secretion of proinflammatory cytokines.

Example 2

In this study, we investigated whether sodium meta-arsenite could suppress lipopolysaccharide (LPS)-induced inflammatory responses in murine macrophages Raw 264.7 cells. The macrophages activated by lipopolysaccharide produce numerous molecules and proteins, such as tumor necrotic factor-α (TNF-α), interleukin-6 (IL-6), IL-1β, inducible nitric oxide synthase (iNOS), cyclooxygenase-2 (COX-2), and free radicals, associated with acute inflammation. The response was induced by intracellular cascades, NF-κB pathway. So, the regulation of this pathway is very important in control of inflammation.

Cell Cultures

The murine macrophage cell line RAW 264.7 (American Type Culture Collection, ATCC; Manassas, VA, USA) was grown in DMEM supplemented with 10% heat-inactivated FBS and antibioticsantimycotics (100 U/ml penicillin G sodium, 100 μg/ml streptomycin sulfate and 0.25 mg/ml amphotericin). RAW 264.7 cells stably transfected with a pNF-κB-SEAP-NPT plasmid (SEAP-RAW cells) were kindly provided by Dr. Yeong Shik Kim (Seoul National University, Korea). SEAP-RAW cells were maintained in DMEM containing 500 μg/ml G418. All cells were incubated at 37 °C under 5% $CO_2$ in a humidified atmosphere.

Nitric Oxide (NO) Assay

RAW 264.7 macrophage cell lines were incubated with lipopolysaccharide (LPS, endotoxin of *E. coli*), and NO levels induced by COX-2 and iNOS were subsequently measured. Cytotoxicity was determined using sulforhodamine B assay or 3-(4,5-dimethylthiazole-2-yl)-2,5-diphenyl tetrazolium bromide (MTT).

Measurement of PGE2 Accumulation

For evaluating the inhibitory activity of test materials on COX-2, the RAW 264.7 cells were incubated with 1 μg/ml of LPS. After additional 20 h incubation, the media were removed and analyzed by PGE2 enzyme-linked immunosorbent assay (PGE2-ELISA). In these assays, activity is defined as the difference between PGE2 accumulation in the absence and in the presence of Sodium Meta-arsenite.

COX-2 Enzyme Activity Assay

For measurement of overexpressed COX-2 enzymic inhibition activity, RAW 264.7 cells were treated with LPS (1 μg/ml) for 20 h and cells were treated with sodium meta-arsenite for 30 minutes. Subsequently, cells were treated with COX-2 substrate (arachidonic acid, 10 μM) and the levels of PGE2 were determined using PGE2-ELISA.

RT-PCR Analysis

To extract total RNA after RAW 264.7 cells were pre-treated with Sodium Meta-arsenite for 30 minutes, cells were treated with LPS (1 μg/ml) for 5 h. Effect of Sodium Meta-arsenite for gene expression of iNOS, COX-2 mRNA and cytokines was determined by reverse transcription polymerase chain reaction (RT-PCR).

Western Blot Analysis

RAW 264.7 cells were pre-treated with Sodium Meta-arsenite for 30 minutes and cultured for 16 h, followed by treatment with LPS (1 μg/ml). Concentration of Protein obtained from broken cells determined using BSA assay. Effect of Sodium Meta-arsenite for protein expression of iNOS, COX-2, cytokines and NF-κB, Akt was determined by western blot analysis.

Reporter Gene Assay

After SEAP-RAW cells were pretreated with Sodium Meta-arsenite for 2 h, cells were incubated with LPS (1 μg/ml) for 18 h. The collected supernatants were heated at 65 °C for 5 minutes, given an SEAP assay buffer (2M diethanolamine, 1 mM $MgCl_2$, 500 μM 4-methylumbelliferylphosphate(MUP)] in the dark at 37 °C for 1 h. The fluorescence from the products of the SEAP/MUP was measured using a 96-well microplate fluorometer at an excitation of 360 nm and an emission at 449 nm and normalized by protein concentration. Data are expressed as a proportion of Sodium Meta-arsenite-treated to vehicle treated control cells without LPS.

Results

Effect of Sodium Meta-Arsenite on Nitric Oxide (NO) Production

Nitric oxide (NO) is a well known proinflammatory mediator in the pathogenesis of inflammation. Most NO is synthesized by the inducible nitric oxide synthase (iNOS). iNOS is an enzyme that is closely related to inflammatory response and cancer formation. The NO produced by iNOS has been described to influence on the activity and expression of COX-2. To investigate whether sodium meta-arsenite has NO inhibitory activities, NO production was determined in the presence of sodium meta-arsenite at 0.625-10 μM in LPS-induced RAW 264.7 mouse macrophage cells.

Figure 3:
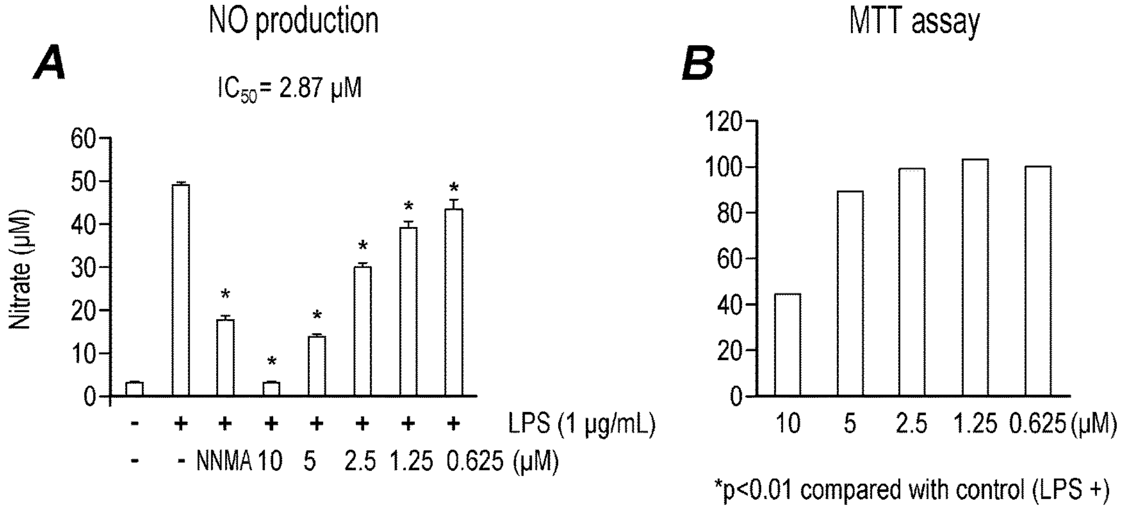
FIGS. 3A and B are: A. a graph showing nitric oxide production by RAW264.7 cells following stimulation with LPS, and treatment with and without various concentrations of sodium meta-arsenite (i.e. showing the effect of sodium meta-arsenite on nitric oxide production (iNOS assay)); and B. a graph showing cell viability following treatment with LPS and sodium meta-arsenite (*: p<0.01 compared with control (LPS+)).

NO production was significantly and concentration-dependently attenuated by sodium meta-arsenite (at concentrations of 10, 5, 2.5, 1.25 and 0.625 μM) 100.2, 77.2, 42.2, 21.5 and 12.5%, respectively. The IC50 value for inhibition of NO production of sodium meta-arsenite was about 2.87 μM (FIG. 3A).

Effect of Sodium Meta-Arsenite for PGE2 Production iNOS is highly expressed in macrophages, which leads to organ destruction in some inflammatory and autoimmune diseases. COX-2, also a proinflammatory enzyme, produces prostaglandin E2 (PGE2) by converting arachidonic acid into prostaglandins. PGE2 is also another important mediator which is produced from arachidonic acid metabolites which are catalyzed by COX-2 in inflammatory responses. Under basal condition, the products of iNOS and COX-2, including NO and prostaglandins, are involved in modulation of cellular functions and homeostasis.

Figure 4:
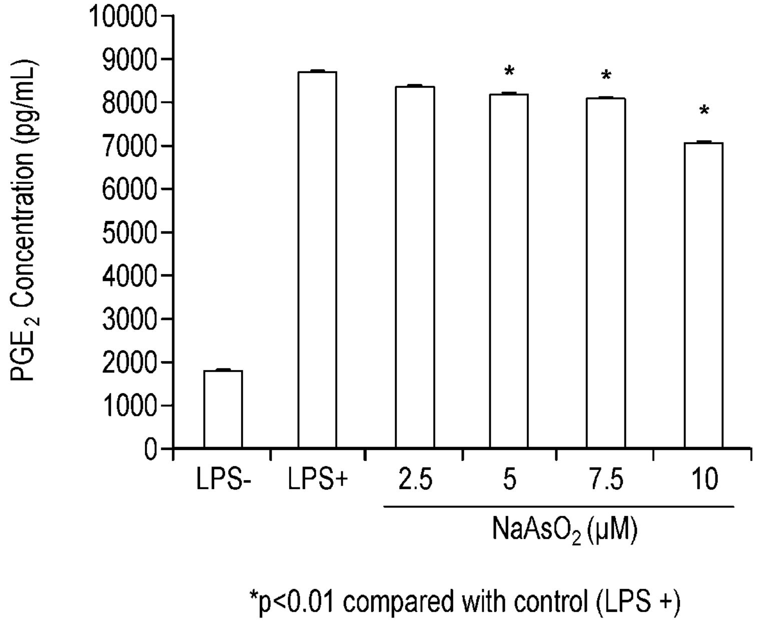
FIG. 4 is a graph showing Prostaglandin E2 (PGE2) production by RAW264.7 cells following stimulation with LPS, and treatment with and without various concentrations of sodium meta-arsenite (i.e. showing the effect of sodium meta-arsenite on PGE2 production (PGE2 assay); *: p<0.01 compared with control (LPS+)).

To investigate whether sodium meta-arsenite can regulate production of PGE2 by COX-2, PGE2 production was measured in RAW264.7 cells after treatment with sodium meta-arsenite (2.5, 5, 7.5 and 10 μM). Sodium meta-arsenite inhibited PGE2 production in a dose-dependent manner. At maximum dose (10 μM) of sodium meta-arsenite, PGE2 production was inhibited by 20% (FIG. 4).

Assessment of Sodium Meta-Arsenite on Protein Expression

Effect of Sodium Meta-Arsenite on Protein Expression of iNOS and COX-2

Figure 5:
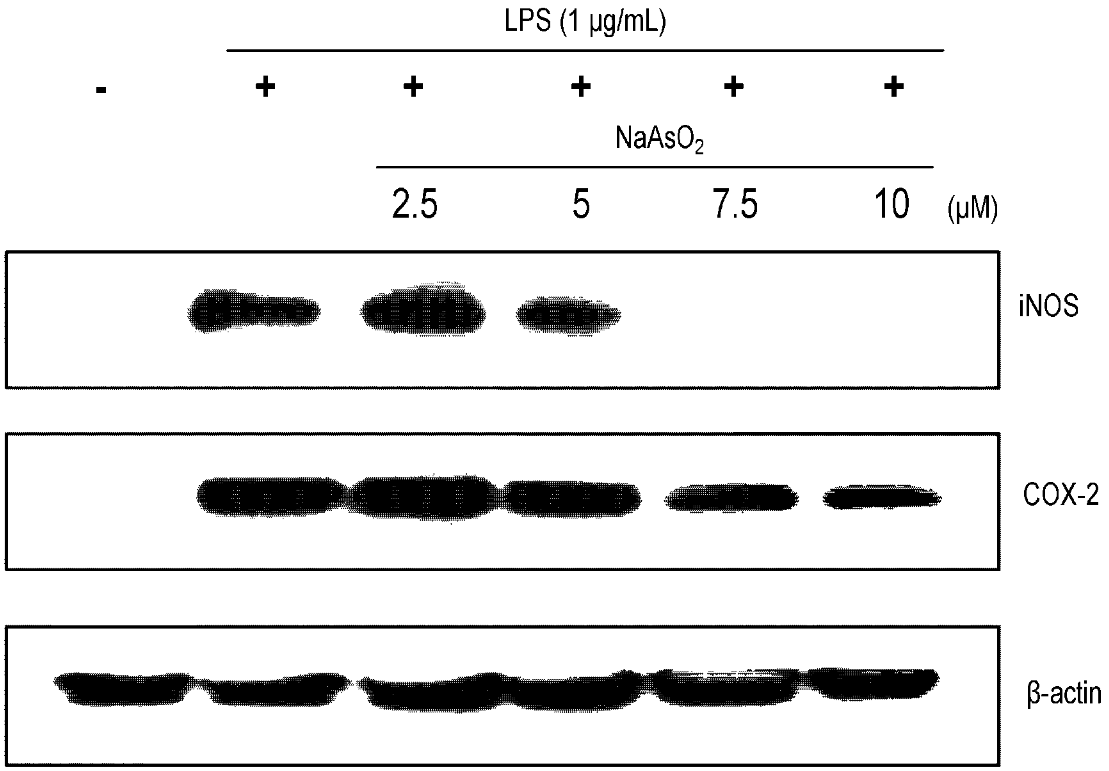
FIG. 5 is a Western blot showing expression of iNOS and COX-2 protein in RAW264.7 cells treated with LPS with and without various concentrations of sodium meta-arsenite (i.e. showing the effect of sodium meta-arsenite on iNOS and COX-2 protein expression).

To evaluate the inhibitory effects of sodium meta-arsenite on iNOS-induced COX-2 production, the iNOS and COX-2 protein levels were analyzed by Western blotting analysis. Raw 264.7 cells were pretreated with 2.5, 5, 7.5 or 10 μM sodium meta-arsenite for 30 min and stimulated with 1 μg/ml of LPS for 16 h. As shown in FIG. 5, iNOS expression was significantly inhibited by sodium meta-arsenite in a concentration-dependent manner. The expression of COX-2 was slightly inhibited by sodium meta-arsenite.

The Effect of Sodium Meta-Arsenite on Protein Expression of TNF-α and IL-1β

Figure 6:
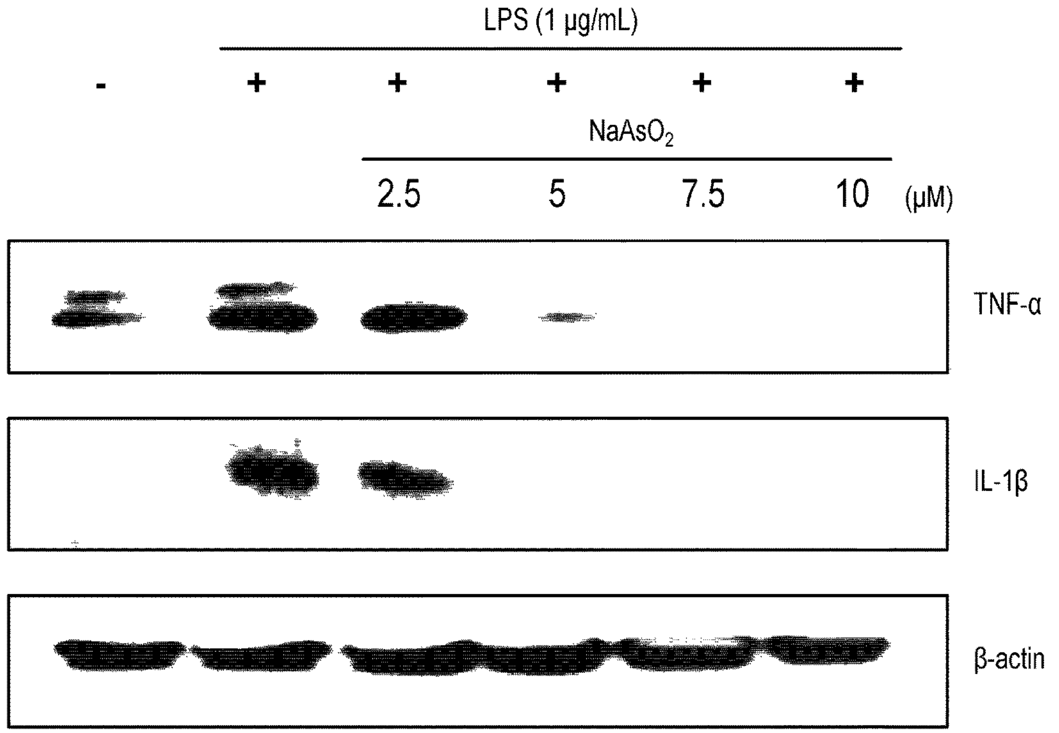
FIG. 6 is a Western blot showing expression of TNF-α and IL-1β protein in RAW264.7 cells treated with LPS with and without various concentrations of sodium meta-arsenite (i.e. showing the effect of sodium meta-arsenite on TNF-α and IL-1β protein expression).

The inflammatory cytokine, tumor necrosis factor-α (TNF-α) is considered a pivotal mediator in inflammatory response. In response to LPS, it also mediates the inflammatory response by secreting various proinflammatory mediators including IL-1β, and PGE2. IL-1β is a proinflammatory cytokine remarkable for its broad range of functions. The effect of sodium meta-arsenite on TNF-α and IL-1β protein levels were analyzed by Western blotting analysis. Raw 264.7 cells were pretreated with 2.5, 5, 7.5 or 10 μM sodium meta-arsenite for 30 min and stimulated with 1 μg/ml of LPS for 8 h. TNF-α and IL-1β expression were significantly inhibited by sodium meta-arsenite in a concentration-dependent manner (FIG. 6).

Assessment of Sodium Meta-Arsenite on Gene Expression

Effect of Sodium Meta-Arsenite on mRNA Expression of iNOS and COX-2

Figure 7:
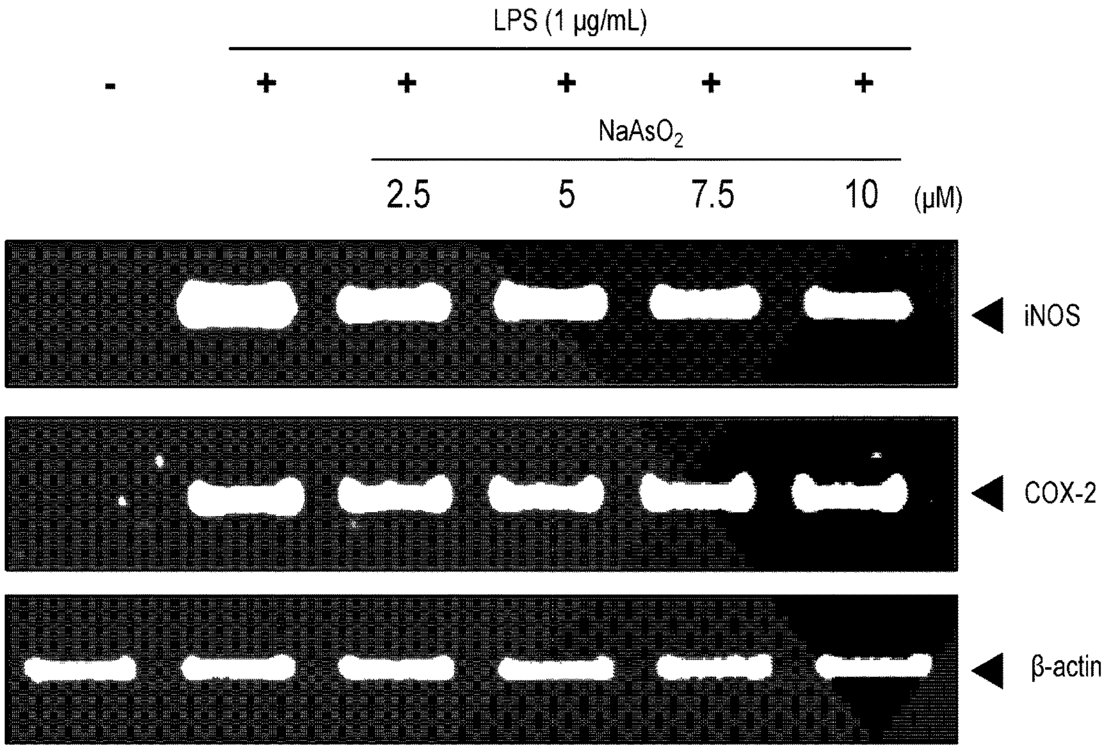
FIG. 7 is an image of an electrophoresis gel showing mRNA expression as determined by RT-PCR of iNOS and COX-2 in RAW264.7 cells treated with LPS with and without various concentrations of sodium meta-arsenite (i.e. showing the effect of sodium meta-arsenite on iNOS and COX-2 gene expression).
Figure 8:
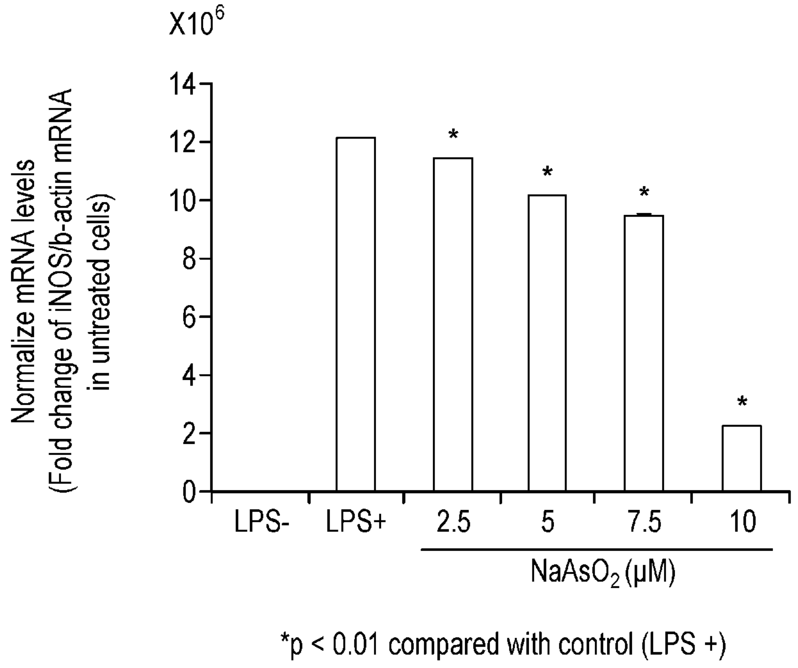
FIG. 8 is a graph showing iNOS mRNA expression in RAW264.7 cells treated with LPS with and without various concentrations of sodium meta-arsenite (i.e. showing the effect of sodium meta-arsenite on iNOS mRNA expression (real-time PCR); *: p<0.01 compared with control (LPS+)).

The effect of sodium meta-arsenite on iNOS and COX-2 mRNA expression was studied by RT-PCR. Raw 264.7 cells were pretreated with 2.5, 5, 7.5 or 10 μM sodium meta-arsenite for 30 min and stimulated with 1 μg/ml of LPS for 8 h. And then 1 μg of total RNA obtained was used for the RT-PCR.

iNOS expression was significantly inhibited by sodium meta-arsenite in a concentration dependent manner (FIG. 7 and FIG. 8). Expression of COX-2 was not influenced by sodium meta-arsenite (FIG. 7).

This confirmed that sodium meta-arsenite showed an inhibitory effect at iNOS rather than COX-2, suggesting that Sodium meta-arsenite potently inhibits inflammatory response via regulation of iNOS expression (FIG. 6). iNOS and COX-2 gene expression was analyzed by Western blotting analysis. The mRNA level of iNOS was measured by real-time PCR and was significantly inhibited by Sodium meta-arsenite in a concentration-dependent manner (FIG. 8).

The Effect of Sodium Meta-Arsenite on mRNA Expression of TNF-α and IL-1β

The inflammatory cytokine TNF-α is considered a pivotal mediator in inflammatory response. In response to LPS, they also mediate the inflammatory response by secreting various proinflammatory mediators including TNF-α, IL-1β, and PGE2. Among the proinflammatory cytokines, IL-1β or IFN-β has one of the highest potential of to cause damage to the host tissues, and in fact, various mechanisms are devoted to restrain its activity, intracellularly, by carefully controlling its transcription and processing by inflammatory response. Thus, the effect of Sodium meta-arsenite on TNF-α, IL-1β and IFN-β mRNA levels were analyzed by RT-PCR analysis.

Figure 9:
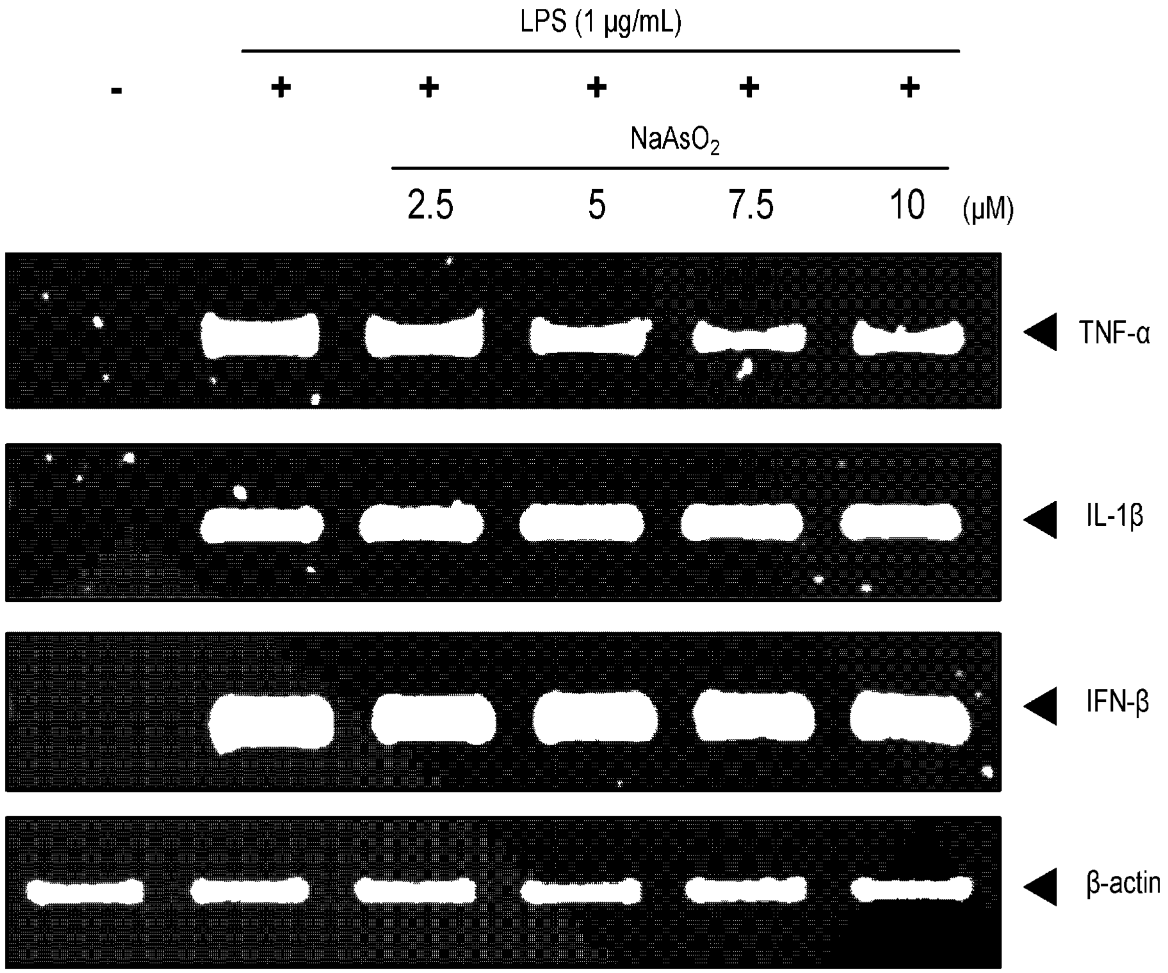
FIG. 9 is an image of gel electrophoresis of RT-PCR products showing TNF-α, IL-1β and IFN-β mRNA expression in RAW264.7 cells treated with LPS with and without various concentrations of sodium meta-arsenite (i.e. showing the effect of sodium meta-arsenite on TNF-α, IL-1β, and IFN-β gene expression).

Raw 264.7 cells were pretreated with 2.5, 5, 7.5 or 10 μM Sodium meta-arsenite for 30 min and stimulated with 1 μg/ml of LPS for 5 h. And then 1 μg of total RNA obtained was used for the RTPCR. The mRNA level of TNF-α was significantly decreased by sodium meta-arsenite in a concentration-dependent manner, but sodium meta-arsenite had no effect on the expression of IL-1β and IFN-β mRNA in RAW 264.7 macrophages (FIG. 9).

The Effect of Sodium Meta-Arsenite on Transcriptional Activity of Nuclear Factor Kappa B (NF-κB)

Figure 10:
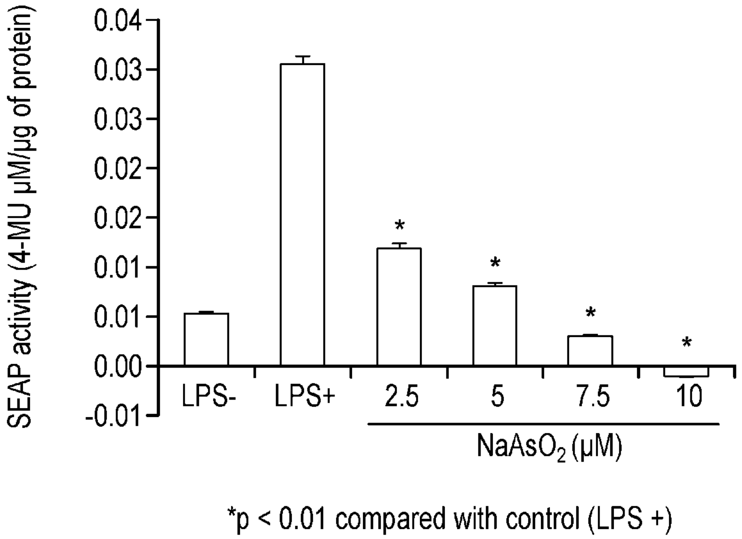
FIG. 10 is a graph showing NF-kB transcription activity in RAW264.7 cells treated with LPS with and without various concentrations of sodium meta-arsenite (i.e. showing the effect of sodium meta-arsenite on LPS-induced NF-κB transcriptional activity; *: p<0.01 compared with control (LPS+)).

NF-κB transcription factor has been shown to play a significant role in LPS-induced expression of proinflammatory mediators, including iNOS. The promoter region of the gene encoding iNOS contains NF-κB binding motifs, and it has been shown that binding of NF-κB to NF-κB sites upstream of iNOS promoter plays an important role in the LPS-induced upregulation of the iNOS gene. To investigate the molecular mechanism of inhibition of NF-κB transcription mediated by sodium meta-arsenite, NF-κB transcriptional activity was investigated using a reporter gene assay system. RAW 264.7 cells were stably transfected with a pNF-κB-secretory alkaline phosphatase (SEAP)-NPT plasmid containing four copies of the KB sequence fused to SEAP as the reporter. The pNF-κB-SEAP-NPT plasmid contains the neomycin phosphotransferase (NPT) gene for geneticin resistance in host cells was constructed and transfected into RAW 264.7 macrophages. Aliquots of the culture media were heated and then were reacted with 4-methylumbelliferyl phosphate(MUP). SEAP activity was measured as relative fluorescence units (RFU). LPS treatment of the transfected cells for 18 h increased the SEAP expression approximately 3-fold over the basal level compared with control cells without LPS. The treatment of cells with sodium meta-arsenite inhibited LPS-induced SEAP expression significantly in a concentration dependent manner (FIG. 10).

To examine whether sodium meta-arsenite regulates NF-κB signal transduction pathways, RAW264.7 macrophages were treated with LPS (1 μg/mL) for 15 min in pretreatment of sodium meta-arsenite (2.5, 5, 7.5 or 10 μM) for 30 min and levels of p65, p50, IκB, and IKK were also analyzed by Western blotting analysis.

Figure 11:
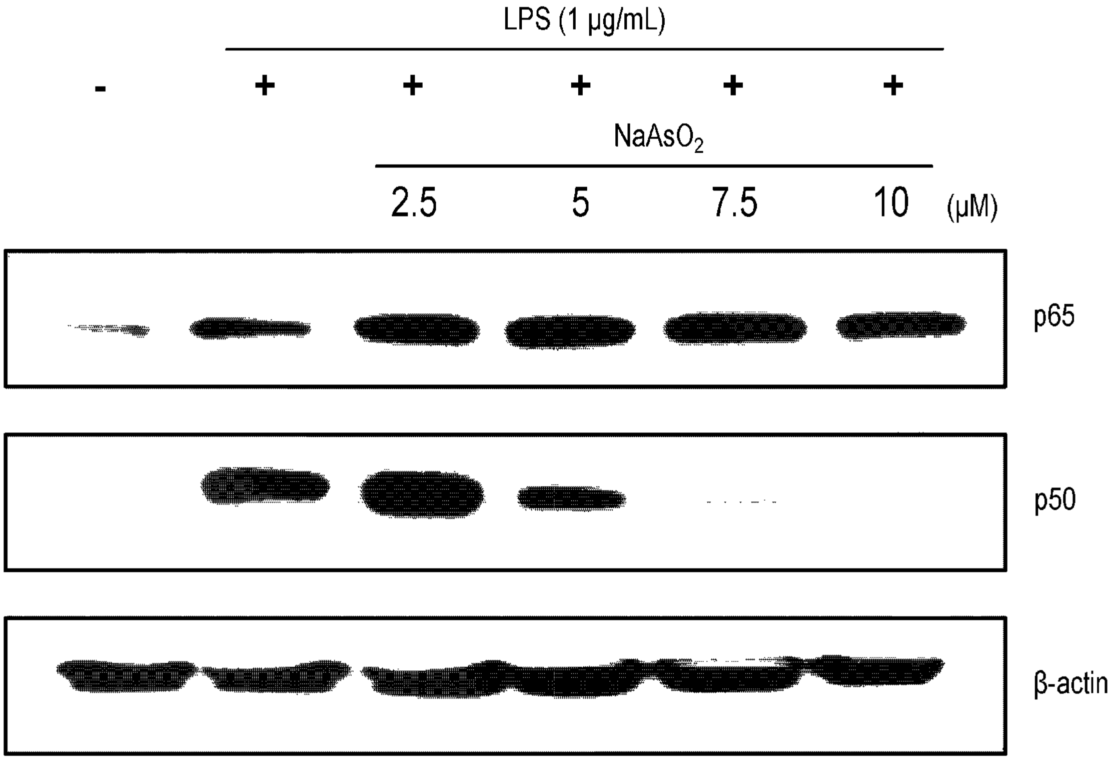
FIG. 11 is a Western blot showing protein expression of NF-kB (p50) and (p65) in RAW264.7 cells treated with LPS with and without various concentrations of sodium meta-arsenite (i.e. showing the effect of sodium meta-arsenite on NF-kB protein expression).
Figure 12:
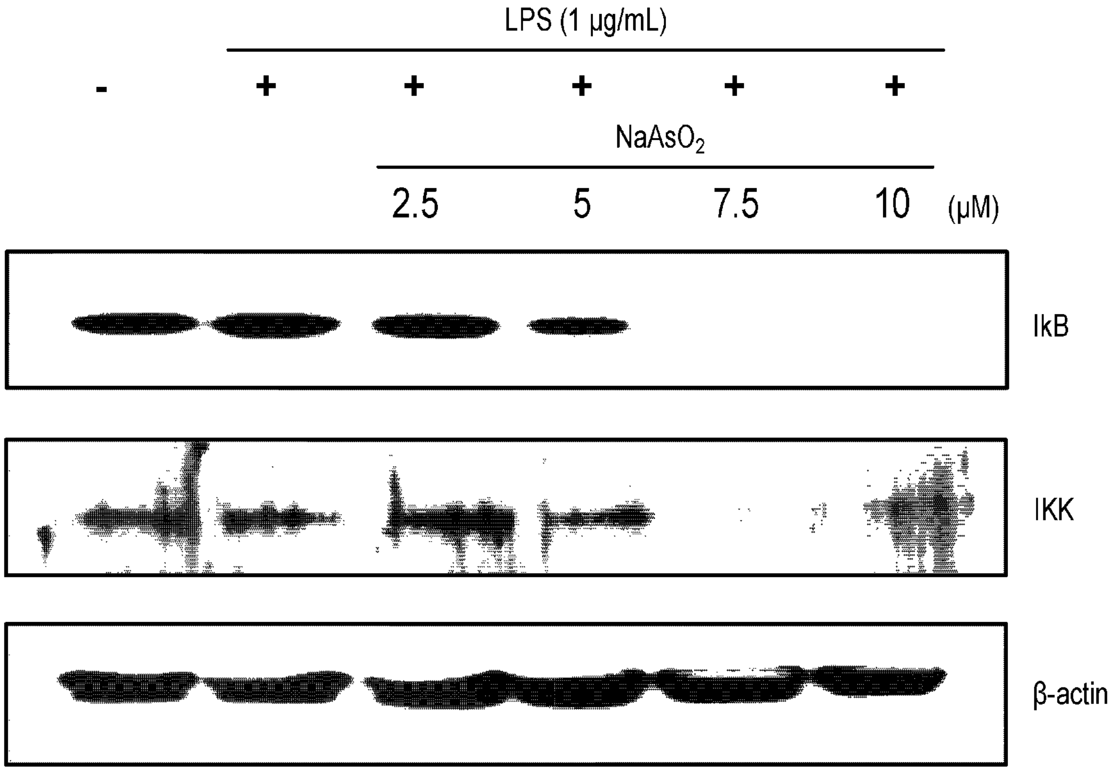
FIG. 12 is a Western Blot showing protein expression of IκB and IKK in RAW264.7 cells treated with LPS with and without various concentrations of sodium meta-arsenite.

Sodium Meta-arsenite markedly decreased NF-κB protein level in a concentration-dependent manner (FIG. 11). Sodium meta-arsenite markedly inhibited IκB degradation in a concentration dependent manner (FIG. 12).

Example 3—Preparation of Oral Compositions

Oral Composition

Sodium meta-arsenite ("SMA") was obtained from Sigma Aldrich Fine Chemicals. As supplied, the SMA drug substance exhibited very high purity (>98% As(III)) and minimal levels of As(V). Table 1 below provides the properties of the supplied SMA drug substance.

TABLE 1

| Properties of the supplied SMA drug substance | |
|---|---|
| Property | Value/Observation |
| Appearance | White to off-white powder |
| Melting point | 615 °C |
| Solubility | Approx. 950 mg/mL |
| Typical assay (As(III)) | 98-99% |
| Typical Impurity Level (As(V)) | ≤0.2% |
| Typical water content | <1.0% |
| Hygroscopicity (moisture uptake) | ~40% at 75% RH<br>>80% at 80% RH<br>>130% at 90% RH |
| Density (true/particle) | 2.1-2.3 g/cm$^3$ |

The materials listed in Table 2 below were used to prepare the 2.5 mg sodium meta-arsenite ("SMA") enteric coated tablets. Where possible, higher density versions of major excipients were selected in an effort to match the density of SMA (an inorganic material with an estimated true density of approximately 2.1 to 2.3 g/cm$^{-3}$, which is very dense compared with most excipients).

TABLE 2

| List of materials | | |
|---|---|---|
| Materials | Function | Trade Name/Supplier |
| Sodium meta-arsenite ("SMA") (>98% pure) | active pharmaceutical ingredient | Sigma Aldrich Fine Chemicals (Madison, Wisconsin, USA) |
| Calcium sulphate dihydrate | filler | Compactrol/JRS pharma |
| Calcium carbonate | filler | PressCAL MD 92.5/JRS |
| Calcium carbonate finer grade | filler | Not applicable/JRS |
| Dibasic calcium phosphate anhydrous | filler | Fujicalin/Fuji chemicals |
| Dibasic calcium phosphate anhydrous powder | filler | A Comprez/JRS pharma |
| Dibasic calcium phosphate anhydrous fine grade | filler | A-Comprez/JRS pharma |
| Silicified microcrystalline cellulose (sMCC) high density grade | filler, compressible diluent | Prosolv HD 90 |
| Microcrystalline cellulose (MCC) high density grade | binder | Avicel PH302/FMC |
| Partially pregelatinised starch | binder, disintegrant, filler | Lycatab C-LM/Roquette |
| Partially pregelatinised starch | binder, disintegrant, filler | Starch 1500/Colorcon |
| Hydroxypropyl cellulose | binder | Klucel EXF/Ashland |
| L-Hydroxypropyl cellulose | binder, disintegrant | LH-B1/Shin-EtSu |
| Colloidal silicon dioxide | glidant | Aerosil 200/Evonik |
| Sodium starch glycolate | super disintegrant | Explotab/JRS Pharma |
| Croscarmellose sodium | super disintegrant | Ac-di-Sol/FMC |
| Sodium stearyl fumarate | lubricant | PRUV/JRS pharma |
| Opadry II (20A280013) | sub-coat | Colorcon |
| Acryl-EZE II white (493Z180022) | coating polymer | Colorcon |

The equipment listed in Table 3 below was used in the preparation and analysis of the SMA enteric coated compositions.

TABLE 3

| List of equipment | | |
|---|---|---|
| Equipment Name | Manufacturer | Usage |
| Balance | Sartorius | weighing materials and tablets |
| Turbula blender | Turbula | blending |
| 2 L Turbula mixing jar | Turbula | blending |

TABLE 3-continued

| List of equipment | | |
|---|---|---|
| Equipment Name | Manufacturer | Usage |
| Density meter | Copley | density measurement |
| Manesty F3 press (single punch) | Manesty | tabletting |
| Rotary press (7 stations) | SCI | tabletting |
| 6.5 mm round normal biconcave NCCP tools | Natoli | tabletting |
| 0.25 inch tooling Key International tablet machine | Key International | tabletting |
| Hardness tester | Copley | measuring tablet hardness |
| Micrometer | Mitsuyi | measuring tablet thickness |
| Friability tester | Copley | testing friability |
| Disintegration bath | Copley | testing disintegration |
| 15" Coating pan | Thai Coater | coating |

Manufacturing Example 1

The enteric coated tablets of Formulation Examples 1.1 to 1.4 comprising sodium meta-arsenite ("SMA") as the active pharmaceutical ingredient (API) were prepared following the procedure described below.

In general, and as described in detail below, the sodium meta-arsenite ("SMA") and excipients were blended together (in a three-stage blending process without the use of water or solvent) to form a powder blend. The powder blend was then compressed to form the solid core of the tablet. The solid core of the tablet was then coated with an enteric coating.

Blending

The blending process described below was used for blending the ingredients.

The API and the other ingredients for the composition were dispensed and weighed. Since the concentration of the API was very low, a three-stage blending process (utilising an "API premix" and a "main mix") was utilised in an effort to improve blend uniformity.

The API was screened through a 200 μm sieve (hand screen). The sieving time was between 5-8 minutes.

A premix containing the API (the "API premix") was prepared by blending the screened API with a few grams (20 g for a 500 g batch size and 30 g for a 700 g batch size) of filler in an appropriate container (100 ml container for a 500 g batch size and 150 ml for a 700 g batch size) for 10 minutes at 49 rpm with a Turbula blender.

The glidant (colloidal silicon dioxide) was screened through a 500 μm sieve to de-agglomerate. Then all other dispensed ingredients including the sieved glidant, except the lubricant (sodium stearyl fumarate), were added into a 2 L glass Turbula jar, with the API premix sandwiched in the middle of the powder mass.

The resulting mixture (the "main mix") was blended for between about 10 to about 20 minutes at 49 rpm using a Turbula blender to form a blended powder (the "main blend").

The lubricant (sodium stearyl fumarate) was co-screened with a small portion of the main blend using a 500 μm sieve, and then the co-screened mixture was added to the main blend. This lubrication step was done separately in an effort to avoid possible complications from over-lubrication (e.g. reduction in tablet hardness or dissolution issues).

The resulting mixture was mixed for 2 minutes at 49 rpm in the Turbula blender thereby forming the powder blend. The powder blend was characterized for flow properties.

Compressing

The powder blend was compressed on a Manesty F3 single punch tablet press using 6.5 mm normal concave plain (NCCP) tooling at a target tablet weight of 150 mg. The Manesty F3 only has arbitrary units (AU) for compression force and it is not possible to directly measure the applied force. The targeted level of hardness was above 90 N.

Enteric Coating

A 20% w/w solid content enteric coating dispersion was prepared by dispersing Acryl-EZE II white (493Z180022) in deionised water. The dispersion was stirred using a paddle stirrer for 45 minutes before use and throughout the coating process. The dispersion was screened through a 250 μm sieve before being used.

The 15" coating pan (Thai Coater) was allowed to equilibrate to the set point temperature prior to charging with the solid cores of the tablets. Due to the small batch sizes, 'bulking inerts' were added to the API solid cores to meet the loading requirements for the coating pan. The solid cores of the tablets were allowed to equilibrate in the drying pan for 10 minutes prior to coating. The same temperature and airflow was used for the heating, coating and drying phases. The coated tablets were dried for 10 minutes in the pan after coating. Samples were collected after 8, 10 and 12% w/w weight gain.

Dissolution Studies

Dissolution studies were carried out using 500 mL of media and USP Method 2 (paddles) initially with a paddle speed of 100 rpm. A single set of six enteric coated tablets (n=6) were examined. Samples of dissolution media were withdrawn after 2 hours in acid and the levels of sodium meta-arsenite determined to assess gastric resistance. The media was replaced with the pH 6.8 phosphate buffer and samples were withdrawn at intervals of 15 minutes to generate dissolution profiles.

This method is based on the pharmacopoeial method for enteric dosage forms (EP. 2.9.3 and USP <711>) as shown in Table 4 below.

TABLE 4

Conditions of dissolution studies

| Stage | Conditions | Description | Purpose | Requirement |
| --- | --- | --- | --- | --- |
| 1 | 0.01M HCl | Acid phase | Acid resistance | Not more than 10% release in 2 hours |
| 2 | pH 6.8 phosphate buffer | Buffer Phase | Release profile | Typically, not less than 75% in 30-45 minutes |

Formulation

A solid pharmaceutical composition (P63) comprising sodium meta-arsenite (SMA) as the active pharmaceutical ingredient (API) was prepared using the method described above in Manufacturing Example 1.

The composition was manufactured at a 700 g scale. Blend uniformity and content uniformity samples were collected to assess the homogeneity after the main blending time of 20 minutes.

Table 5 below provides the composition of the solid core of the tablet comprising 2.53 mg of sodium meta-arsenite (prior to the coating step). (Table 5.1 below provides another possible composition of the solid core of the tablet comprising 2.50 mg of sodium meta-arsenite (prior to the coating step).)

TABLE 5

Composition of the solid core of the P63 tablet

| Material | Function | mg/ tablet | % w/w |
| --- | --- | --- | --- |
| Sodium meta-arsenite | API | 2.53 | 1.69 |
| Dibasic calcium phosphate anhydrous (A-Comprez fine granule) | filler | 82.22 | 54.81 |
| L-Hydroxypropyl cellulose (LH-B1 grade) | binder, disintegrant | 60.00 | 40.00 |
| Hydroxypropyl cellulose (Klucel EXF) | binder | 3.00 | 2.00 |
| Colloidal silicon dioxide (Aerosil 200) | glidant | 0.75 | 0.50 |
| Sodium stearyl fumarate (PRUV) | lubricant | 1.50 | 1.00 |
| Total | | 150.00 | 100.00 |

Following the blending step, the powder blend demonstrated good flow properties as indicated by the Carr's Index (29.3%). The powder blend prior to compression had the following properties:

Aerated density: 0.64 g/cm$^3$

Tapped density: 0.91 g/cm$^3$

Carr's index: 29.3%

Hausner ratio: 1.30

The powder blend compressed very well and no weight variation and/or visual segregation was observed throughout the run. High tablet hardness (104.8 N) and low friability (0.08%) were achieved, and disintegration time (34 seconds) was relatively rapid. The mean thickness of the solid core of the tablet was 3.63 mm.

Blend uniformity samples were taken after blending for 20 minutes and content uniformity samples were collected at the start, middle and end of the compression run. Blend uniformity results exhibited excellent homogeneity with a % relative standard deviation (RSD) value of 1.3. The content uniformity of the solid cores of the tablet across the compression run (start, middle and end) showed good homogeneity as a maximum acceptance value (AV) value of <7.4 was achieved (AV value of <15 is acceptable).

Following the compression step, the solid core of the tablet was coated with Acryl-EZE II white (493Z180022) enteric coating polymer system, which was prepared as described in Manufacturing Example 1. The coating parameters are shown in Table 6 below.

TABLE 6

| Coating parameters | |
|---|---|
| Parameter | Result |
| Coating pan | 15" Thai Coater |
| Inlet Temp | 90-110 °C |
| Exhaust Temp | ~50 °C |
| Drum Speed | 16 rpm |
| Spray Rate | 10-11 g/min |
| Bed Temp | ~35 °C |
| Inlet and Exhaust Shut | Both at middle |
| Gun to Bed Distance | 5 cm (Baffles not visible) |
| Fluid nozzle (mm) | 1.2 mm |
| Fan Air Pressure | 20 psi |
| Spray gun Air Pressure | 10 psi |
| Weight of Bulking inert (g) | 2500.0 g |
| Weight of active tablets (g) | 473.0 g |
| Weight of tablet bed (g) | 2973.0 g |
| Initial weight of 20 tablets (g) | 3.017 g |
| Target weight gain for 12% coating (g) | 3.379 g |
| Weight of 20 tablets after 12% weight gain (g) | 3.381 g (12.06% weight gain) |

The enteric coated tablet exhibited an acceptable dissolution profile (500 ml media, paddle speed 100 rpm). After 120 minutes, the composition was intact in acidic media (pH 1.0) with 0% API release. After 135 minutes at pH 6.8, 91% of the API was released. After 150 minutes at pH 6.8, 98% of the API was released. After 165 minutes at pH 6.8, 100% of the API was released.

The enteric coated tablet demonstrated satisfactory gastric resistance and met the proposed preliminary specification of not less than 75% release in 45 minutes for enteric dosage forms.

Table 5.1 below provides another possible composition of the solid core of the tablet comprising 2.50 mg of sodium meta-arsenite (prior to the coating step). A solid core having the components described in Table 5.1 may be prepared in a similar manner as described above for the solid core having the components described in Table 5.

TABLE 5.1

| Alternative composition of the solid core of the P63 tablet | | | |
|---|---|---|---|
| Material | Function | mg/ tablet | % w/w |
| Sodium meta-arsenite | API | 2.50 | 1.67 |
| Dibasic calcium phosphate anhydrous (A-Comprez fine granule) | filler | 82.25 | 54.83 |
| L-Hydroxypropyl cellulose (LH-B1 grade) | binder, disintegrant | 60.00 | 40.00 |
| Hydroxypropyl cellulose (Klucel EXF) | binder | 3.00 | 2.00 |
| Colloidal silicon dioxide (Aerosil 200) | glidant | 0.75 | 0.50 |
| Sodium stearyl fumarate (PRUV) | lubricant | 1.50 | 1.00 |
| Total | | 150.00 | 100.00 |

Formulation Example 1.2

A solid pharmaceutical composition (P23) comprising sodium meta-arsenite (SMA) as the active pharmaceutical ingredient (API) was prepared using the method described above in Manufacturing Example 1.

The composition was manufactured at a 500 g scale. Blend uniformity samples were collected after 10, 15 and 20 minutes of the main blending time. The blend was compressed to form the solid core of the tablet, and then the solid core of the tablet was coated.

Table 7 below provides the composition of the solid core of the tablet comprising 2.50 mg of sodium meta-arsenite (prior to the coating step).

TABLE 7

| Composition of the solid core of the P23 tablet | | | |
|---|---|---|---|
| Material | Function | mg/ tablet | % w/w |
| Sodium meta-arsenite | API | 2.50 | 1.67 |
| Dibasic calcium phosphate anhydrous powder (A-Comprez powder) | filler | 37.50 | 25.00 |
| Partially pregelatinised starch (Starch 1500) | binder, disintegrant, filler | 45.00 | 30.00 |
| Dibasic calcium phosphate anhydrous granule (Fujicalin) | filler | 58.25 | 38.83 |
| Sodium starch glycolate (Explotab) | Super disintegrant | 4.50 | 3.00 |
| Colloidal silicon dioxide (Aerosil 200) | glidant | 0.75 | 0.50 |
| Sodium stearyl fumarate (PRUV) | lubricant | 1.50 | 1.00 |
| Total | | 150.00 | 100.00 |

Following the blending step, the powder blend demonstrated good flow properties as indicated by the Carr's Index (26.37%). The powder blend prior to compression had the following properties:

Aerated density: 0.67 g/cm$^3$

Tapped density: 0.91 g/cm$^3$

Carr's index: 26.37%

Hausner ratio: 1.36

Angle of repose: 24.32°

Blend uniformity samples were collected after blending for 10, 15 and 20 minutes of the main blending time. The composition exhibited good homogeneity at 20 minutes blend time.

Compression was performed on a Manesty F3 single punch machine using 6.5 mm NCCP tools. The mean solid core hardness was 94.3 N, the mean thickness was 3.62 mm, the friability was 0.33%, and the disintegration time was 39 seconds.

The weight of the solid cores was consistent throughout the compression run and acceptable solid cores were produced. No visual segregation was observed. Samples (10 solid cores in duplicate) were collected at start, middle and end of the compression run and sent for content uniformity testing.

Following the compression step, the solid core of the tablet was coated with Acryl-EZE II white (493Z180022) enteric coating polymer system, which was prepared as described in Manufacturing Example 1, and samples were collected after 8, 10 and 12% w/w weight gain. The coating parameters are shown in Table 8 below.

TABLE 8

| Coating parameters | |
|---|---|
| Parameter | Result |
| Coating Pan | Thai Coater |
| Inlet Temp | 81-90 °C |
| Exhaust Temp | ~50 °C |
| Drum Speed | 18 rpm reduced to 16 rpm |
| Initial Spray Rate | 7 g/min |
| Spray Rate after 30 minutes | 11 g/min |
| Bed Temp | ~35 °C |
| Inlet and exhaust Shut | Both at middle |
| Gun to Bed Distance | 5 cm (Baffles not visible) |
| Pump Speed | 05 |
| Fluid nozzle (mm) | 1.2 mm |
| Spray gun air pressure | 10 psi |
| Fan air pressure | 20 psi |
| Weight of Bulking inert (g) | 3000 g |
| Weight of active tablets (g) | 240 g |
| Weight of tablet bed (g) | 3240 g |
| Initial weight of 20 tablets (g) | 3.015 g |
| % w/w target for tablet coat | 8% |
| Target weight gain for 8% coating (g) | 3.256 g |
| Amount of dispersion sprayed to achieve 8% weight gain (g) | 1900 g |
| Weight of 20 tablets after 8% weight gain (g) | 3.248 g |
| % w/w target for tablet coat | 10% |
| Target weight gain for 10% coating (g) | 3.317 g |
| Amount of dispersion sprayed to achieve 10% weight gain (g) | 2400 g |
| Weight of 20 tablets after 10% weight gain (g) | 3.328 g |
| % w/w target for tablet coat | 12% |
| Target weight gain for 12% coating (g) | 3.377 g |
| Amount of dispersion sprayed to achieve 12% weight gain (g) | 2900 g |
| Weight of 20 tablets after 12% weight gain (g) | 3.384 g |

The enteric coated tablets with weight gains of 8%, 10% and 12% w/w underwent dissolution testing (500 ml dissolution media, paddle speed 75 rpm) to identify suitable levels of enteric coating. The dissolution results are presented in Table 9 below.

TABLE 9

| Dissolution results | | | | | |
|---|---|---|---|---|---|
| | Mean (% drug released) Time (min) | | | | |
| | 120 | 135 | 150 Media | 165 | 195 |
| Sample name | pH 1.0 | pH 6.8 | pH 6.8 | pH 6.8 | pH 6.8 |
| 8% w/w enteric coated tablets | 00 | 67 | 80.5 | 87 | 90 |
| 10% w/w enteric coated tablets | 00 | 26 | 82 | 89 | Not determined |
| 12% w/w enteric coated tablets | 00 | 27 | 83 | 90 | 92 |

The enteric coated tablets were intact in the acidic media after 120 minutes. The enteric coated tablets demonstrated satisfactory gastric resistance and met the proposed preliminary specification of not less than 75% release in 45 minutes for enteric dosage forms.

Based on the dissolution results, it was found that 12% w/w was the optimum coating weight gain.

Formulation Example 1.3

A solid pharmaceutical composition (P31) comprising sodium meta-arsenite (SMA) as the active pharmaceutical ingredient (API) was prepared using the method described above in Manufacturing Example 1.

The composition was manufactured at a 500 g scale. Blend uniformity samples were collected after 10, 15 and 20 minutes of the main blending time. The blend was compressed to form the solid core of the tablet, and then the solid core of the tablet was coated. L-Hydroxypropyl cellulose (L-HPC; low substituted hydroxypropyl cellulose LH-B1 grade) was used as it acts as a binder and disintegrant. As L-HPC is insoluble in water it was expected that this would give hard tablets.

Table 10 below provides the composition of the solid core of the tablet comprising 2.50 mg of sodium meta-arsenite (prior to the coating step).

TABLE 10

| Composition of the solid core of the P31 tablet | | | |
|---|---|---|---|
| Material | Function | mg/ tablet | % w/w |
| Sodium meta-arsenite | API | 2.50 | 1.67 |
| Dibasic calcium phosphate anhydrous powder (A-Comprez powder) | filler | 37.50 | 25.00 |
| Dibasic calcium phosphate anhydrous granule (Fujicalin) | filler | 80.75 | 53.83 |
| L-Hydroxypropyl cellulose (LH-B1 grade) | binder, disintegrant | 22.50 | 15.00 |
| Sodium starch glycolate (Explotab) | super disintegrant | 4.50 | 3.00 |
| Colloidal silicon dioxide (Aerosil 200) | glidant | 0.75 | 0.50 |
| Sodium stearyl fumarate (PRUV) | lubricant | 1.50 | 1.00 |
| Total | | 150.00 | 100.00 |

Following the blending step, the powder blend demonstrated good flow properties as indicated by the Carr's Index (23.68%). The powder blend prior to compression had the following properties:

Aerated density: 0.58 g/$cm^3$

Tapped density: 0.76 g/$cm^3$

Carr's index: 23.68%

Hausner ratio: 1.31

Angle of repose: 27.96°

Blend uniformity samples were collected after blending for 10, 15 and 20 minutes of the main blending time. The composition exhibited good homogeneity at 20 minutes blend time.

Compression was performed on a Manesty F3 single punch machine using 6.5 mm NCCP tools. The mean solid core hardness was 104.3 N, the mean thickness was 3.52 mm, the friability was 0.23%, and the disintegration time was 30 seconds.

The weight of the solid cores was consistent throughout the compression run and acceptable solid cores were produced. No visual segregation was observed. Samples (10 solid cores in duplicate) were collected at start, middle and end of the compression run and sent for content uniformity testing.

Following the compression step, the solid core of the tablet was coated with Acryl-EZE II white (493Z180022) enteric coating polymer system, which was prepared as described in Manufacturing Example 1, and samples were collected after 8, 10 and 12% w/w weight gain. The coating parameters are shown in Table 11 below.

TABLE 11

| Coating parameters | |
|---|---|
| Coating Pan | Thai Coater |
| Inlet Temp | 81-90 °C |
| Exhaust Temp | 50 °C |
| Drum Speed | 18 rpm reduced to 16 rpm |
| Initial Spray Rate | 7 g/min |
| Spray Rate after 30 minutes | 11 g/min |
| Bed Temp | 35 °C |
| Inlet and exhaust Shut | Both at middle |
| Gun to Bed Distance | 5 cm (Baffles not visible) |
| Pump Speed | 05 |
| Fluid nozzle (mm) | 1.2 mm |
| Spray gun air Pressure | 10 psi |
| Fan air Pressure | 20 psi |
| Weight of Bulking inert(g) | 3000 g |
| Weight of active tablets (g) | 260 g |
| Weight of tablet bed (g) | 3260 g |
| Initial weight of 20 tablets (g) | 2.995 g |
| % w/w target for tablet coat | 8% |
| Target weight gain for 8% coating (g) | 3.235 g |
| Amount of dispersion sprayed to achieve 8% weight gain (g) | 1900 g |
| Weight of 20 tablets after 8% weight gain (g) | 3.231 g |
| % w/w target for tablet coat | 10% |
| Target weight gain for 10% coating (g) | 3.295 g |
| Amount of dispersion sprayed to achieve 10% weight gain (g) | 2400 g |
| Weight of 20 tablets after 10% weight gain (g) | 3.282 g |
| % w/w target for tablet coat | 12% |
| Target weight gain for 12% coating (g) | 3.354 g |
| Amount of dispersion sprayed to achieve 12% weight gain (g) | 2900 g |
| Weight of 20 tablets after 12% weight gain (g) | 3.362 g |

The enteric coated tablets with weight gains of 8%, 10% and 12% w/w underwent dissolution testing (500 ml dissolution media, paddle speed 75 rpm) to identify suitable levels of enteric coating. The dissolution results are presented in Table 12 below.

TABLE 12

| Dissolution results | | | | | |
|---|---|---|---|---|---|
| | Mean (% drug released) Time (min) | | | | |
| | 120 | 135 | 150 | 165 | 195 |
| | Media | | | | |
| Sample name | pH 1.0 | pH 6.8 | pH 6.8 | pH 6.8 | pH 6.8 |
| 8% w/w enteric coated tablets | 19.6 | 0* | 0* | 0* | 0* |
| 10% w/w enteric coated tablets | 00 | 55 | 74 | 86 | not determined |
| 12% w/w enteric coated tablets | 00 | 67 | 81 | 88 | 91 |

*All tablets ruptured in acid. 0% drug dissolved in pH 6.8 media as the ruptured tablets would lead to degradation in the acid stage and therefore the API was not detected in the buffer stage.

The 8% w/w weight gain enteric coated tablets failed the acid resistance test. The 10% w/w weight gain enteric coated tablets and 12% w/w weight gain enteric coated tablets demonstrated satisfactory gastric resistance and met the proposed preliminary specification of not less than 75% release in 45 minutes for enteric dosage forms.

Based on the dissolution results, it was found that 12% w/w was the optimum coating weight gain.

Formulation Example 1.4

A solid pharmaceutical composition (P66) comprising sodium meta-arsenite (SMA) as the active pharmaceutical ingredient (API) was prepared using the method described above in Manufacturing Example 1.

The composition was manufactured at a 700 g scale. Blend uniformity and content uniformity samples were collected to assess the homogeneity after the main blending time of 20 minutes.

Table 13 below provides the composition of the solid core of the tablet comprising 2.53 mg of sodium meta-arsenite (prior to the coating step).

TABLE 13

| Composition of the solid core of the P66 tablet | | | |
|---|---|---|---|
| Material | Function | mg/ tablet | % w/w |
| Sodium meta-arsenite | API | 2.53 | 1.69 |
| Dibasic calcium phosphate anhydrous (A-Comprez fine granule) | filler | 71.55 | 47.70 |
| Partially pregelatinised starch (Starch 1500) | binder, disintegrant, filler | 67.67 | 45.11 |
| Sodium starch glycolate (Explotab) | super disintegrant | 6.00 | 4.00 |
| Colloidal silicon dioxide (Aerosil 200) | glidant | 0.75 | 0.50 |
| Sodium stearyl fumarate (PRUV) | lubricant | 1.50 | 1.00 |
| Total | | 150.00 | 100.00 |

Following the blending step, the powder blend demonstrated good flow properties as indicated by the Carr's Index (25.74%). The powder blend prior to compression had the following properties:

Aerated density: 0.75 g/cm$^3$

Tapped density: 1.01 g/cm$^3$

Carr's index: 25.74%

Hausner ratio: 1.35

The powder blend compressed very well and no weight variation and/or visual segregation was observed throughout the run. High solid core hardness (87.4 N) and low friability (0.11%) were achieved, and disintegration time (2 minutes 52 seconds) was relatively rapid. The mean thickness of the solid core was 3.66 mm.

Blend uniformity samples were taken after blending for 20 minutes and content uniformity samples were collected at the start, middle and end of the compression run. Blend uniformity results exhibited excellent homogeneity with a % relative standard deviation (RSD) value of 2.1. The content uniformity of the solid cores across the compression run (start, middle and end) showed good homogeneity as a maximum acceptance value (AV) value of <6.3 was achieved (AV value of <15 is acceptable).

Following the compression step, the solid core of the tablet was coated with Acryl-EZE II white (493Z180022) enteric coating polymer system, which was prepared as described in Manufacturing Example 1. The coating parameters are shown in Table 14 below.

TABLE 14

| Coating parameters | |
|---|---|
| Parameter | Result |
| Coating pan | 15" Thai Coater |
| Inlet Temp | 90-110 °C |
| Exhaust Temp | ~50 °C |
| Drum Speed | 16 rpm |
| Spray Rate | 10-11 g/min |
| Bed Temp | ~35 °C |
| Inlet and Exhaust Shut | Both at middle |
| Gun to Bed Distance | 5 cm (Baffles not visible) |
| Fluid nozzle (mm) | 1.2 mm |
| Fan Air Pressure | 20 psi |
| Spray gun Air Pressure | 10 psi |
| Weight of Bulking inert (g) | 2600.0 g |
| Weight of active tablets (g) | 350.0 g |
| Weight of tablet bed (g) | 2950.0 g |
| Initial weight of 20 tablets (g) | 3.010 g |
| Target weight gain for 12% coating (g) | 3.371 g |
| Weight of 20 tablets after 12% weight gain (g) | 3.380 g (12.2% weight gain) |

The enteric coated tablet exhibited an acceptable dissolution profile (500 ml media, paddle speed 100 rpm). After 120 minutes, the composition was intact in acidic media (pH 1.0) with 0% API release. After 135 minutes at pH 6.8, 21% of the API was released. After 150 minutes at pH 6.8, 86% of the API was released. After 165 minutes at pH 6.8, 96% of the API was released. After 195 minutes at pH 6.8, 98% of the API was released.

The enteric coated tablet demonstrated satisfactory gastric resistance and met the proposed preliminary specification of not less than 75% release in 45 minutes for enteric dosage forms.

Manufacturing Example 2

Table 15 below provides the composition of an enteric coated tablet comprising 2.5 mg of sodium meta-arsenite as the active pharmaceutical ingredient (API). The enteric coated tablet was prepared using the method described below.

TABLE 15

| Composition of the enteric coated tablet of Manufacturing Example 2 | | | |
|---|---|---|---|
| Materials | Function | mg/ tablet | % w/w |
| Sodium meta-arsenite (SMA) | API | 2.50 | 1.67 |
| Dibasic calcium phosphate anhydrous, USP (powdered grade) | diluent, filler | 37.50 | 25.00 |
| Silicified microcrystalline cellulose (Prosolv HD90) | filler, compressible diluent | 107.00 | 71.33 |
| Sodium starch glycolate (Explotab) | super disintegrant | 1.50 | 1.00 |
| Colloidal silicon dioxide (Cab-o-sil) | glidant | 0.75 | 0.50 |
| Sodium stearyl fumarate (PRUV) | lubricant | 0.75 | 0.50 |
| Total - core: | | 150.00 | 100 |
| Acryl-EZE Green (93O11863) enteric polymer coating | Enteric coating | 16.50 | |
| Total - as a coated tablet: | | 166.50 | |

In general, and as described in detail below, the sodium meta-arsenite ("SMA") and excipients were blended together (a two-stage blending process without the use of water or solvent) to form a powder blend. The powder blend was then compressed to form the solid core of the tablet. The solid core of the tablet was then coated with an enteric coating.

Blending

The blending process described below was used for blending the ingredients.

The API and the other ingredients for the composition were dispensed and weighed. Since the concentration of the API was very low, a two-stage blending process (utilising an "API premix" and a "main mix") was utilised in an effort to improve blend uniformity.

The API was screened through a 106 μm sieve (the sieving time was about 5 to 8 minutes).

A portion of the calcium phosphate dibasic was added to the sieved API, and the resulting mixture was blended for 30 minutes to provide the "API premix".

The API premix was then blended with the remaining calcium phosphate dibasic and the other excipients (silicified microcrystalline cellulose, sodium starch glycolate, colloidal silicon dioxide, and sodium stearyl fumarate), to provide the "main mix". The main mix was blended with an intensifier bar for 4 minutes to provide a powder blend.

Compressing

The powder blend was compressed on a Key International tablet machine using 0.25 inch tooling to a target tablet weight of 150 mg±5% (range 142.5-157.5 mg). The solid cores were de-dusted.

The final solid cores demonstrated no significant friability (0.00%) and the hardness was 156.9 N (16 kp).

Enteric Coating

A 25% w/w solid content enteric coating dispersion was prepared by dispersing Acryl-EZE green powder in deionised water. The dispersion was stirred for about 30 minutes (until homogenous).

The de-dusted solid cores were spray-coated (350 g/min) with the dispersion with a weight gain of about 10 to 12% w/w. The pan speed was about 6-8 rpm. The coated tablets were dried after coating.

Example 4—Inhibitory Effect of Single Dose of SMA in LPS-Induced ARDS Model in BALB/c Mice This study evaluated the ability of substances to control acute respiratory distress syndrome (ARDS) in an ARDS model induced by intratracheal administration of LPS to *Mus musculus* (BALB/c) by measuring the level of cytokine in bronchoalveolar lavage fluid (BALF) after oral administration of SMA, the test substance, and dexamethasone, a positive control substance.

There were five groups of mice G1 to G5: (G1) a negative control; (G2) 1.03 mg/kg dose of SMA; (G3) 1.54 mg/kg dose of SMA; (G4) 2.05 mg/kg dose of SMA; and (G5) 3 mg/kg dose of the positive control substance dexamethasone. There were 10 mice in each group.

The SMA test substance was orally administered once 2 h before the induction of ARDS, and the positive control substance dexamethasone was administered orally once 1 h before the induction of ARDS.

General symptoms were observed once a day after the end of the quarantine acclimation period. The weight of the animals was measured twice before their acquisition and the start of the test. Until the end of the test, no abnormality due to the administration of the substances was observed in all groups.

At group assignment, body weight was measured for all animals, animals were randomly assigned to each group, and there was no statistical significance in body weight of the animals in all groups.

The survival analysis showed that survival was extended by the administered test substance with statistical significance (G3: $p<0.005$ (48 h post-LPS treatment); G4: $p<0.0005$ (48 h post-LPS treatment); G5: $p<0.0001$ (48 h post-LPS treatment)).

A TNF-α analysis showed that the measurements were above the limit of quantitation (LoQ) at all time points and target expression was suppressed by the administered test substance in a statistically significant manner (G4: $p<0.005$ (1 h, 2 h, 6 h, and 12 h after LPS administration); G5: $p<0.0005$ (4 h after LPS administration) and $p<0.0001$ (1 h, 2 h, 6 h, and 12 h after LPS administration)), except for LPS pre-administration (0 h) and 24 h.

An IL-6 analysis found that the measurements were above the LoQ at all time points and target expression was suppressed by the administered test substance in a statistically significant manner (G4: $p<0.05$ (2 h and 4 h after LPS administration) and $p<0.005$ (6 h and 12 h after LPS administration); G5: $p<0.05$ (1 h, 2 h, 4 h, and 24 h after LPS administration) and $p<0.0005$ (6 h after LPS administration), and $p<0.0001$ (12 h after LPS administration)), except for LPS pre-administration (0 h).

IL-1β analysis found that IL-1β measurements were above the LoQ at 4 h and 6 h, and target expression was found to be suppressed by the administered test substance in a statistically significant manner (G4: $p<0.005$ (4 h and 6 h after LPS administration); G5: $p<0.0005$ (4 h and 6 h after LPS administration)), except for LPS pre-administration (0 h), 1 h, 2 h, 12 h, and 24 h. The expression was found to be statistically significant (G4: $p<0.005$; G5: $p<0.0005$) at 12 h after LPS administration, but was excluded because the measurements were not above the LoQ.

The IFN-gamma data were excluded from the analysis due to the failure of exceeding the LoQ at all measurement points.

As a result of a GM-CSF analysis, all measured values were excluded from the analysis because they did not surpass the LoQ except for the G1 group for which measuring was conducted 6 h after LPS administration. The expression at 4 h after LPS administration was analysed as statistically significant (G2: $p<0.05$, G3: $p<0.05$, G4: $p<0.05$, G5: $p<0.05$), but was excluded because the measured values were not above the LoQ.

This study was carried out to examine the inhibitory ability of the test substance SMA on LPS-stimulated proinflammatory mediators by the administration of the test substance SMA in an ARDS model induced by repeated intratracheal administration of LPS to *Mus musculus* (BALB/c). In this study, the effect of the test substance and the positive control substance on LPS-stimulated proinflammatory mediators was evaluated in groups administered with the test substance or the positive control substance. It was found that the level of cytokine (TNF-α, IL-6, and IL-1β), known as the main mediator of ARDS, was significantly inhibited in groups administered the test substance, and in groups administered the positive control substance, when analysed using the BALF.

It was confirmed that the test substance SMA inhibits the production of LPS-stimulated TNF-α and IL-6 at a specific measurement point in a dose-dependent manner, proving the efficacy of SMA as a therapeutic agent to prevent ARDS.

In the case of IFN-gamma, GM-CSF, and IL-1β, the analytical values were excluded from the scope of the analysis by the LoQ at some measurement points, but the test substance SMA was found to inhibit the production of IL-1β dose-dependently at some measurement points.

In conclusion, SMA exerts rapid inhibitory effect on the production of proinflammatory mediators such as TNF-α, IL-6 and IL-1β, and thus can be used to extend survival by alleviating acute respiratory syndrome.

In the Figures and Tables of Example 4, SMA is referred to as "PAX-1".

4.1 Experimental Overview

This study was conducted to evaluate the ability to control acute respiratory distress syndrome (ARDS) by measuring cytokine release in bronchoalveolar lavage fluids after oral administration of SMA, the test substance, and dexamethasone, the positive control, in LPS-induced ARDS model through intratracheal administration in *Mus musculus* (BALB/c).

4.2. Study Material and Procedures 4.2.1 Test Substance

| | |
|---|---|
| Substance Name | SMA |
| Physical Property | White powder |
| Storage Condition | Store at room temperature |
| Handling Precaution | Store at room temperature until treatment |
| Special Note | Protect from light |

4.2.2 Positive Control Substance

| | |
|---|---|
| Substance Name | Dexamethasone (cat. D2915; purchased from Sigma-Aldrich Korea Inc.) |
| Physical Property | White powder |
| Storage Condition | Keep refrigerated (4 °C) |
| Handling Precaution | Store at room temperature until treatment |
| Special Note | Keep refrigerated until treatment; prepare and use on the day of treatment |

4.2.3 Vehicle

| | |
|---|---|
| Substance Name | Sterile water for injection (serial no. C4V1AF3, purchased from Dai Han Pharm Co., Ltd., KOREA) |
| Storage Condition | Room temperature |

4.2.4 Preparation of the Test Substance and Formulation Analysis

The test substance (SMA) was prepared by weighing the ingredient to the dosage concentrations of 1.03, 1.54, and 2.05 mg/kg.

4.2.5 Generation of Acute Respiratory Distress Syndrome (ARDS) Model 4.2.5.1 Inducing Substance

| | |
|---|---|
| Name | Lipopolysaccharide; LPS(O111: B4) from *Escherichia coli* (cat. L4130; purchased from Sigma-Aldrich Korea, Inc.) |
| Solubility | 5 mg/mL |

4.2.5.2 Preparation and Treatment Method

Preparation (BALF)

On the day of LPS treatment, the required volume based on the animal's body weight was prepared with the ratio of 100 μg of LPS weighed and 500 μL of water for injection added. The tube containing the mixture was sufficiently mixed using vortex mixer and kept in ice until treatment.

| Name | Composition |
|---|---|
| LPS | 1 mg |
| Water for Injection | 5 mL |
| Total volume | 5 mL |

Preparation (Survival)

On the day of LPS treatment, the required volume based on the animal's body weight was prepared by weighing 48 mg of LPS and adding 12 mL of water for injection. The tube containing the mixture was sufficiently mixed using vortex mixer and kept in ice until administration.

| Name | Composition |
|---|---|
| LPS | 48 mg |
| Water for Injection | 12 mL |
| Total volume | 12 mL |

4.2.6 Test Animal

| | |
|---|---|
| Species and Breed | BALB/cAnNTac |
| Manufacturer | DaehanBiolink co., Ltd., Korea |
| Age | 8-week old |
| D.O.B. | 2020 Feb. 10~12 (BALF) |
| D.O.B. | 2020 Apr. 1~3 (Survival) |
| Sex | Male (BALF), Female (Survival) |
| Place for Purchase | DaehanBiolink co., Ltd., Korea |

Sex, Number of Animals, Age, and Body Weight Range at the Entry (BALF) Male, 360 mice, 8-week old, 19.2 g~25.0 g Sex, Number of Animals, and Body Weight Range at the entry (Survival) Female, 60 mice, 6-week old, 18.2 g~21.3 g ARDS Induction

BALF

After measuring the body weight of mice one day after the end of a quarantine acclimation period, 50 μL of LPS mixture was loaded using a disposable pipette tip, and forced administration of 10 μg/50 μL/head was performed into the already-anesthetized mice through intra trachea. The mice were checked while they recovered from anesthesia after the administration. The mice were treated with LPS two times, and the treatments were performed on Day 1 and Day 5. Treated mice were observed for general symptoms once daily.

Survival

After measuring the body weight one day after the completion of the quarantine acclimation period, the LPS mixture was injected using a disposable syringe (1 mL, 26 G) into the peritoneal at a concentration of 20 mg/kg. Treated mice were observed every hour for general symptoms and checked for dead mice.

Group Assignment

BALF

Of the primary LPS-treated mice, those without health problems prior to the secondary administration (boosting) were group separated into a total of 5 groups with 70 mice per group as evenly as possible based on the body weight of each group.

Survival

After the quarantine acclimation period, animals without abnormality were group separated into a total 5 groups with 10 mice per group as evenly as possible based on the body weight of each group.

4.2.7 Treatment

| Route of Treatment | |
|---|---|
| Study Substance: | Oral (forced administration into the stomach) |
| LPS (BALF): | Forced administration into the bronchial tubes (intratracheal injection) |
| LPS (Survival): | Intraperitoneal |

Treatment Method and Frequency

| Treatment was done once using a disposable syringe (BD 1 ml syringe, cat.: REF301321, Lot: 9326990 BD, U.S.A.), and each study substance was treated based on the time it took to induce acute respiratory distress syndrome (LPS treatment). | |
|---|---|
| SMA (Test Substance) | Before 2 hours |
| Dexamethasone (Positive Control Substance) | Before 1 hour |

4.2.8 Group Composition and Treatment Dose 4.2.8.1 Group Composition (BALF)

| | Group | BALF sampling time points | Treatment Dose (mg/kg) | Treatment Volume (mL/kg) | No. of Animals* (Entity No.) |
|---|---|---|---|---|---|
| G1 | Negative control | Prior to LPS treatment | 0 | 10 | 70 (2101~2170) |
| G2 | SMA (low) | (0 h) 1 h, 2 h, 4 h, | 1.03 | 10 | 70 (2201~2270) |
| G3 | SMA (middle) | 6 h, 12 h and 24 h | 1.54 | 10 | 70 (2301~2370) |
| G4 | SMA (high) | (Total 7 times) | 2.05 | 10 | 70 (2401~2470) |
| G5 | Dexamethasone | | 3 | 10 | 70 (2501~2570) |

*BALF sampling was composed of 10 mice per group, and it's performed 7 times with total 70 mice.

4.2.8.2 Group Composition (Survival)

| | Group | LPS (mg/kg) | Treatment Dose (mg/kg) | Treatment Volume (mL/kg) | No. of Animals (Entity No.) |
|---|---|---|---|---|---|
| G1 | Negative control | 20 | 0 | 10 | 10 (2101~2110) |
| G2 | SMA (low) | 20 | 1.03 | 10 | 10 (2201~2210) |
| G3 | SMA (middle) | 20 | 1.54 | 10 | 10 (2301~2310) |
| G4 | SMA (high) | 20 | 2.05 | 10 | 10 (2401~2410) |
| G5 | Dexamethasone | 20 | 3 | 10 | 10 (2501~2510) |

4.2.8.3 Set-up of Treatment Dose

The treatment dose of test substance (SMA) was planned to be 5, 7.5, and 10 mg, which will be applied at clinical setting for healthy adult weighing 60 kg. Human equivalent dose (HED) was calculated by a calculation method from FDA guideline* using the body surface area, and by substituting to adjust body surface area of test animal (mouse), it was set-up to 1.03, 1.54, and 2.05 mg/kg.

Extracted from Guidance for industry, estimating the maximum safe starting dose in initial clinical trials for therapeutics in adult healthy volunteers

| Conversion of animal dose to human equivalent dose (HED) based on body surface area | | | |
|---|---|---|---|
| | To convert animal dose in mg/kg to | To convert animal dose in mg/kg to HED* in mg/kg, either: | |
| Species | dose in mg/m$^2$, multiply by $k_m$ | Divide animal dose by | Multiply animal dose by |
| Human | 37 | — | — |
| mouse | 3 | 12.3 | 0.08 |

*based on adult weighing 60 kg 4.2.9 Observation and Body Weight Measurement

Observation of General Symptoms

During the observation period, general symptoms such as appearance, behaviour and faeces once daily, and dead animals were checked.

Disposal of the Dead Animals

During the observation period, total 8 cases of death occurred, and those were excluded from the analysis.

Body Weight Measurement

Body weight was measured on the day of cell-line transplant, once a week, and on the day of sacrifice. If body weight was measured on the day of treatment, it was measured prior to the administration.

4.2.10 BALF Sampling and Cytokine Analysis

Sampling of Bronchoalveolar Lavage Fluid; BALF

The respiratory tract of anesthetized entity using anesthetic was incised, bronchi was exposed, and a disposable 22 G catheter (BD, Cat.: REF382423, U.S.A.) was inserted into a bronchus. Inserted catheter and bronchus were sutured (AILEE, Cat.: SK521, Lot: 7908772U, KOREA) for fixation to prevent infusion leakage, the interior of the lungs was washed through the catheter slowly twice with 600 µL PBS (welgene, Cat.: ML008-01, Lot: ML08200201, KOREA) loaded in a disposable syringe (BD 1 ml syringe, BD, Cat.: REF301321, Lot: 9326990, U.S.A.), and the lavage was transferred to a microtube (SPL, Cat.: 60015, Lot: LAOC16A60015, KOREA). Transferred BALF (lung lavage) was immediately centrifuged (Hanil, HI_SM-13/A2.0, KOREA) to separate cells and supernatant, and the supernatant was transferred to a new tube and stored after flash freezing using liquid nitrogen in deep freezer until cytokine analysis.

Cytokine Analysis

| Sample for analysis | Target | Method of Analysis |
|---|---|---|
| BALF | IL-1β, IL-6, TNF-α, GM-CSF, IFN-gamma | Multiplex |
| | iNOS, COX-2, NF-kB | ELISA* |

*Analysis Kit was supplied 4.2.11 Survival Analysis

Dead animals were checked every hour until 24 h after LPS treatment and at 48 h.

4.2.12 Statistical Analysis of Data

The analytical result of cytokines from bronchoalveolar lavage fluids (BALF) obtained from the study was conducted using Prism (Graphpad, version 7).

The equal variance test was performed using D'Agostino-pearson omnibus normality test. As the analytical results of the samples, except for body weight data, were lacking in sample quantity, the equal variance test was rejected. For body weight analysis, if equivariant, one-way analysis of variance (ANOVA; significance level: 0.05) was performed and if significance was observed, multiple tests of Dunnett's t-test was performed to confirm the significance between each test group (G2-G5) against the negative control group (G1) (significance level: one-sided 0.05 and 0.01). As tests were rejected for several body weight measurement time-point and the analytical result of cytokines, the Kruskal-Wallis test (significance level: 0.05) was performed, and if significance was observed, multiple tests of Dunns' test was performed to confirm the significance between each test group (G2-G5) against negative control group (G1) (significance level: one-sided 0.05 and both-sided 0.1).

For the results on the survival analysis, Log-rank (Mantel-Cox) test was performed to confirm the significance between each test group (G2-G5) against negative control group (G1) (significance level: one-sided 0.05 and both-sided 0.1).

Figure 13:
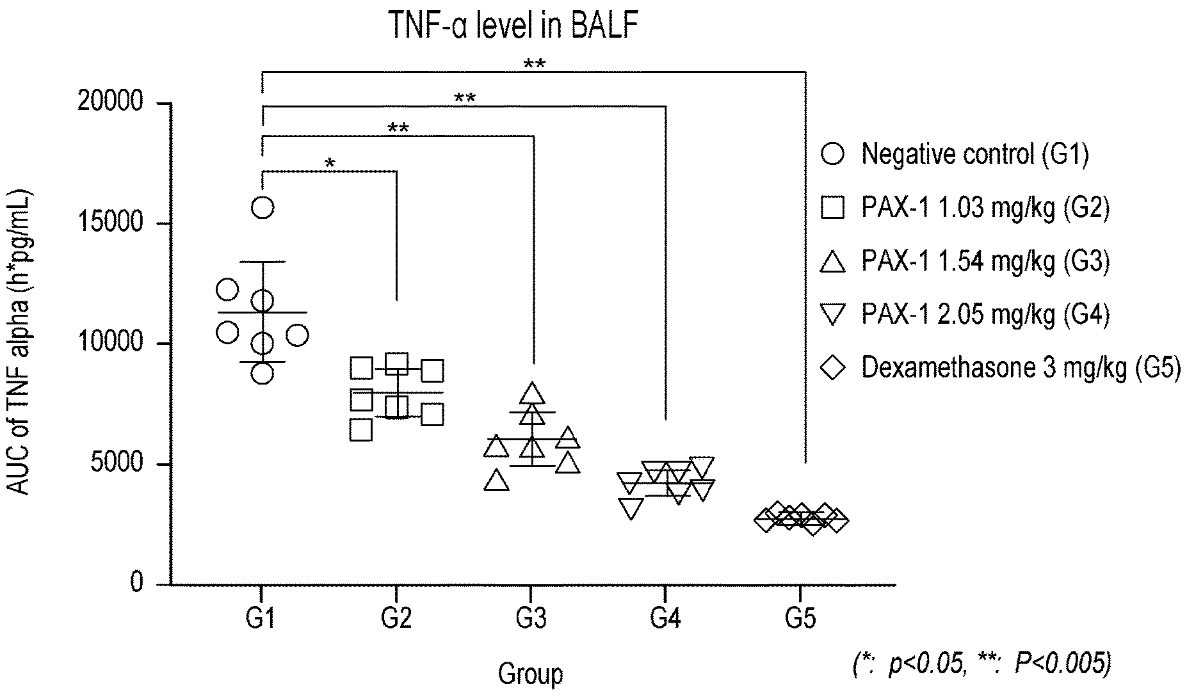
FIG. 13 is a graph showing the AUC (area under the curve) value for TNF-α levels in bronchoalveolar lavage fluid from an ARDS mouse model following treatment with PAX-1 (SMA), dexamethasone or no treatment. Data presented as mean±95% confidence interval (*: p<0.05, **: P<0.005)
Figure 14:
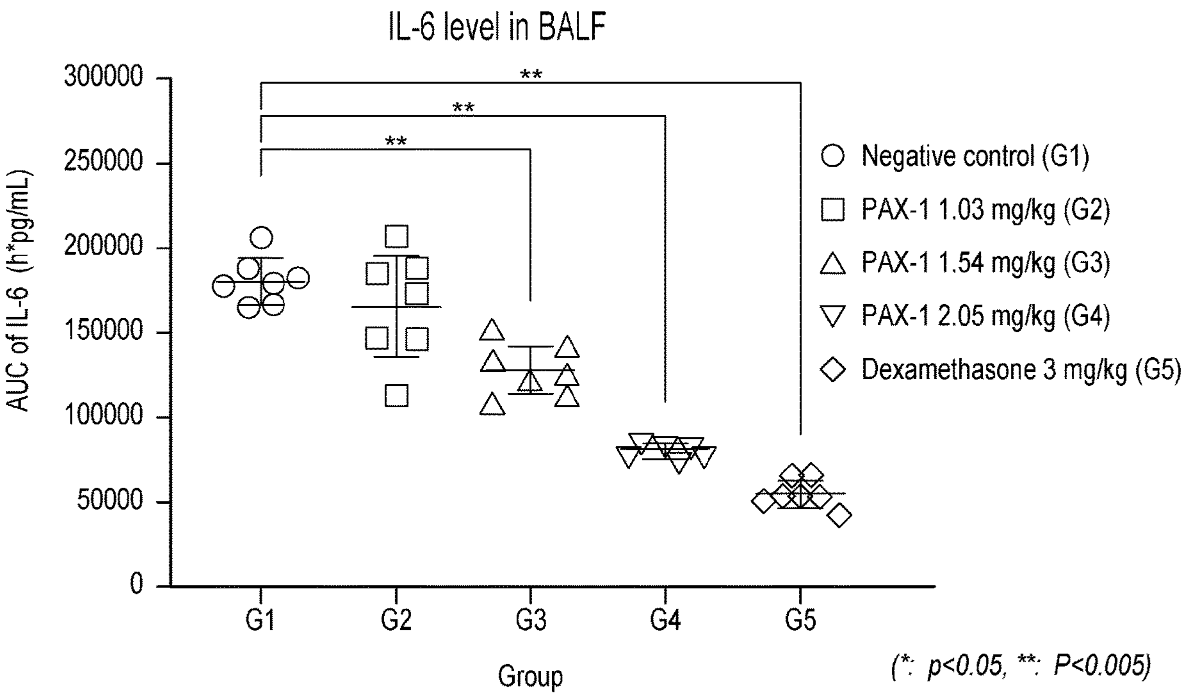
FIG. 14 is a graph showing the AUC (area under the curve) value for IL-6 levels in bronchoalveolar lavage fluid from an ARDS mouse model following treatment with PAX-1 (SMA), dexamethasone or no treatment. Data presented as mean±95% confidence interval (*: p<0.05, **: P<0.005)
Figure 15:
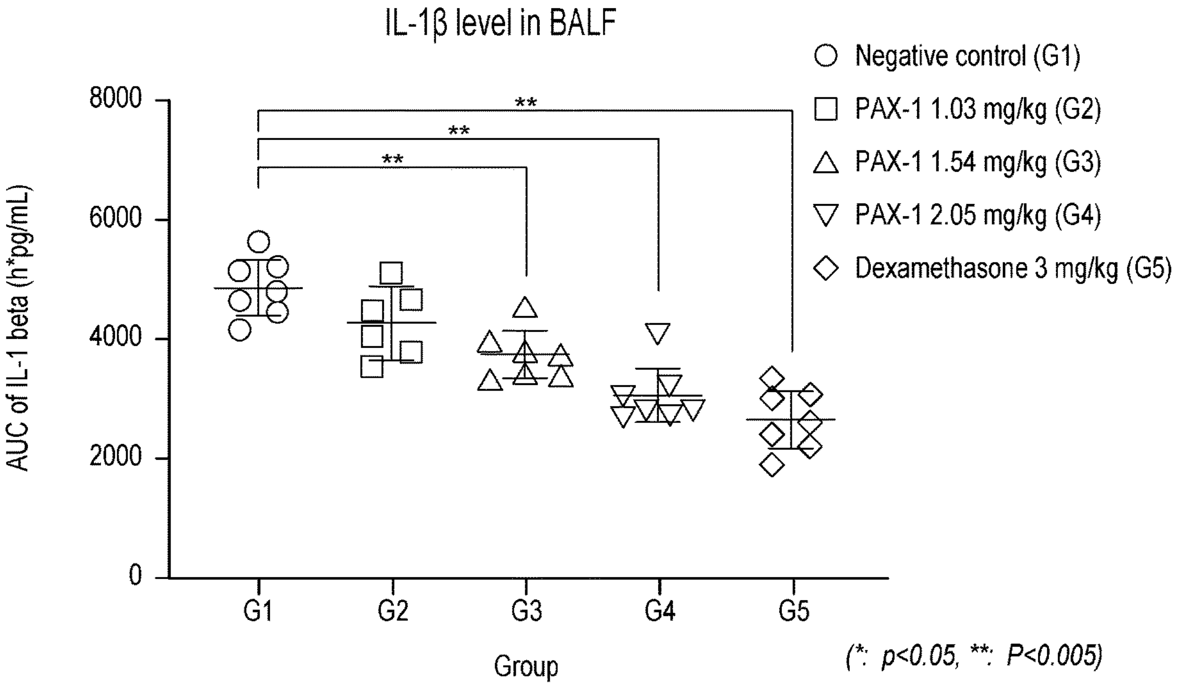
FIG. 15 is a graph showing the AUC (area under the curve) value for IL-1β levels in bronchoalveolar lavage fluid from an ARDS mouse model following treatment with PAX-1 (SMA), dexamethasone or no treatment. Data presented as mean±95% confidence interval (*: p<0.05, **: P<0.005)

4.3. Results and Discussion 4.3.1 Evaluation of Cytokine Production and Inhibition 4.3.1.1. Analysis of Cytokine Production (FIG. 13-15, Tables 16-19)

Multiplex (Luminex, Austin, TX, USA) was used for the analysis of TNF-α, IL6, IL-1β, IFN-gamma and GM-CSF, which measures median fluorescent intensity (MFI). By sorting each sample by groups and BALF-acquired time points, a total of 7 sets was used for analysis and it was designed to assign one sample from each group per set.

All analysis was computed by substituting measured MFI value with the standard curve formula of each set calculated from quartic polynomial. $R^2$ value of standard value was confirmed to be 1 in all analysis, and measured data were confirmed to be highly credible.

Those samples excluded from the analysis due to limit of quantification were diluted using the reagent from the study protocol.

Since the dilution ratio was applied to analyse LPS-stimulated high-level cytokine release, it was confirmed that those with low values were measured below the limit of quantification and included as inaccurate measurement. Although these were excluded from the analysis due to amplification as per the dilution ratio, the Tables and Figures have been generated including all data.

Analysis of TNF-α (FIG. 13, Table 16)

The expression of TNF-α in all groups was measured to be 2 pg/mL and 11~12 pg/mL in pre-LPS treatment (0 h) and 24 h analysis. However, it was excluded from the data analysis because it was below the limit of quantification of MFI. Analysis was conducted for 1 h, 2 h, 6 h and 12 h post-LPS treatment.

TABLE 16

| Summary of mean TNF-α level in BALF | | | | | | | | |
|---|---|---|---|---|---|---|---|---|
| Group/ Dose | | TNF-alpha in BALF (pg/mL) Time after administration (hours) | | | | | | |
| (mg/kg) | | 0 | 1 | 2 | 4 | 6 | 12 | 24 |
| G1 | Mean | 2 | 1,997 | 1,417 | 1,036 | 735 | 249 | 11 |
| 0 | S.D. | 0 | 578 | 315 | 454 | 188 | 23 | 2 |
| | N | 7 | 7 | 7 | 7 | 7 | 7 | 7 |
| G2 | Mean | 2 | 1,303 | 1,004 | 794 | 502 | 174 | 12 |
| 1.03 | S.D. | 0 | 225 | 377 | 187 | 188 | 21 | 2 |
| | N | 7 | 7 | 7 | 7 | 7 | 7 | 7 |
| G3 | Mean | 2 | 1,062 | 707 | 611 | 407 | 120 | 12 |
| 1.54 | S.D. | 0 | 445 | 227 | 297 | 49 | 17 | 2 |
| | N | 7 | 7 | 7 | 7 | 7 | 7 | 7 |
| G4 | Mean | 2 | 729 | 559 | 539 | 303 | 38 | 12 |
| 2.05 | S.D. | 0 | 139 | 60 | 137 | 111 | 5 | 2 |
| | N | 7 | 7## | 7## | 7 | 7## | 7## | 7 |

TABLE 16-continued

| Summary of mean TNF-α level in BALF | | | | | | | | |
|---|---|---|---|---|---|---|---|---|
| Group/ Dose | | TNF-alpha in BALF (pg/mL) Time after administration (hours) | | | | | | |
| (mg/kg) | | 0 | 1 | 2 | 4 | 6 | 12 | 24 |
| G5 | Mean | 2 | 508 | 394 | 338 | 204 | 23 | 11 |
| 3 | S.D. | 0 | 140 | 87 | 48 | 24 | 5 | 2 |
| | N | 7 | $7^{\#\#\#\#}$ | $7^{\#\#\#\#}$ | $7^{\#\#\#}$ | $7^{\#\#\#\#}$ | $7^{\#\#\#\#}$ | 7 |

G1 (Negative control, 0 mg/kg), G2 (PAX-1, 1.03 mg/kg), G3 (PAX-1, 1.54 mg/kg), G4 (PAX-1, 2.05 mg/kg), G5 (Dexamethasone, 3 mg/kg)
Each point represents the mean + S.D. (n = 7)
$^{\#\#}p < 0.005$, Significant difference from the negative control (G1) by Dunn's test
$^{\#\#\#}p < 0.0005$, Significant difference from the negative control (G1) by Dunn's test
$^{\#\#\#\#}p < 0.0001$, Significant difference from the negative control (G1) by Dunn's test
Result of 0 h and 24 h were excluded because of limit of quantification.
N: Number of animals The change in TNF-α production in the negative control group (G1) started from 1,997 pg/mL, and then 1,417 pg/mL, 1,036 pg/mL, 735 pg/mL and 249 pg/mL; it was observed that LPS-induced TNF-α production increased and then decreased in a time-dependent manner.

The change in TNF-α production in the group treated with 1.03 mg/kg of SMA (G2) was 1,303 pg/mL, 1,004 pg/mL, 794 mg/mL, 502 pg/mL and 174 pg/mL. It was observed that LPS-induced TNF-α production increased and then decreased in a time-dependent manner; however, there was no statistical significance ($p<0.05$) when its time-dependent TNF-α production was compared with that of the negative control group (G1).

The change in TNF-α production in the group treated with 1.54 mg/kg of SMA (G3) was 1,062 pg/mL, 707 pg/mL, 611 pg/mL, 407 pg/mL and 120 pg/mL. It was observed that LPS-induced TNF-α production increased and then decreased in a time-dependent manner; however, there was no statistical significance ($p<0.05$) when its time-dependent TNF-α production was compared with that of the negative control group (G1).

The change in TNF-α production in the group treated with 2.05 mg/kg of SMA (G4) was 729 pg/mL, 559 pg/mL, 539 pg/mL, 303 pg/mL and 38 pg/mL. It was observed that LPS-induced TNF-α production increased and then decreased in a time-dependent manner, and at some timepoints, its TNF-α values were statistically significant ($p<0.005$: 1 h, 2 h, 6 h and 12 h) when compared with that of the negative control group (G1).

The change in TNF-α production in the group treated with 3 mg/kg of the positive control substance, dexamethasone (G5) was 508 pg/mL, 394 pg/mL, 338 pg/mL, 204 pg/mL and 23 pg/mL. It was observed that LPS-induced TNF-α production increased and then decreased in a time-dependent manner, and at some timepoints, its TNF-α values were statistically significant ($p<0.0005$: 4 h, $p<0.0001$: 1 h, 2 h, 6 h, 12 h) when compared with that of the negative control group (G1).

The change in TNF-α production in all groups (G1-G5) were plotted on a graph over time (data not shown), from which the overall reduction of TNF-α was accessed by calculating the AUC (area under the curve) value for each group (FIG. 13). Statistically significant decrease in TNF-α production was evident in all groups treated with SMA or dexamethasone ($p<0.005$: G2-G5) compared to the negative control group (G1). Table 19 below provides the numerical values and statistical analyses of the AUC values for each group of drug treatment.

Analysis of IL-6 (FIG. 14, Table 17)

In the analysis prior to LPS treatment (0 h), the expression of IL-6 in all groups was measured to be 12~13 pg/mL. However, as these values were below the limit of quantification of MFI, they are excluded from the data analysis, and the data from 1 h, 2 h, 4 h, 6 h, 12 h and 24 h post-LPS treatment were used for analysis.

TABLE 17

| Summary of mean IL-6 level in BALF | | | | | | | | |
|---|---|---|---|---|---|---|---|---|
| Group/ Dose | | IL-6 in BALF (pg/mL) Time after administration (hours) | | | | | | |
| (mg/kg) | | 0 | 1 | 2 | 4 | 6 | 12 | 24 |
| G1 | Mean | 13 | 3,663 | 10,238 | 13,015 | 10,298 | 8,169 | 3,513 |
| 0 | S.D. | 3 | 1,062 | 2,529 | 2,255 | 1,692 | 1,021 | 1,496 |
| | N | 7 | 7 | 7 | 7 | 7 | 7 | 7 |
| G2 | Mean | 13 | 2,984 | 10,188 | 12,871 | 8,954 | 7,276 | 3,402 |
| 1.03 | S.D. | 3 | 332 | 3,985 | 3,450 | 1,714 | 2,255 | 1,249 |
| | N | 7 | 7 | 7 | 7 | 7 | 7 | 7 |
| G3 | Mean | 13 | 3,152 | 7,107 | 9,842 | 6,814 | 5,094 | 3,623 |
| 1.54 | S.D. | 3 | 610 | 2,473 | 2,427 | 1,075 | 1,541 | 936 |
| | N | 7 | 7 | 7 | 7 | 7 | 7 | 7 |
| G4 | Mean | 13 | 2,193 | 4,701 | 8,209 | 4,341 | 2,629 | 2,096 |
| 2.05 | S.D. | 3 | 764 | 2,376 | 2,321 | 798 | 652 | 335 |
| | N | 7 | 7 | $7^{\#}$ | $7^{\#}$ | $7^{\#\#}$ | $7^{\#\#}$ | 7 |
| G5 | Mean | 12 | 2,172 | 4,411 | 7,727 | 2,064 | 1,294 | 1,804 |
| 3 | S.D. | 2 | 416 | 770 | 2,308 | 274 | 467 | 550 |
| | N | 7 | $7^{\#}$ | $7^{\#}$ | $7^{\#}$ | $7^{\#\#\#}$ | $7^{\#\#\#\#}$ | $7^{\#}$ |

G1 (Negative control, 0 mg/kg), G2 (PAX-1, 1.03 mg/kg), G3 (PAX-1, 1.54 mg/kg), G4 (PAX-1, 2.05 mg/kg), G5 (Dexamethasone, 3 mg/kg)
Each point represents the mean + S.D. (n = 7)
$^{\#}p < 0.05$. Significant difference from the negative control (G1) by Dunn's test
$^{\#\#}p < 0.005$, Significant difference from the negative control (G1) by Dunn's test
$^{\#\#\#}p < 0.0005$, Significant difference from the negative control (G1) by Dunn's test
$^{\#\#\#\#}p < 0.0001$, Significant difference from the negative control (G1) by Dunn's test
Result of 0 h was excluded because of limit of quantification.
N: number of animals The change in IL-6 production in the negative control group (G1) started from 3,663 pg/mL, and then 10,238 pg/mL, 13,015 pg/mL, 10,298 pg/mL, 8,169 pg/mL and 3,513 pg/mL; it was observed that LPS-induced IL-6 production increased and then decreased in a time-dependent manner.

The change in IL-6 production in the group treated with 1.03 mg/kg of SMA (G2) was 2,984 pg/mL, 10,188 pg/mL, 12,871 pg/mL, 8,954 pg/mL, 7,276 pg/mL and 3,402 pg/mL. It was observed that LPS-induced IL-6 production increased and then decreased in a time-dependent manner; however, there was no statistical significance ($p<0.05$) when its time-dependent IL-6 production was compared to that of the negative control group (G1).

The change in IL-6 production in the group treated with 1.54 mg/kg of SMA (G3) was 3,152 pg/mL, 7,107 pg/mL, 9,842 pg/mL, 6,814 pg/mL, 5,094 pg/mL and 3,623 pg/mL. It was observed that LPS-induced IL-6 production increased and then decreased in a time-dependent manner; however, there was no statistical significance ($p<0.05$) when its time-dependent IL-6 production was compared with that of the negative control group (G1).

The change in IL-6 production in the group treated with 2.05 mg/kg of SMA (G4) was 2,193 pg/mL, 4,701 pg/mL, 8,209 pg/mL, 4,341 pg/mL, 2,629 pg/mL and 2,096 pg/mL. It was observed that LPS-induced IL-6 production increased and then decreased in a time-dependent manner, and at some timepoints, its IL-6 values were statistically significant ($p<0.05$: 2 h and 4 h, $p<0.005$: 6 h and 12 h) when compared with that of the negative control group (G1).

The change in IL-6 production in the group treated with 3 mg/kg of the positive control substance, dexamethasone (G5) was 2,172 pg/mL, 4,411 pg/mL, 7,727 pg/mL, 2,064 pg/mL, 1,294 pg/mL and 1,804 pg/mL. It was observed that LPS-induced IL-6 production increased and then decreased in a time-dependent manner, and at some timepoints, its IL-6 values were statistically significant ($p<0.05$: 1 h, 2 h, 4 h and 24 h, $p<0.0005$: 6 h, $p<0.0001$: 12 h) when compared with that of the negative control group (G1).

The change in IL-6 production in all groups (G1-G5) were plotted on a graph over time (data not shown), from which the overall reduction of IL-6 was accessed by calculating the AUC (area under the curve) value for each group (FIG. 14). Statistically significant decrease in IL-6 production was evident in some groups treated with SMA or dexamethasone ($p<0.005$: G3, G5) compared to the negative control group (G1). Table 19 below provides the numerical values and statistical analyses of the AUC values for each group of drug treatment.

Analysis of IL-1β (FIG. 15, Table 18)

In the analysis of pre-LPS treatment (0 h), and 1 h, 2 h, and 24 h post-LPS treatment, the expression of IL-1β in all groups was measured to be 203-295 pg/mL. However, as these values are below the limit of quantification of MFI, they have been excluded from the data analysis, and the data from 4 h, 6 h, and 12 h post-LPS treatment were used for analysis.

TABLE 18

Summary of mean IL-1β level in BALF

| Group/Dose (mg/kg) | | IL-1 beta in BALF (pg/mL) Time after administration (hours) 0 | 1 | 2 | 4 | 6 | 12 | 24 |
|---|---|---|---|---|---|---|---|---|
| G1 | Mean | 212 | 210 | 246 | 510 | 686 | 414 | 295 |
| 0 | S.D. | 16 | 15 | 24 | 46 | 77 | 17 | 28 |
| | N | 7 | 7 | 7 | 7 | 7 | 7 | 7 |
| G2 | Mean | 215 | 210 | 249 | 468 | 600 | 405 | 294 |
| 1.03 | S.D. | 13 | 15 | 29 | 49 | 37 | 34 | 25 |
| | N | 7 | 7 | 7 | 7 | 7 | 7 | 7 |
| G3 | Mean | 209 | 205 | 256 | 413 | 517 | 382 | 285 |
| 1.54 | S.D. | 14 | 14 | 25 | 48 | 18 | 16 | 32 |
| | N | 7 | 7 | 7 | 7 | 7 | 7 | 7 |
| G4 | Mean | 212 | 203 | 251 | 374 | 483 | 335 | 288 |
| 2.05 | S.D. | 14 | 9 | 24 | 31 | 36 | 15 | 26 |
| | N | 7 | 7 | 7 | $7^{\#\#}$ | $7^{\#\#}$ | $7^{\#\#}$ | 7 |
| G5 | Mean | 208 | 210 | 241 | 350 | 458 | 318 | 258 |
| 3 | S.D. | 12 | 19 | 23 | 30 | 37 | 28 | 25 |
| | N | 7 | 7 | 7 | $7^{\#\#\#}$ | $7^{\#\#\#}$ | $7^{\#\#\#}$ | 7 |

G1 (Negative control, 0 mg/kg), G2 (PAX-1, 1.03 mg/kg), G3 (PAX-1, 1.54 mg/kg), G4 (PAX-1, 2.05 mg/kg), G5 (Dexamethasone, 3 mg/kg)
Each point represents the mean + S.D. (n = 7)
$^{\#\#}p < 0.005$, Significant difference from the negative control (G1) by Dunn's test
$^{\#\#\#}p < 0.0005$, Significant difference from the negative control (G1) by Dunn's test
Result of 0 h, 1 h, 2 h and 24 h were excluded because of limit of quantification.
N: number of animals The change in IL-1β production in the negative control group (G1) started from 510 pg/mL, and then 686 pg/mL and 414 pg/mL. It was observed that LPS-induced IL-1β production increased and then decreased in a time-dependent manner.

The change in IL-1β production in the group treated with 1.03 mg/kg of SMA (G2) was 468 pg/mL, 600 pg/mL and 405 pg/mL. It was observed that LPS-induced IL-1β production increased and then decreased in a time-dependent manner; however, there was no statistical significance ($p<0.05$) when its time-dependent IL-1β production was compared with that of the negative control group (G1).

The change in IL-1β production in the group treated with 1.54 mg/kg of SMA (G3) was 413 pg/mL, 517 pg/mL and 382 pg/mL. It was observed that LPS-induced IL-1β production increased and then decreased in a time-dependent manner; however, there was no statistical significance ($p<0.05$) when its time-dependent IL-1β production was compared with that of the negative control group (G1).

The change in IL-1β production in the group treated with 2.05 mg/kg of SMA (G4) was 374 pg/mL, 483 pg/mL, and 335 pg/mL. It was observed that LPS-induced IL-1β production increased and then decreased in a time-dependent manner, and at some timepoints, its IL-1β values were statistically significant ($p<0.005$: 4 h, 6 h and 12 h) when compared with that of the negative control group (G1).

The change in IL-1β production in the group treated with 3 mg/kg of the positive control substance, dexamethasone (G5) was 350 pg/mL, 458 pg/mL and 318 pg/mL. It was observed that LPS-induced IL-1β production increased and then decreased in a time-dependent manner, and at some timepoints, its IL-1β values were statistically significant ($p<0.0005$: 4 h, 6 h and 12 h) when compared with that of the negative control group (G1).

The change in IL-1β production in all groups (G1-G5) were plotted on a graph over time (data not shown), from which the overall reduction of IL-1β was accessed by calculating the AUC (area under the curve) value for each group (FIG. 15). Statistically significant decrease in IL-1β production was evident in some groups treated with SMA or dexamethasone ($p<0.005$: G3, G5) compared to the negative control group (G1). Table 19 below provides the numerical values and statistical analyses of the AUC values for each group of drug treatment.

TABLE 19

Summary of cytokine parameter

| Cytokine | Group | Treatment | Mean AUC+ (h*pg/mL) | p-value* |
|---|---|---|---|---|
| TNF-alpha (FIG. 13) | G1 | Negative control (n = 7) | 11390.1 | |
| | G2 | PAX-1 1.03 mg/kg (n = 7) | 7984.4 | 0.0073 |
| | G3 | PAX-1 1.54 mg/kg (n = 7) | 6064.8 | 0.0022 |
| | G4 | PAX-1 2.05 mg/kg (n = 7) | 4215.8 | 0.0022 |
| | G5 | Dexamethasone 3 mg/kg (n = 7) | 2815.4 | 0.0022 |
| IL-6 (FIG. 14) | G1 | Negative control (n = 7) | 180548.1 | |
| | G2 | PAX-1 1.03 mg/kg (n = 7) | 165404.0 | 0.6093 |
| | G3 | PAX-1 1.54 mg/kg (n = 7) | 128034.8 | 0.0022 |
| | G4 | PAX-1 2.05 mg/kg (n = 7) | 78963.1 | 0.0022 |
| | G5 | Dexamethasone 3 mg/kg (n = 7) | 54684.9 | 0.0022 |
| IL-1 beta (FIG. 15) | G1 | Negative control (n = 7) | 4866.3 | |
| | G2 | PAX-1 1.03 mg/kg (n = 6) | 4272.9 | 0.1004 |
| | G3 | PAX-1 1.54 mg/kg (n = 7) | 3738.3 | 0.0049 |
| | G4 | PAX-1 2.05 mg/kg (n = 7) | 3045.8 | 0.0022 |
| | G5 | Dexamethasone 3 mg/kg (n = 7) | 2637.5 | 0.0022 |

+Baseline-adjusted
*Wilcoxon rank sum test, compared to negative control

Analysis of IFN-gamma

Analysis of IFN-gamma was excluded from the data analysis because its MFI was below the limit of quantification at all timepoints.

Analysis of GM-CSF

Analysis of GM-CSF was excluded from the data analysis because its MFI was below the limit of quantification at all timepoints.

4.3.1.2 Analysis of Production Rate

Standardizing negative control group as 100%, the inhibitory rate of cytokine production of groups treated with test substance and positive control substance was calculated.

Analysis of TNF-α

The production rate analysis on TNF-α was performed with data from 1 h, 2 h, 4 h, 6 h, and 12 h, and those from 0 h and 24 h were excluded.

The inhibitory rate of TNF-α production was 65%, 71%, 77%, 68%, and 70% in the group treated with 1.03 mg/kg of SMA (G2), and no significant difference ($p<0.05$) was observed from all statistical analysis.

The inhibitory rate of TNF-α production was 53%, 50%, 59%, 55%, and 48% in the group treated with 1.54 mg/kg of SMA (G3), and no significant difference ($p<0.05$) was observed from all statistical analysis.

The inhibitory rate of TNF-α production was 37%, 39%, 52%, 41%, and 15% in the group treated with 2.05 mg/kg of SMA (G4). At some timepoints, it was observed that the reducing effect of SMA was statistically significant ($p<0.005$: 1 h, 2 h, 6 h, and 12 h).

The inhibitory rate of TNF-α production was 25%, 28%, 33%, 28%, and 9% in the group treated with 3 mg/kg of dexamethasone, a positive control substance (G5). At some timepoints, it was observed that the reducing effect of dexamethasone was statistically significant ($p<0.0005$: 4 h, $p<0.0001$: 1 h, 2 h, 6 h and 12 h).

Analysis of IL-6

The production rate analysis on IL-6 was performed with data from 1 h, 2 h, 4 h, 6 h, 12 h and 24 h, and those from 0 h were excluded.

The inhibitory rate of IL-6 production was 81%, 100%, 99%, 87%, 89% and 97% in the group treated with 1.03 mg/kg of SMA (G2), and no significant difference ($p<0.05$) was observed from all statistical analysis.

The inhibitory rate of IL-6 production was 86%, 69%, 76%, 66%, 62%, and 103% in the group treated with 1.54 mg/kg of SMA (G3), and no significant difference ($p<0.05$) was observed from all statistical analysis.

The inhibitory rate of IL-6 production was 60%, 46%, 63%, 42%, 32%, and 60% in the group treated with 2.05 mg/kg of SMA (G4). At some timepoints, it was observed that the reducing effect of SMA was statistically significant ($p<0.05$: 2 h and 4 h, $p<0.005$: 6 h and 12 h).

The inhibitory rate of IL-6 production was 59%, 43%, 59%, 20%, 16%, and 51% in the group treated with 3 mg/kg of dexamethasone, a positive control substance (G5). At some timepoints, it was observed that the reducing effect of dexamethasone was statistically significant ($p<0.05$: 1 h, 2 h, 4 h, and 24 h, $p<0.0001$: 6 h and 12 h).

Analysis of IL-1β

The production rate analysis on IL-1β was performed with data from 4 h, 6 h, and 12 h, and those from 0 h, 1 h, 2 h, and 24 h were excluded.

The inhibitory rate of IL-1β production was 92%, 87%, and 98% in the group treated with 1.03 mg/kg of SMA (G2), and no significant difference ($p<0.05$) was observed from all statistical analysis.

The inhibitory rate of IL-1β production was 81%, 75%, and 92% in the group treated with 1.54 mg/kg of SMA (G3), and no significant difference ($p<0.05$) was observed from all statistical analysis.

The inhibitory rate of IL-1β production was 73%, 70%, and 81% in the group treated with 2.05 mg/kg of SMA (G4). At some timepoints, it was observed that the reducing effect of SMA was statistically significant ($p<0.05$: 4 h, 6 h, and 12 h).

The inhibitory rate of IL-1β production was 69%, 67%, and 77% in the group treated with 3 mg/kg of dexamethasone, a positive control substance (G5). At some timepoints, it was observed that the reducing effect of dexamethasone was statistically significant ($p<0.0001$: 4 h, 6 h, and 24 h).

Analysis of IFN-Gamma

The analysis of IFN-gamma was excluded from the production rate analysis because its MFI was below the limit of quantification at all timepoints.

Analysis of GM-CSF

The analysis of GM-CSF was excluded from the production rate analysis because its MFI was below the limit of quantification at all timepoints.

Figure 16:
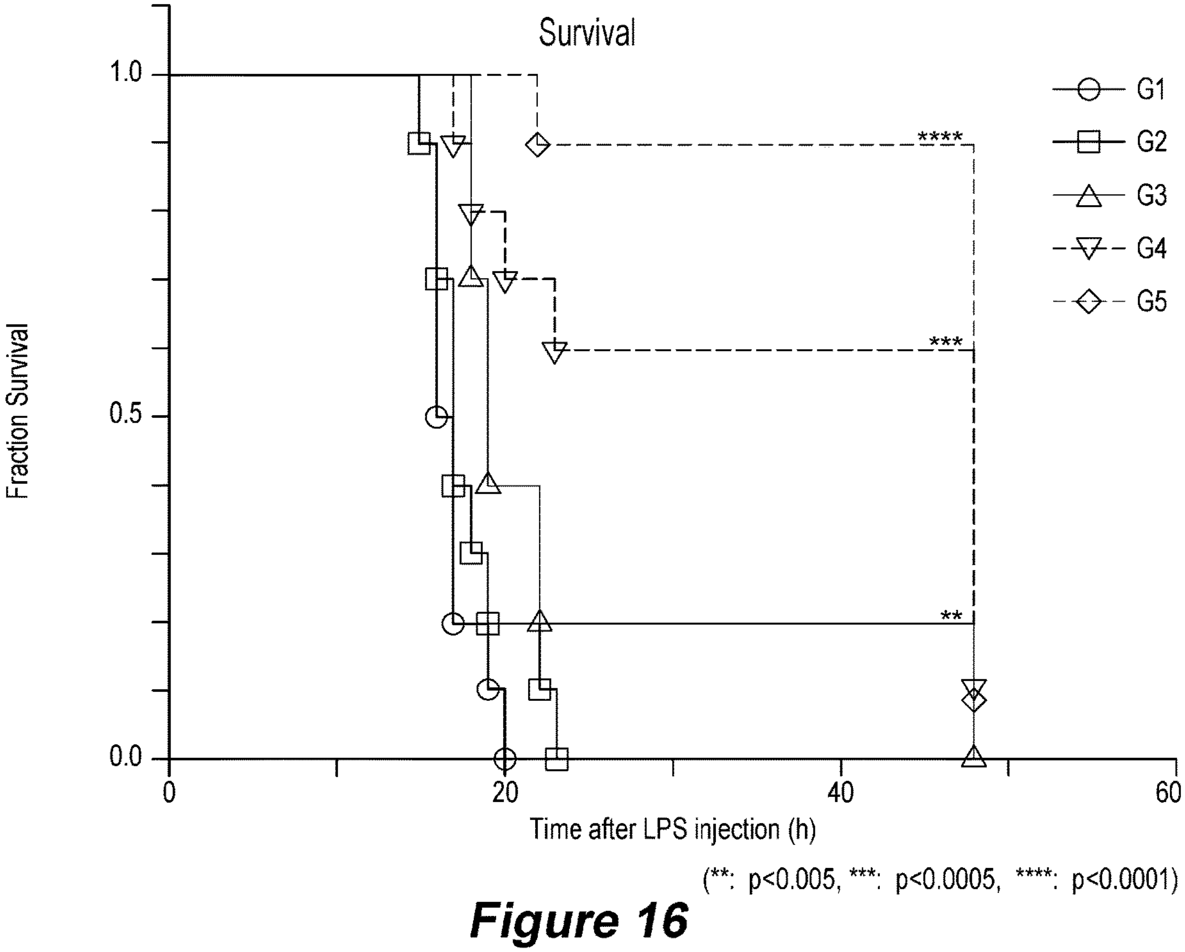
FIG. 16 is a graph showing survival of mice in an ARDS mouse model following treatment with PAX-1 (SMA), dexamethasone or no treatment (G1 (negative control, 0 mg/kg), G2 (PAX-1, 1.03 mg/kg), G3 (PAX-1, 1.54 mg/kg), G4 (PAX-1, 2.05 mg/kg), G5 (dexamethasone, 3 mg/kg); p<0.005, significant difference from the negative control (G1) by Log-rank (Mantel-Cox) test; *p<0.0005, significant difference from the negative control (G1) by Log-rank (Mantel-Cox) test; ****p<0.0001, significant difference from the negative control (G1) by Log-rank (Mantel-Cox) test; n=10).

4.3.2 Survival Analysis 4.3.2.1 Survival Analysis (FIG. 16)

Dead mice were checked every hour after treating 20 mg/kg of LPS. Survival rate was confirmed to be extended when compared to the negative control group (G1) with statistical significance (G3: $p<0.005$, G4: $p<0.0005$, G5: $p<0.0001$).

4.3.3 Body Weight and General Symptoms

Body Weight

The average body weight of all mice was 22.3 g at the entry and 24.1 g at group assignment. Normal body weight gain was observed during the quarantine acclimation period.

The group assignment was performed such that all groups had the average body weight. There was no statistical significance ($p<0.05$) when compared to the negative control group (G1).

General Symptoms

During the quarantine acclimation period, where observation for general symptoms was performed daily, no abnormality was observed.

During the study period, a total of 8 deaths occurred due to lung liquid infusion through intratracheal method for LPS treatment. A symptom of respiratory distress occurred in entities right after the end of intratracheal administration. Although temporary respiratory distress was observed in all mice treated with LPS, it seems that the temporary respiratory distress was due to the liquid volume from LPS administration and not LPS-induced respiratory distress syndrome. Yet, 8 mice seem to have no recovery from the symptom. Actions such as cardio-pulmonary resuscitation and body temperature maintenance were done for the 8 mice with severe respiratory distress; however, they died and samples for analysis were not acquired.

4.4. Conclusion

This study was conducted to confirm the inhibitory effect of the test substance, SMA, on LPS-induced proinflammatory mediators in acute respiratory syndrome (ARDS) model of *Mus musculus* (BALB/c) which was induced by repetitive LPS treatment via intratracheal administration. The results of this study confirm the inhibitory effect of the test substance and positive control substance on LPS-induced proinflammatory mediators and showed that the expression of the cytokines known to be the major mediators (TNF-α, IL-6, IL-1β) for acute respiratory distress syndrome was significantly suppressed in bronchoalveolar lavage fluid (BALF).

This study confirmed that the test substance, SMA, inhibits production of TNF-α and IL-6 at particular time points, and that the test substance, SMA, is effective as a preventive treatment for acute respiratory syndrome.

Although the analytical values of IFN-gamma, GM-CSF, and IL-1β were below the limit of quantification at some timepoints and, therefore, excluded from the analysis, the test substance, SMA, inhibited the production of IL-1β in a dose-dependent manner at some timepoints.

In conclusion, SMA exerts rapid inhibitory effect on the production of proinflammatory mediators such as TNF-α, IL-6 and IL-1β, and thus can be used to prolong survival by alleviating acute respiratory syndrome.

Example 5—In Vitro Experiments Showing that SMA Exhibits Viral Suppression Effects Against SARS-CoV-2

The in vivo experiments described in Example 4 above confirmed that PAX-1 (SMA) was effective in inhibiting inflammatory cytokines similar to that of dexamethasone, a drug approved for use as a treatment for SARS-CoV-2-related pneumonia in Europe.

Example 5 describes an in vitro study which also revealed that PAX-1 exhibited a similar viral suppression effect as the antiviral drug, remdesivir. PAX-1 has antiviral and anti-inflammatory properties and is effective to treat diseases such as viral infection-induced pneumonia. Treatment with PAX-1 is expected to bring a significant reduction in the recovery period to as short as one week. Progression of COVID-19-associated disease may be prevented if PAX-1 is taken during the early stages of infection.

5.1 Mechanism of Viral Suppression/Death and Inhibition of Inflammatory Cytokines The mechanism of action of PAX-1 involves specific binding of PAX-1 on telomeres of solid human tumour cell lines, leading to telomere-associated DNA damage, telomere erosion and cell death (Phatak P, Dai F, Butler M, et al. (2008) KML001 Cytotoxic Activity Is Associated with Its Binding to Telomeric Sequences and Telomere Erosion in Prostate Cancer Cells. Cancer Therapy: Preclinical 14(14): 4593-4603). PAX-1 also shows suppression of the proliferation of cancer cells by reducing the expression of transcription factors which are involved in transcription of telomerase mRNA. Furthermore, binding of PAX-1 to telomeric sequences at a ratio of one molecule per three TTAGGG repeats leads to translocation of the telomerase catalytic subunit called telomerase reverse transcriptase (hTERT) into the cytoplasm, thereby inhibiting telomerase activity and eventually killing cancer cells. A recent study has discovered structural and functional similarities of hTERT domain to viral RNA-dependent RNA polymerase (RdRP) by having conserved reverse transcriptase motifs consisted of a right-handed architecture (fingers, thumb, and palm domains) (Machitani M, Yasukawa M, Nakashima J, Furuichi Y, Masutomi K. RNA-dependent RNA polymerase, RdRP, a promising therapeutic target for cancer and potentially COVID-19. Cancer Sci. 2020 Aug. 17; 111(11):3976-84. doi: 10.1111/cas.14618). Viral RdRP serves an essential function in transcription of viral genome and replication, and suppression of RdRP is considered as one of the main targets for antiviral drugs. Given the proven inhibitory effect of PAX-1 on hTERT and the structural similarity of viral RdRPs and hTERT RdRP domain, it is plausible to propose that the inhibition of RdRP activity of hTERT by PAX-1 can be applied to inhibit RdRP activities of coronavirus. Moreover, the antiviral property of PAX-1 is not limited to coronavirus but can also be applicable to wider range of viruses, indicating a versatile treatment property of PAX-1 for anticancer and antivirus treatment (Machitani M, Yasukawa M, Nakashima J, Furuichi Y, Masutomi K. RNA-dependent RNA polymerase, RdRP, a promising therapeutic target for cancer and potentially COVID-19. Cancer Sci. 2020 Aug. 17; 111(11):3976-84. doi: 10.1111/cas.14618).

Sodium metaarsenite has been shown to be potent inhibitor of human telomerase.

The excessive production of cytokines in response to viral infection has been widely accepted as the main cause of COVID-19-induced pneumonia (inflammation).

Viral infection is followed by abnormal cellular activation of gene expression that leads to excessive release of cytokine, which in turn induces inflammation (pneumonia). PAX-1 is shown in Example 4 to inhibit or reduce the production/secretion of pro-inflammatory cytokines TNF-α, IL-1β and IL-6.

5.2 In Vitro Evaluation of the Antiviral Effects of PAX-1 Against SARS-CoV-2 Infected Cells 5.2.1. Overview The aim of this study was to verify the antiviral efficacy of PAX-1 against SARS-CoV-2. Antiviral efficacy of the compound was determined by a dose response curve (DRC) experiment in a SARS-CoV-2 cell infection model. Infected cells were imaged through immunofluorescence using a specific antibody for the viral nucleocapsid (N) protein, and the acquired images were analyzed using Columbus software (Perkin Elmer).

According to the experiments conducted by the Pasteur Institute, the antiviral effect of PAX-1 ($IC_{50}$=4.25 μM) is slightly higher than that of remdesivir ($IC_{50}$=5.27 μM), indicating that PAX-1 has an antiviral property comparable to remdesivir.

5.2.2. Materials and Methods 5.2.2.1 Viruses and Cell Lines

SARS-CoV-2 was provided by the Korea Centers for Disease Control and Prevention (KCDC), and Vero cells were obtained from ATCC (ATCC-CCL81).

5.2.2.2 Reagent

Chloroquine, lopinavir, and remdesivir were used as reference compounds and were purchased from Sigma-Aldrich, SelleckChem, and MedChemExpress, respectively. The primary antibody specific for the Anti-SARS-CoV-2 N protein was purchased from Sino Biological, and the secondary antibodies Alexa Fluor 488 goat anti-rabbit IgG and Hoechst 33342 were purchased from Molecular Probes.

5.2.2.3 Dose Response Curve Analysis by Immunofluorescence Method

A 384-tissue culture plate was inoculated with $1.2\times10^4$ Vero cells per well. After 24 hours of seeding, 10 different concentrations of compound were prepared by serial dilution in DMSO and PBS and cells were treated where the highest concentration was 50 μM. An hour after drug-treatment, cells were infected with SARS-CoV-2 (0.0125 MOI) in a BSL3 facility and incubated at 37 °C for 24 hours. Thereafter, cells were fixed with 4% paraformaldehyde (PFA), followed by permeabilization. Then, the cells were stained with anti-SARS-CoV-2 nucleocapsid (N) primary antibody, Alexa Fluor 488-conjugated goat anti-rabbit IgG secondary antibody and Hoechst 33342. Fluorescence images of infected cells were acquired using image analysis device, Operetta (Perkin Elmer).

5.2.2.4 Image Analysis

The acquired images were analyzed using Columbus software. The total number of cells stained with Hoechst per well were counted and were taken as the total number of cells. The number of cells expressing virus N protein was taken as the total number of infected cells. Infection ratio was calculated as the number of cells expressing the N protein/total number of cells.

The degree of infection per well was normalized to the average infectivity of wells of uninfected cells (mock) in the same plate and the average infectivity of wells of infected cells treated with 0.5% DMSO (v/v).

The cytotoxicity of the compound was normalized by normalizing the number of cells in each well to the average number of cells in the mock group wells and expressed as "cell number to mock" in the graph.

The response curve derived from each drug concentration and the $IC_{50}$ and $CC_{50}$ values were derived using the equation $Y=Bottom+(Top-Bottom)/(1+(IC_{50}/X)^{Hillslope})$ of XLFit 4 (IDBS) software. All $IC_{50}$ and $CC_{50}$ values were calculated from a fitted dose-response curve obtained from two replicates of independent experiments, and the Selectivity index (SI) value was calculated as $CC_{50}/IC_{50}$.

5.2.3. Results—Dose Response Curve (DRC) Analysis of Compound

This study explored the antiviral effects of PAX-1 on the replication of SARS-CoV-2 (COVID-19 virus) in Vero cells, as well as its possible cytotoxic effects, in comparison with remdesivir (i.e. the first antiviral drug to be authorized for use during the COVID-19 pandemic) and lopinavir (i.e. a drug currently under evaluation as an antiviral treatment for COVID-19 in combination with ritonavir).

Vero cells are a cellular model widely used and accepted to replicate and isolate SARS-CoV-2. Briefly, Vero cells (ATCC-CCL81) were infected with SARS-CoV-2 (obtained from Korea Disease Control and Prevention Agency) at a multiplicity of infection (MOI) of 0.0125 in the presence of varying concentrations of the test drugs or DMSO/PBS (control). Infected cells were fixed at 24 h post infection and stained with anti-SARS-CoV-2 nucleocapsid antibodies and Hoechst 33342 to identify the total number of infected cells using immunofluorescence staining method. Image analyses were performed using Operetta (Perkin Elmer). The half maximal inhibitory concentration ($IC_{50}$) and the half maximal cytotoxic concentration ($CC_{50}$) values of each drug were determined using fitted dose-response curves.

Figure 17:
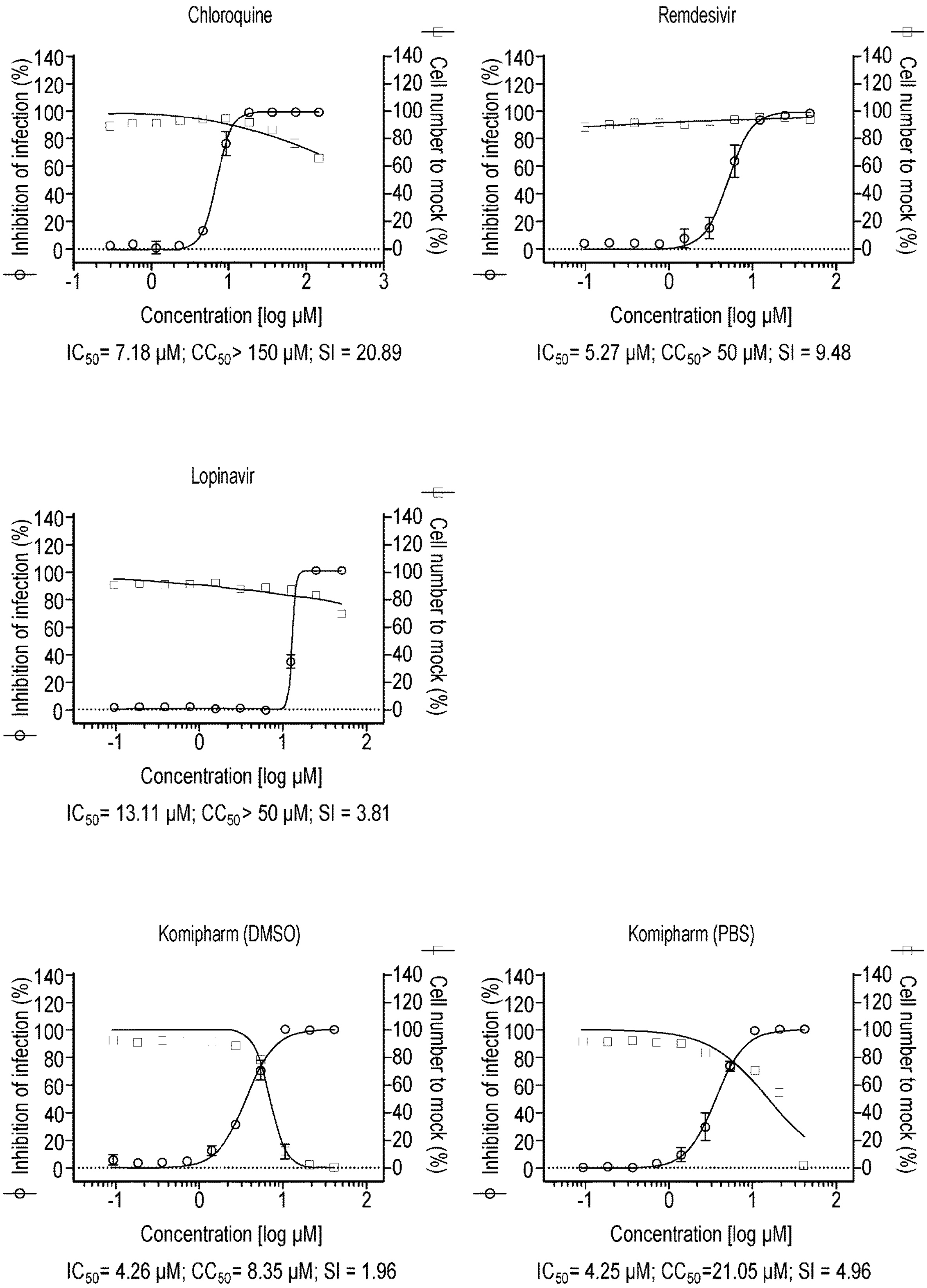
FIG. 17 are graphs showing inhibition of SARS-CoV-2 replication by chloroquine, remdesivir, lopinavir, PAX-1 (SMA) in DMSO ("Komipharm (DMSO)"), and PAX-1 (SMA) in PBS ("Komipharm (PBS)").

The results are shown in FIG. 17. Blue dot indicates the SARS-CoV-2 inhibition of infection of the compound, and red square indicates cytotoxicity for the compound.

As shown in the FIG. 17, SARS-CoV-2 replication was inhibited by PAX-1 ('Komipharm (PBS)' in FIG. 17) in a comparable manner as remdesivir and more efficiently than lopinavir. The $IC_{50}$ value for PAX-1 inhibition of SARS-CoV-2 infection was 4.25 μM, namely of the same order of magnitude as remdesivir ($IC_{50}$=5.27 μM) and an order of magnitude lower than lopinavir ($IC_{50}$=13.11 μM). The $CC_{50}$ value of PAX-1 was 21.05 μM, compared with that of both remdesivir and lopinavir being greater than 50 μM. Despite PAX-1 showing a slightly greater inhibition of cell viability compared with the other two compounds, its SI for antiviral activity vs cytotoxicity, computed as $CC_{50}/IC_{50}$, was comparable to that of lopinavir. Thus, PAX-1 effectively inhibited SARS-CoV-2 replication in vitro.

5.2.4. Discussion

Cytotoxic concentration ($CC_{50}$) of PAX-1 on normal cells was 21.05 μM, which was 4.96 times higher than its antiviral activity index ($IC_{50}$, 4.25 μM), indicating the safety of the drug. There is no need to take 5 times higher concentration of PAX-1 than $IC_{50}$ value to achieve the antiviral effect.

Recent studies on PAX-1 toxicity involved simultaneous testing of both remdesivir and lopinavir for comparison. The experimental results showed the following indices for lopinavir: $IC_{50}$=13.11 μM, $CC_{50}$>50 μM and the SI value of 3.81, reporting a higher cytotoxicity compared to PAX-1. Lopinavir is currently undergoing clinical trials as a treatment of COVID-19 led by the US FDA.

Considering above factors, PAX-1 can also be used as an antiviral agent without causing side effects or severe adverse effects during treatment.

PAX-1 binds to telomere sequence, a proliferative potential attached at the end chromosomes. The concentration of PAX-1 at which is used for inhibition of inflammatory cytokines, has no cytotoxic effect on normal immune cells. Furthermore, PAX-1 is fully metabolised and excreted from the body 72 hours after taking it.

A portion of patients in clinical trials for PAX-1 (472 patients involved in the clinical trials so far) were given up to 20 mg/day (takes 8 tablets a day). No death has been reported due to the toxicity of the drug, indicating PAX-1 is a very safe substance.

Growing evidence indicates that coronavirus antibodies wane rapidly and coronavirus from animal species can mutate and cross into human, creating the risk of reinfections. Without doubt, there is a great need for the rapid development of antiviral drugs against COVID-19.

Example 6—COVID-19 Patient Diary (Treatment with SMA)

Example 6 describes a day-to-day account of a 59-year old woman (with no pre-existing conditions) who contracted SARS-CoV-2 and was treated with SMA. This Example shows that SMA is effective in alleviating or treating the symptoms of SARS-CoV-2 infection, e.g. chest tightness, breathing difficulty, shortness of breath (dyspnea), fever, loss of appetite, runny nose, cough, sputum development, and pain.

| Day | Time | Observations |
|---|---|---|
| 1 | | Sudden onset of symptoms (has not been able to eat properly for 3 days). |
| 4 | | Symptoms of dehydration (including dry mouth). |
| | 3pm | Presented to Emergency Department, received electrolyte solution via i.v.<br>Only symptom was mild fever, therefore discharged.<br>Oral electrolytes self-taken. |
| 6 | 3am | Visited medical centre due to shortness of breath.<br>Emergency services called, carried by ambulance (with oxygen therapy) to major hospital. |
| | 3.30am | SARS-CoV-2 diagnostic tests commenced, medicines prescribed. |
| | 4am | Discharged. |
| 7 | 2am | Visited medical centre due to dyspnea with dehydration symptoms.<br>Emergency services called, carried by ambulance (without oxygen therapy) to major hospital. |
| | 3am | No special treatment other than prescription for SARS-CoV-2 confirmation.<br>[Prescription (5 days)]<br>Meiact tab 100 mg/1 tab 3 times a day (cefditoren pivoxil)<br>Rulide tab 150 mg/1 tab twice a day<br>Gaster D tab 20 mg/1 tab twice a day (famotidine)<br>Cough syrup 20 ml/three times a day<br>Zaltoprofen 80 mg/1 tab three times a day |
| | 4am | Discharged. |
| | 9am | SARS-CoV-2 diagnosis confirmed. |
| | 10am | Second request to be admitted to Public Health Centre (no beds available, awaiting for instructions for home treatment).<br>Prescription medicines taken by patient, but no improvement.<br>Fever present.<br>Juice, congee, soups gradually eating. |
| | 3pm | SMA taken after meal. |
| | 4pm | Chest tightness and mild pain. |
| | 7.30pm | SMA taken after meal. |
| | 8pm | Chest tightness and pain relieved. |
| 8 | 2am | SMA is taken due to recurrence of chest tightness and difficulty breathing.<br>Temporary relief of symptoms. |
| | 11am | SMA taken after meal.<br>Temporary relief of symptoms.<br>Suffering from sleep deprivation.<br>Anxiety due to delay in hospitalization. |
| | 5.30pm | SMA taken after meal.<br>Delivery of prescription for confirmed COVID-19 patients from the Public Health Centre.<br>[Prescription (5 days)]<br>Tamitra Semi tab/1 tab 3 times a day (acetaminophen/tramadol)<br>Levodropropizine 60 mg tab/1 tab 3 times a day<br>Nucomyt Cap. 200 mg/1 cap 3 times a day (acetylcysteine)<br>Streptokinase tab 10 mg/1 tab 3 times a day<br>Mucosil tab/1 tab 3 times a day (acetylcysteine) |
| | 6pm | Prescription medicine for confirmed COVID-19 patients commenced. |
| | 6pm | Received call from Public Health Centre.<br>(Received advice to keep active, eat and sleep well to maintain fitness)<br>Explained that sedative can be taken together with prescription medicines if required.<br>Patient has own P.R.N. sedative used 2-3 times a week (started 3 months prior). |
| | 7pm | When SMA is taken, chest tightness is relieved. When taking prescription medicines from the Public Health Office, chest tightness and inflammation feels exacerbated within 30 minutes. |
| | 12pm | SMA taken after meal. Public Health Office medicines and sedative taken 30 mins after. |
| 9 | 10am | Able to have slept due to sedative. However feels a bit drowsy as a side effect. |
| | 11:30am | SMA taken after meal. |
| | 12noon | Public Health Office medicines taken.<br>No dyspnea symptoms. Took a nap (due to prolonged sedative side effect). |
| | 5:20pm | Public Health Office medicines taken after meal. |
| | 5:40pm | SMA taken after meal.<br>No chest tightness and dyspnea since morning.<br>Condition recovery due to extra sleep.<br>Ascorbic acid (vitamin C) 3000 mg once a day commenced.<br>Can have regular food again. |
| | 6pm | Response from Public Health Centre - availability for admission at treatment centre. |
| | 8pm | Fever, dry mouth.<br>Anti-fever and gastroprotective medicine taken.<br>No breathing difficulty, but some sputum development.<br>(Feeling better than initial symptoms overall). |
| | 11:40pm | SMA taken after meal. |
| 10 | 8am | SMA and Public Health Office medicine taken after meal.<br>Was unable to sleep since day 9. Fever and dry mouth present.<br>Chest tightness, sputum and light cough (no shortness of breath).<br>Lack of sleep has significant effect on condition. |
| | 4pm | SMA and Public Health Office medicine taken after meal.<br>Dry mouth persistent. |
| | 8pm | Chest tightness subsides.<br>Dry mouth, chesty cough, headache.<br>Cough syrup/sedative taken. |

-continued

| Day | Time | Observations |
|---|---|---|
| | 10:30pm | Drowsy due to sedative. |
| | 11:50pm | SMA and Public Health Office medicine taken after meal. |
| 11 | | Slept due to sedative. |
| | 8am | SMA and Public Health Office medicine taken after meal. |
| | | Slept due to sedative. |
| | 11am | Condition improved due to sleep. |
| | | Continued chesty cough; dry mouth and chest tightness resolved. |
| | 4pm | SMA and Public Health Office medicine taken after meal. |
| | | Persistent chesty cough. |
| | 6pm | Transferred by ambulance to treatment centre (admitted). |
| | 10pm | SMA and Public Health Office medicine taken. |
| 12 | 9am | SMA and Public Health Office medicine taken after meal. |
| | | Good condition, slight cough/sputum, but mild. |
| | | No other symptoms. Body temperature 36.8 °C (normal range). |
| | 11am | No other SARS-CoV-2 associated symptoms. |
| | | No further medicine prescribed at Treatment Centre. |
| | 2:30pm | SMA taken after meal. |
| | | Slight runny nose, Public Health Office medicines ceased (new medicines to be started after dinner). |
| | 8pm | Normal body temperature (38 °C). Mild cough and gastrointestinal symptoms. |
| | 8:40pm | SMA taken after meal. |
| | 9pm | Anti-fever and gastroprotective medicine taken. |
| 13 | 9:30am | SMA taken after meal. |
| | | Appetite improves and the overall condition is very good (normal daily function restored). |
| | | Mild sputum. Normal body temperature (36.4 °C). |

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method of treating hypercytokinemia due to a viral infection in a subject, comprising administering to the subject an effective amount of sodium meta-arsenite ($O{=}As{-}O^{-}Na^{+}$) or potassium meta-arsenite ($O{=}As{-}O^{-}K^{+}$), wherein the viral infection is a coronavirus infection, and the coronavirus is SARS-COV-2.

2. The method of claim 1, wherein the sodium meta-arsenite ($O{=}As{-}O^{-}Na^{+}$) or potassium meta-arsenite ($O{=}As{-}O^{-}K^{+}$) is administered orally.

3. The method of claim 1, wherein the sodium meta-arsenite ($O{=}As{-}O^{-}Na^{+}$) or potassium meta-arsenite ($O{=}As{-}O^{-}K^{+}$) is administered at a dose in the range of from 2 mg per day to 20 mg per day.

* * * * *